United States Patent [19]
Rogers et al.

[11] Patent Number: 6,147,278
[45] Date of Patent: Nov. 14, 2000

[54] PLANT VECTORS

[75] Inventors: Stephen G. Rogers; Leslie Brand, both of Chesterfield; Robert B. Horsch; Robert T. Fraley, both of St. Louis; James Scott Elmer, Ellisville, all of Mo.; David Bisaro, Columbus, Ohio

[73] Assignee: Monsanto Company, St. Louis, Mo.

[21] Appl. No.: 09/261,770

[22] Filed: Mar. 3, 1999

Related U.S. Application Data

[63] Continuation of application No. 07/711,576, May 31, 1991, abandoned, which is a continuation of application No. 07/209,239, Jun. 26, 1998, abandoned, which is a continuation-in-part of application No. 06/899,270, Aug. 26, 1986, abandoned, which is a continuation-in-part of application No. 06/791,249, Oct. 25, 1985, abandoned.

[51] Int. Cl.[7] .......................... C12N 15/34; C12N 15/82; C12N 15/83; C12N 15/84
[52] U.S. Cl. ...................... 800/278; 800/288; 435/69.1; 435/320.1; 435/468; 435/469; 536/23.72
[58] Field of Search .................... 435/468, 469, 435/320.1, 69.1; 800/288, 278; 536/23.72

[56] References Cited

U.S. PATENT DOCUMENTS

| | | | |
|---|---|---|---|
| 4,407,956 | 10/1983 | Howell | 435/172.3 |
| 4,536,475 | 8/1985 | Anderson | 435/172.3 |

OTHER PUBLICATIONS

Howarth et al. J. Gen. Virol. 70:2717–2727, 1989.
Hamilton et al. EMBO J. 3(9):2197–2205, 1984.
Hamilton et al. Nucleic Acids Res. 11(21):7387–7398, 1983.
Buck et al. Plant Mol. Biol. 2:351–354, 1983.
Hamilton et al. FEMS Microbiol. Lett. 11(4): 263–267, 1981.
Goodman, R. J. Gen. Viro. 54: 9–21, 1981.

*Primary Examiner*—David T. Fox
*Attorney, Agent, or Firm*—Carol H. Clayman; Thomas P. McBride

[57] ABSTRACT

The invention relates to novel plant plasmid vectors comprising geminivirus DNA or a portion thereof having inserted therein a heterologous DNA sequence or gene, to processes and DNA intermediates useful in producing said vectors and to methods utilizing such vectors to replicate and express heterologous DNA sequences or genes in plants. In some embodiments, methods and compositions are provided for Ti plasmid delivery of these novel vectors into plants. In other embodiments, methods and compositions are provided which allow for the generation of geminivirus DNA containing plant plasmids in stably transformed plants. In still other embodiments, methods and compositions are provided for replicating and expressing heterologous DNA sequences or genes in plants employing the geminivirus DNA containing vectors of the present invention without causing disease symptoms.

5 Claims, 38 Drawing Sheets

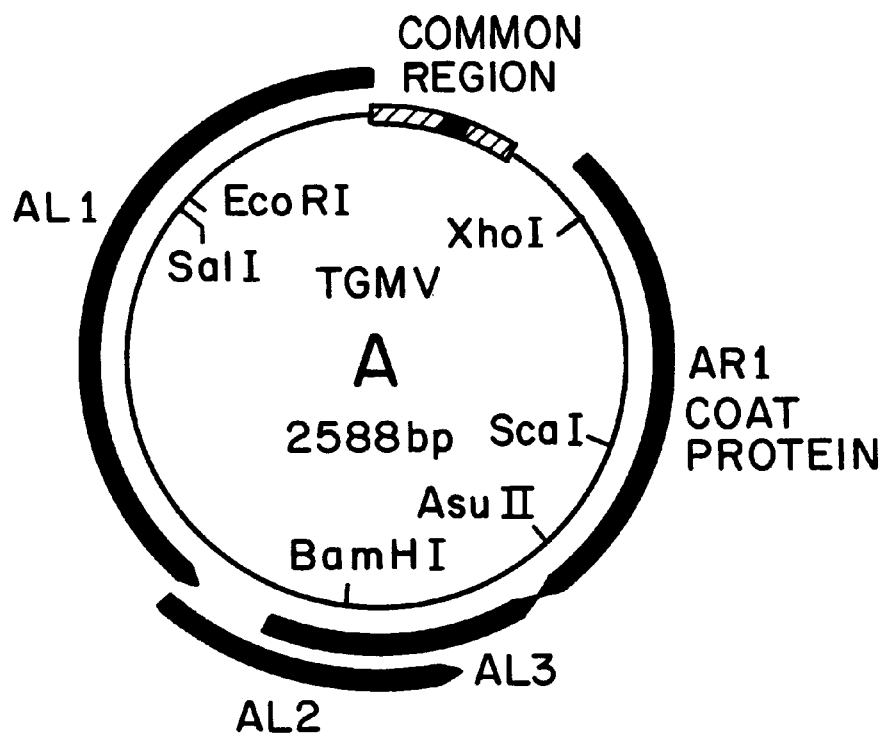
FIG. IA.
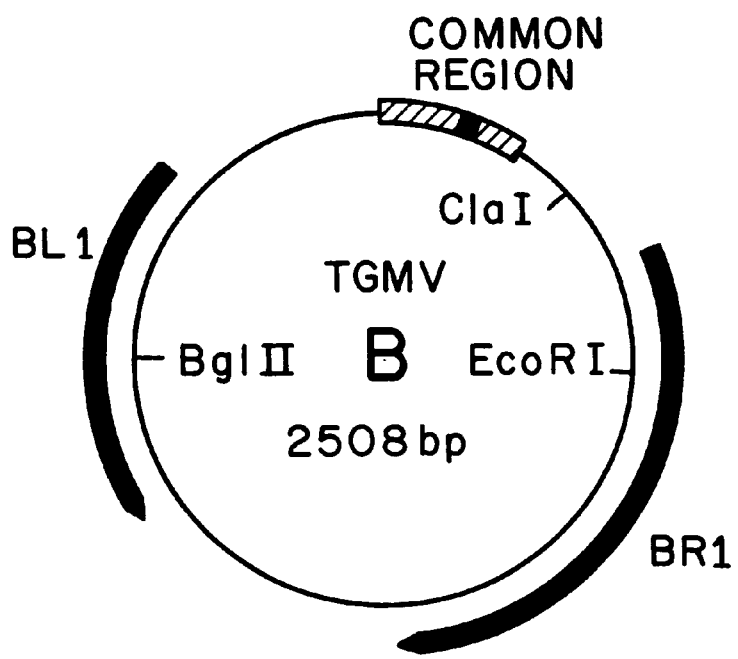
FIG. IB.

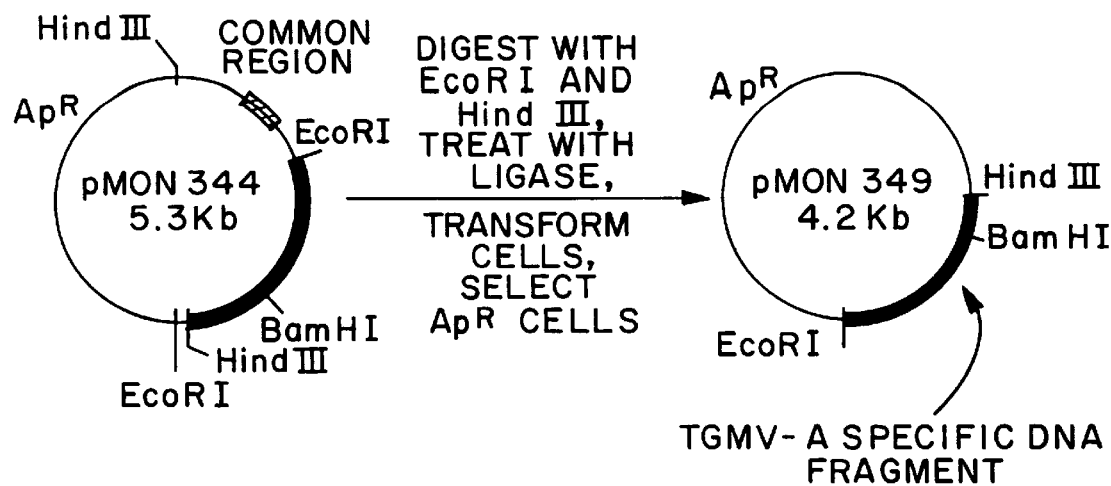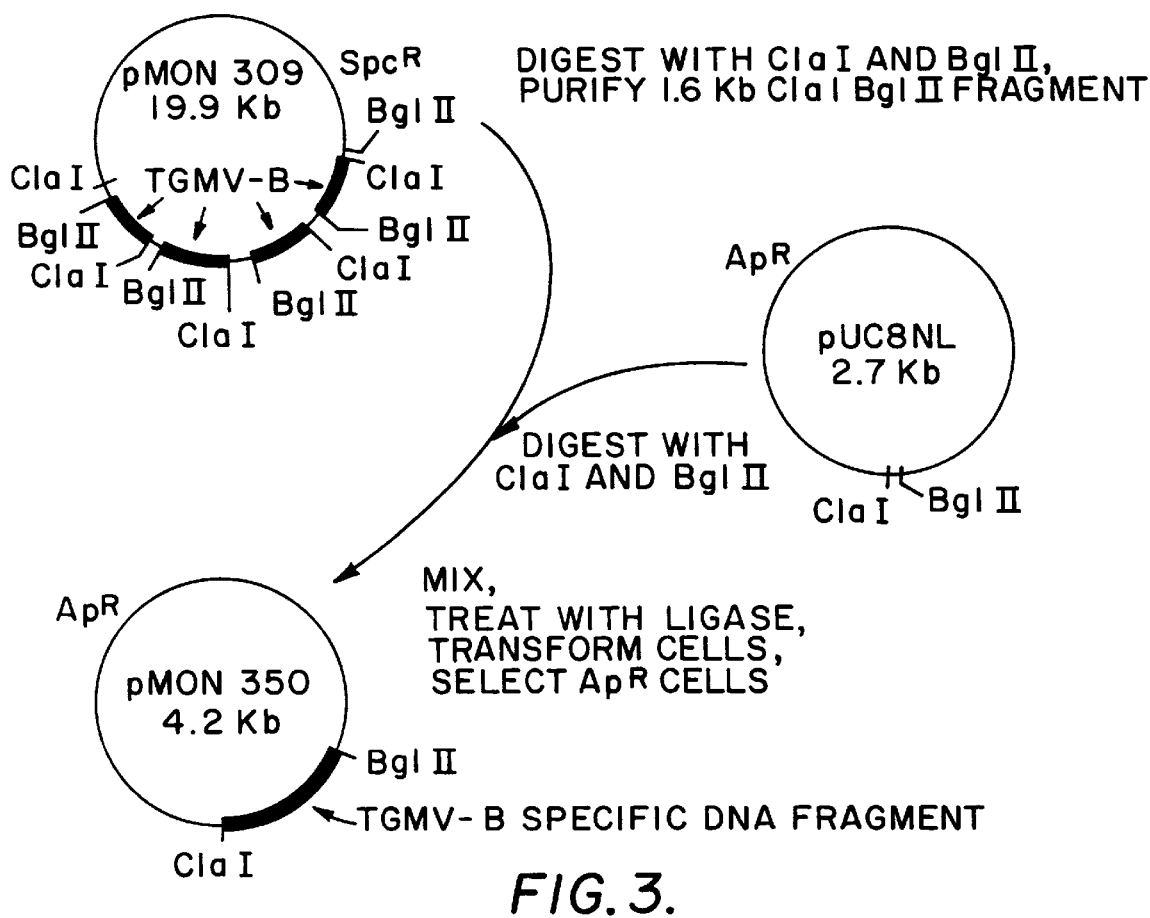
FIG. 3.

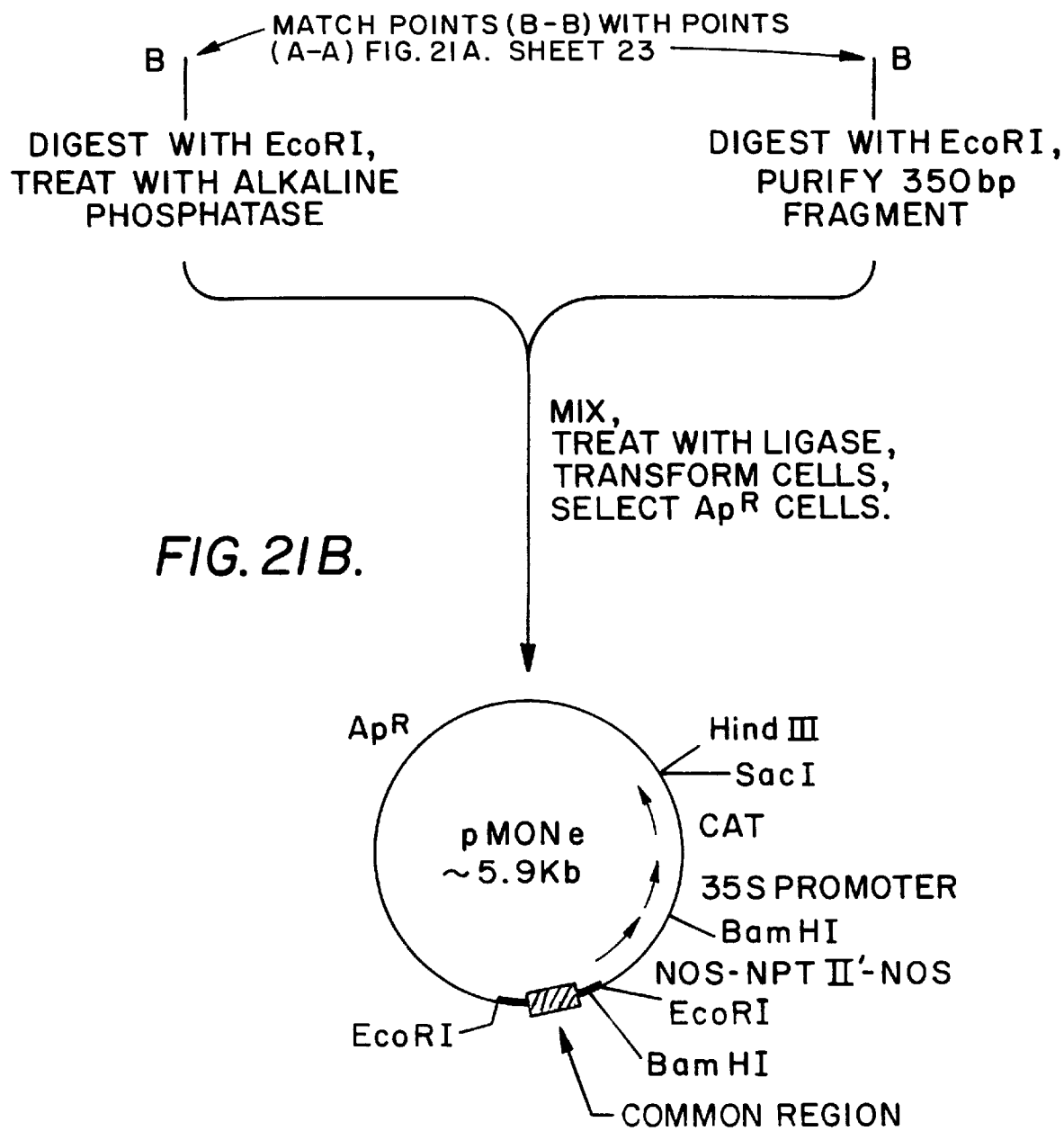

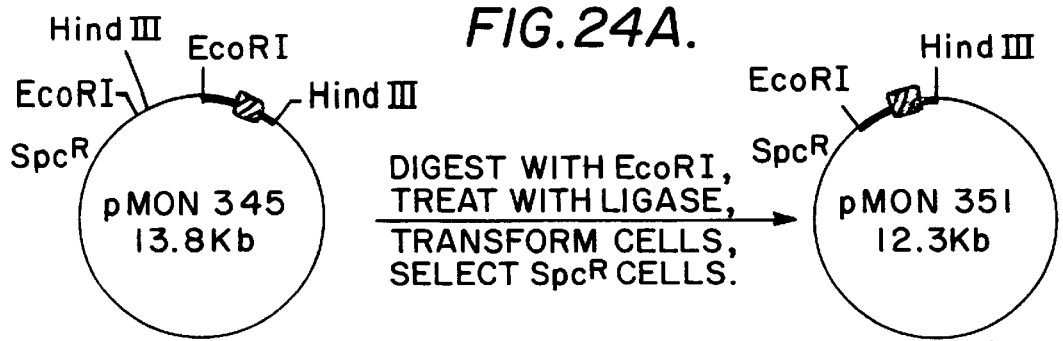
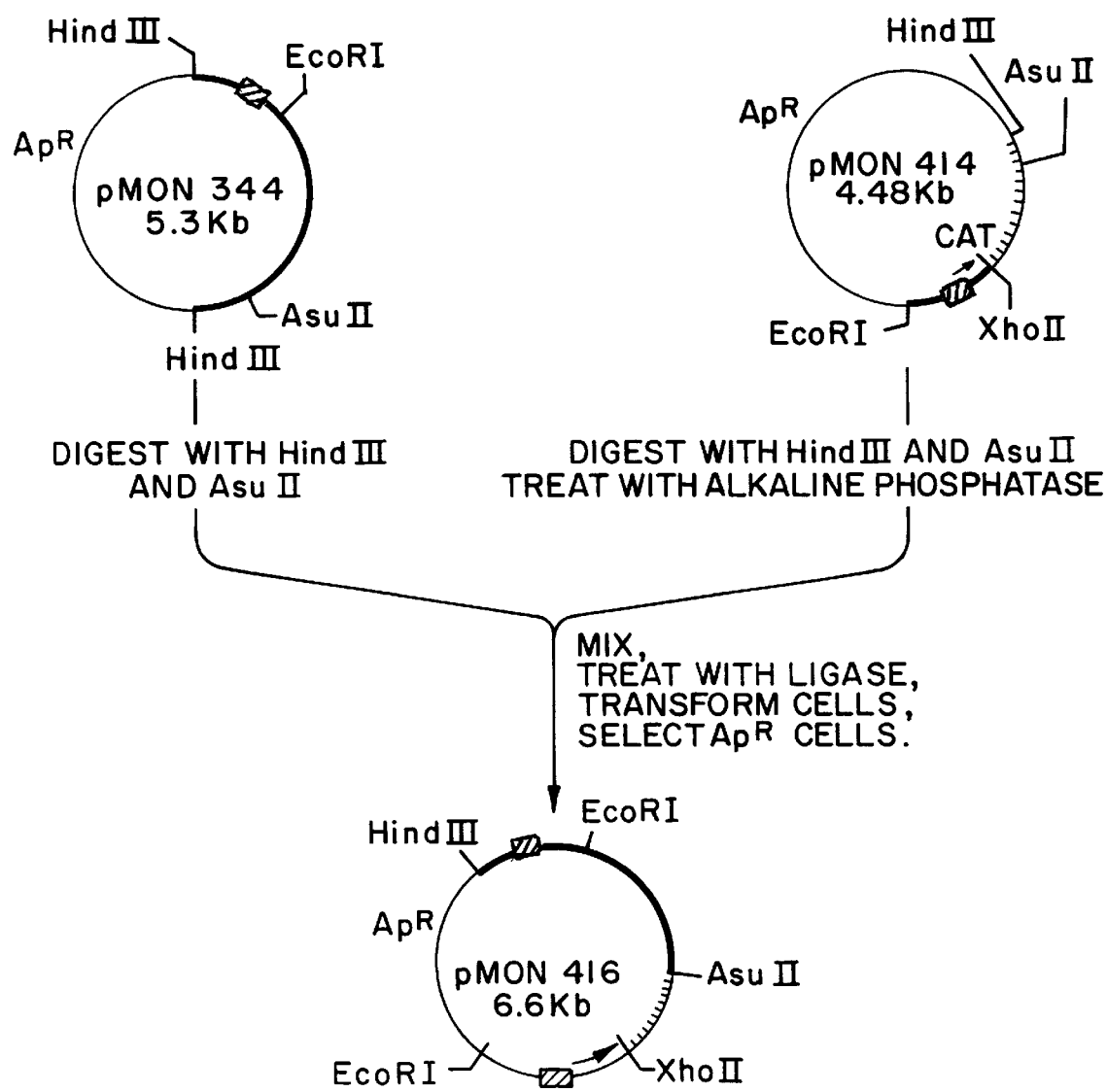
FIG. 24A.

PLANT VECTORS

CROSS-REFERENCE TO RELATED APPLICATION

This application is a continuation of application Ser. No. 07/711,576 filed May 31, 1991, now abandoned, which is a continuation of application Ser. No. 07/209,239 filed Jun. 26, 1988, now abandoned, which is a continuation-in-part of application Ser. No. 06/899,270 filed Aug. 26, 1986, now abandoned, which is a continuation-in-part of application Ser. No. 06/791,249 filed Oct. 25, 1985, now abandoned.

TECHNICAL FIELD

This invention was made, in part, with Government support under Grant No. 84-CRCR-1-1381 awarded by the United States Department of Agriculture. The Government has certain rights in this invention.

The present invention is directed to novel vectors which are or can give rise to plant plasmids, and methods and compositions for creating and using these vectors. In one important embodiment, geminivirus DNA is modified so as to create autonomously replicating DNA molecules capable of simultaneously replicating heterologous DNA sequences in plants.

BACKGROUND OF THE INVENTION

Advances in recombinant DNA technology and genetic engineering have provided a means for producing in bacteria specific proteins of commercial and economic importance. In many instances, the specific proteins sought to be produced in bacteria are of eucaryotic origin. In the course of developing such bacterial host factories for eucaryotic protein production, it has become increasingly evident that bacteria are unable to consistently provide the post-translational modifications such as proper protein folding, glycosylation and the like required for functional eucaryotic protein production. It is, therefore, desirable to develop eucaryotic cell systems which can provide these post-translational modifications and thus become efficient factories for functional and/or antigenically homologous eucaryotic protein production.

A key element in the genetic engineering of both eucaryotic and procaryotic cells to effect heterologous protein production is the development of defined vectors or host-vector systems. "Vectors" or "vector systems" are herein defined as nucleic acid (e.g. DNA and/or RNA) molecules capable of providing for the replication of a desired (e.g. heterologous) nucleic acid sequence or sequences in a host cell. "Host-vector" systems are herein understood to mean host cells capable of accepting a given vector molecule into its genome. The term "genome" is herein defined as including any and all DNA, e.g. chromosomal and episomal, contained within a given host cell or virus particle. A "gene" is herein defined as comprising all the DNA required for expression of a DNA sequence e.g. production of the protein or fragment thereof encoded in the gene.

While numerous vector systems have been developed for procaryotic hosts and for such eucaryotic hosts as yeast and various mammalian cell lines, few such systems have been described for plants. The term "plant" shall include whole plants, plant parts and individual plant cells unless otherwise specified. Enhanced or de novo protein production in plant hosts may be desirable due to the lower cost of plant cell culture systems as compared to mammalian cell culture systems and for increased production of plant secondary products. Plant secondary products can include such medically important plant products as shikonin, digitalis, vinblastine and vincristine. By means of genetic engineering, the production of such plant secondary products may be increased by providing and/or amplifying the rate limiting enzymes in such product production and/or by increasing the number of copies per cell of a gene coding for such enzymes.

To date, only two vector systems have been described which allow for the introduction of a given gene in higher plants to effect desired protein production. The first system employs a tumor inducing (Ti) plasmid or portion thereof found in the bacterium Agrobacterium. A portion of the Ti plasmid is transferred from the bacterium to plant cells when Agrobacterium infects plants and produces a crown gall tumor. This transferred DNA is hereinafter referred to as "transfer DNA" (T-DNA). The transfer DNA integrates into the plant chromosomal DNA and can be shown to express the genes carried in the transferred DNA under appropriate conditions. It has further been shown that whole plants regenerated from a single plant cell transformed with a transfer DNA carry the integrated DNA in all cells. These cells, however, generally carry only one to 5 copies of the transfer DNA and are thus limited in the amount of transfer DNA gene products which may be produced in the transformed plant cells. It is believed that by introducing multiple copies of a given DNA sequence or gene, greater levels of desired protein production may be achieved. Thus, it is desirable to develop a means for introducing or inducing more than about 5 copies of a given gene per host cell to effect increases in gene-specific products.

The second vector system employs cauliflower mosaic virus (CaMV) DNA as a vector for introduction of desired DNA sequences into plant cells. CaMV is a member of the caulimovirus group and contains a double-stranded DNA genome. To date, the CaMV system has only been applied to whole plants and requires infectious virus production. Thus the CaMV vector system is limited by three important factors. The first is host range, the second is a limitation on the size of the desired DNA sequences which may be carried in the CaMV DNA vectors and the third is resultant disease caused by the introduction of whole virus DNA. The resultant disease associated with the currently applied CaMV vector systems prevents its potential use in the stable transformation of whole plants to effect such improvements as increased plant resistance to herbicides, resistance to other disease factors, increased protein production, increased crop yield and the like. Furthermore, infection of whole plants requires that the CaMV DNA retain the necessary viral functions for infectivity, replication, movement throughout the whole plant and packaging into infectious virus particles. Thus, the maximum size of a desired DNA sequence which may be carried in CaMV DNA vectors has thus far been limited to 240 base pairs (bp), only enough DNA to encode a small peptide. A further limitation of the CaMV vector system is that the heterologous or foreign DNA so introduced is not seed transmitted.

Recently a new technique for introduction of desired (e.g. heterologous) DNA sequences into a given host has been developed. This technique is called electroporation. Presently, however, this technique is limited by a low frequency of introduction and, in plants, is only operable in protoplasts and hence cannot be practically employed to engineer plants where regeneration of whole plants from protoplasts is not possible.

It is, therefore, desirable to develop a plant vector system that is capable of carrying both small and large (e.g. greater than 250 bp) heterologous DNA sequences or genes, able to generate a high copy number of introduced DNA sequences, and exhibits a broad host range.

To date, only one other group of plant viruses has been identified which contains a DNA, rather than RNA genome. This group comprises the geminiviruses. Geminiviruses are plant viruses characterized by dumbbell-shaped twinned icosahedral particles (seen by electron micrograph). Some geminiviruses comprise two distinct circular single-stranded (ss) DNA genomes. Examples of such two genome or binary geminiviruses include tomato golden mosaic virus (TGMV) which has an "A" DNA and a "B" DNA, Hamilton (1981, 1982, 1983, and 1984); Stein (1983); and Bisaro (1982), and Cassava latent virus (CLV) which has a "1" DNA and a "2" DNA (Stanley and Gay, 1983). Other geminiviruses such as maize streak virus (MSV) are believed to have a single circular ssDNA genome; Donson (1984). Typically, two genome (binary) geminiviruses are transmitted by white flies, while single genome geminiviruses are transmitted by leaf hoppers. As a group, geminiviruses infect both monocotyledonous and dicotyledonous plants and thus exhibit a broad host range.

All geminivirus particles carry circular ssDNA. In infected plant cells, geminivirus DNA sequences have been detected as both ss and double-stranded (ds) DNA, in predominately circular form. In infected plants, such sequences exist in the plant cell nuclei, apparently as episomes, at several hundred copies per nuclei. Thus, unlike the transfer DNA (T-DNA) derived from the Ti plasmids of Agrobacterium, these geminivirus DNA sequences are not integrated into plant chromosomal DNA and generate multiple copies (e.g. more than 5) per infected cell. In infected plants, geminivirus particles released by an infected cell can infect other cells throughout the plant. In the two genome geminivirus systems such as TGMV, infectivity, replication and movement throughout the whole plant has thus far been shown to require the presence of both the A and B components. Other than reports that the two DNA genomes of binary geminiviruses are simultaneously required for complete and systemic infection of binary geminiviruses in whole plants, the precise mode of and requirements for geminivirus DNA replication itself in plants or plant cells has not clearly been elucidated.

Scientists have speculated about the possibility of using geminiviruses to create episomal DNA molecules which function as plasmids in plant cells (Buck, 1983). A "plasmid" is herein defined as an episomal DNA molecule capable of autonomous replication in a host cell.

In order for geminivirus DNA to be useful as a vector in plants, the DNA must be capable of autonomous replication in plants, be able to generate a high copy number in plants, be able to have inserted therein a heterologous DNA sequence or gene, be able to simultaneously replicate itself and the inserted gene or DNA sequence in plant cells, preferably, contain a marker for positive identification and/or selection of plants transformed with the vector, and, ideally, not cause disease symptoms. No one has heretofore taught how to modify geminivirus genomes so as to allow them to function in the foregoing manner.

The term "heterologous" as applied to a nucleic acid (e.g. DNA or RNA) sequence (molecule) or gene means a nucleic acid sequence or gene, respectively, at least a portion of which contains a nucleic acid sequence not naturally contained within a geminivirus genome. The term "heterologous" as applied to a protein means a protein at least a portion of which contains a protein sequence not naturally encoded by a geminivirus genome.

SUMMARY OF THE INVENTION

The present invention provides plant plasmids comprising a heterologous DNA sequence and a segment of a coat protein-encoding geminivirus DNA which permits autonomous replication of the plant plasmid in a plant cell. In one preferred embodiment, the segment of a coat protein-encoding geminivirus DNA is selected from a binary (two genome) geminivirus and the heterologous DNA sequence is inserted into the geminivirus coat protein gene.

In another embodiment, plant vectors able to produce plasmid DNA in a plant cell are provided. Such vectors comprise a heterologous DNA sequence and a segment of a coat protein-encoding geminivirus DNA which permits autonomous replication of plasmid DNA in a plant cell. In one preferred embodiment, the plant vector comprises a first DNA segment containing a heterologous DNA sequence and a segment of a coat protein-encoding geminivirus DNA which permits autonomous replication of a plasmid DNA in a plant cell and in which the first DNA segment is flanked by a second DNA segment which permits release of a plant plasmid from the plant vector.

In still another embodiment, methods and compositions for creating the plant plasmids and plant vectors of the present invention are provided.

In yet another embodiment, methods and compositions for producing a desired (e.g. heterologous) polypeptide in plants are provided.

In still a further embodiment, methods and compositions for creating genetically transformed plants able to produce a desired polypeptide in enhanced amounts are provided.

BRIEF DESCRIPTION OF THE DRAWINGS

In the following diagramatic representations, the directional arrows represent the 5' to 3' orientation of the coding sequences. Only relevant restriction endonuclease sites are shown. The DNA regions so marked are for diagrammatic purposes only and are not drawn to scale. Antibiotic resistance genes for ampicillin, chloramphenicol and spectinomycin are abbreviated $Ap^r$, $Cm^r$, and $Spc^r$, respectively, and are shown where relevant. The squiggly lines represent relevant restriction endonuclease sites, as labeled, which have been removed. Where relevant, the approximate size of a plasmid or DNA fragment is given in kilobases (kb).

FIGS. 1A and 1B depict the TGMV-A and -B components. The hatched box represents the TGMV common region and the blackened box inside the common region represents the highly conserved geminivirus DNA sequence.

FIG. 3 depicts the construction of pMON349 carrying TGMV-A DNA in which the common region has been deleted, and construction of pMON350 carrying TGMV-B DNA in which the common region has been deleted.

FIGS. 21A–21B depict the construction of pMONe comprising pMONc carrying a 350 bp region (blackened area) isolated from pMONd and inserted into the EcoRI restriction endonuclease site of pMONc. The hatched box denotes the CLV common region.

FIGS. 24A–24B depict the construction of pMON417 comprising pMON505 having inserted therein a CAT gene, denoted by a dotted line and flanked at both ends by a TGMV-A DNA segment, denoted by a blackened line. The hatched box denotes a TGMV common region.

DETAILED DESCRIPTION OF THE INVENTION

Figure 2A:
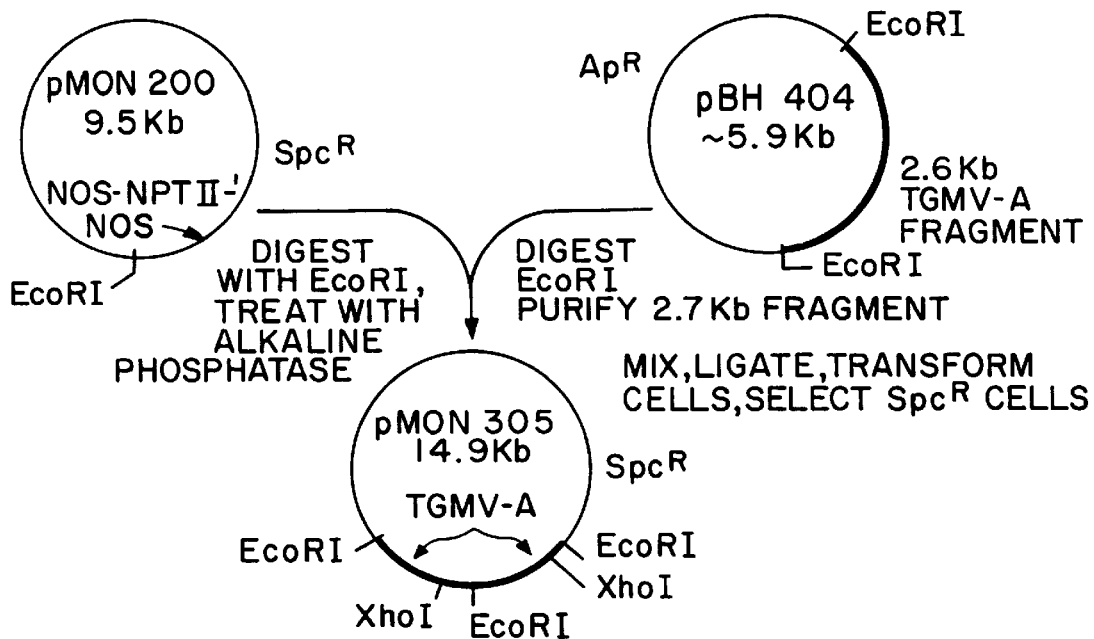
FIG. 2A depicts the construction of pMON305 comprising pMON200 having inserted therein at the EcoRI restriction endonuclease site tandem copies of TGMV-A DNA. The TGMV-A DNA is represented by the blackened area.

The present invention provides novel methods and compositions for modifying geminivirus DNA, particularly, two genome (binary) geminivirus DNA, to create novel plant plasmids and plant vectors. The present invention further provides novel methods and compositions for the generation of novel plant plasmids in stably transformed plants or plant cells. Additionally, the novel plant plasmids produced in accordance with the present invention provide a valuable means for replicating and/or expressing a heterologous DNA sequence or gene in plants or plant cells. Such heterologous DNA sequences include endogenous plant cell DNA sequences or genes, exogenous, non-geminivirus DNA sequences or genes, and chimeric DNA sequences or genes which contain, at least in part thereof, DNA sequences not naturally contained within a geminivirus genome. These heterologous DNA sequences or genes are typically associated with the production of proteins that make a plant more useful (e.g. proteins associated with or conferring herbicide resistance, disease resistance and/or crop yield), useful proteins to be recovered from plants or plant cells and proteins that cause the synthesis of chemicals or compounds that make a plant or plant cells more useful agriculturally or medicinally.

Examples of desired polypeptides and/or organic compounds which may be produced in enhanced amounts using the invention are digitalis, vinblastine, vincristine, plant growth factors, herbicide resistance factors, disease resistance factors and other such chemical products which may enhance crop nutritional yield. Further specific examples of such heterologous DNA sequences or genes are those providing for production of enol pyruvyl shikimate phosphate (EPSP) synthase, glutathione-S-transferase, phytohormones, phytoallexins, lignins, viral antigens (i.e. coat proteins) such medically important polypeptides as tissue plasminogen activator, mammalian growth hormones, insulin-like growth factor and atrial peptides and eucaryotic or procaryotic enzymes, such as, but not limited to, chloramphenicol acetyl transferase and dihydrofolate reductase.

Once the DNA sequence or gene providing for production of a desired chemical product is determined, such sequences or genes may be inserted into or joined to the plant vectors of the present invention by such conventional techniques as chemical and/or enzymatic linkage.

The complete DNA sequences of several of the two genome geminiviruses is now known as are the amino acid compositions or sequences of the coat proteins for several of these two genome geminiviruses. Stanley and Gay (1983); Mullineaux, P. M. et al. (1984); Hamilton, W. D. O. et al. (1984), and Howarth, R. et al. (1985). These sequences are hereby incorporated by reference hereto. It has also been determined that only one of the two genomic DNAs in binary geminiviruses carries a DNA sequence coding for a coat protein (e.g. a coat protein gene) Townsend, et al. (1985). The term "coat protein-encoding geminivirus DNA" or "coat protein-encoding DNA" as used herein refers to both the DNA of single genome geminiviruses and to the DNA molecules of binary (two genome) geminiviruses which carry a geminivirus coat protein gene, unless otherwise specified. Examples of such coat protein-encoding geminivirus DNAs include, but are not limited to, the genome of wheat dwarf virus (WDV), the genome of maize streak virus (MSV), the genome of beet curly top virus (BCTV), the "1" component of bean golden mosaic virus (BGMV), the "1" component of cassava latent virus (CLV) and the "A" component of tomato golden mosaic virus (TGMV).

As described more fully in the examples below, it was discovered that one of the DNA molecules of binary geminiviruses is capable of autonomously replicating in plant cells and in stably transformed (e.g. genetically transformed) plants. Specifically, it was discovered that the coat protein-encoding DNA of two genome geminiviruses is able to replicate (e.g. produce both ssDNA and dsDNA forms) in plant cells and/or in transgenic plants in the absence of the second (e.g. non-coat protein-encoding) genomic DNA molecule. It was further discovered that transgenic (e.g. genetically transformed) plants containing autonomously replicating coat protein-encoding DNA of binary geminiviruses do not produce disease symptoms. These discoveries are highly significant as they suggest that the coat-protein encoding DNA of a two genome geminivirus can now be employed as a plant vector that can provide for the replication and/or expression of heterologous DNA or genes in plants. Additionally, these discoveries suggest that binary geminivirus coat protein-encoding DNA can be employed to effectively replicate and express heterologous DNA sequences encoding desired chemical products in plants in the absence of such undesirable side-affects as disease.

Indeed, as described more fully below, the present invention provides methods and compositions which permit the replication and expression of heterologous DNA sequences in plant cells. Furthermore, by employing the methods and compositions described herein, plant plasmid DNA containing such heterologous DNA sequences have been demonstrated to be generated in a plant cell thereby providing a means for enhancing the synthesis of a desired polypeptide in a plant cell or plant. "Enhanced" polypeptide synthesis is herein understood to mean the generation of a greater than endogenous number of copies of a specific gene which either directly encodes the desired polypeptide and/or encodes a polypeptide that causes the synthesis of a desired chemical, ribonucleic acid sequence, compound or polypeptide.

Although TGMV is employed in the detailed examples of the present invention, those skilled in the art will be able to apply the disclosed methods and compositions to any of the binary geminiviruses including, but not limited to, bean golden mosaic virus (BGMV), mungbean yellow mosaic virus (MYMV), and cassava latent virus (CLV). (See Francki et al., 1985; Stanley, 1985). Additionally, the DNA of a single genome geminivirus may be alternatively employed.

It has been determined that a DNA sequence spanning approximately 200–250 nucleotides in length is shared by both the A and B (or "1" and "2") DNAs of a given binary geminivirus. This shared sequence is hereinafter generically referred to as the "common region". Furthermore, comparative DNA sequence analysis of both single and two genome geminivirus DNAs has revealed a highly conserved DNA sequence, approximately 9 nucleotides in length, in all geminivirus genomes analyzed to date. See MacDowell (1985). This highly conserved sequence is located within the common region of binary geminiviruses and the intergenic region of single component geminiviruses and in both instances is part of a stem and loop structure proposed by secondary structure analysis of sequenced geminivirus DNAs. While applicants do not wish to be bound by the following theory of mechanism, it is believed that the stem and loop structure and/or the highly conserved DNA sequence comprising 5'-TAATATTAC-3' are essential for the replication of geminivirus DNAs. Hence, a preferred geminivirus plant vector, whether derived from single or two genome geminivirus DNA, contains at least one copy of the highly conserved DNA sequence and/or the DNA sequences which provide the stem and loop structure and various nucleotides surrounding the stem and loop structure.

As described more fully below, it was discovered that the construction of geminivirus vectors containing a desired heterologous DNA sequence is primarily determined by the method chosen for delivery of the vector to a plant cell or plant.

To date, several methodologies exist which provide for the delivery of DNA sequences into plants. These delivery systems include whole virus infection, the Agrobacterium Ti plasmid systems, free DNA application to abraded or cut plant surfaces, and free DNA introduction into plant protoplasts by means of, for example, polyethylene glycol, calcium phosphate, poly-L-ornithine, micro-injection, or electroporation, Freeman et al. (1984), Fromm et al. (1985) and Griesbach (1983). It is understood by those skilled in the art that the Ti plasmid systems include both cointegrate and binary vector systems.

The present invention now teaches the necessary construction and/or components of geminivirus DNA, in particular binary geminivirus DNA, which provide for production of plant vectors for the various delivery systems which can be employed. Specifically for use in free DNA delivery systems, a preferred vector comprises a heterologous DNA sequence and a segment of a coat protein-encoding geminivirus DNA which permits autonomous replication of plasmid DNA in a plant cell. For use in Ti plasmid systems, a preferred vector comprises an *Agrobacterium tumefaciens* T-DNA which comprises a first DNA segment containing a heterologous DNA sequence and a segment of a coat protein-encoding geminivirus DNA which permits autonomous replication of plasmid DNA in a plant cell and a second DNA segment which permits release of a plant plasmid from the vector or plant chromosomal DNA and wherein the first DNA segment is flanked by the second DNA segment. In both vectors, the heterologous DNA sequence contains a DNA sequence coding for a polypeptide and/or a DNA sequence coding for a polypeptide that causes the synthesis of a desired chemical, compound or polypeptide.

Independent Replication of Coat Protein-Encoding DNA in Plants

As detailed in the examples below, it was first discovered that the A DNA (component) of TGMV, which carries the DNA sequence encoding the TGMV coat protein (FIG. 1), is capable of replication in plants in the absence of the TGMV-B DNA. Additionally, it was discovered that said replication in plants occurs without causing disease symptoms in plants. Thus, the TGMV-A DNA contains all of the DNA sequence information necessary to support its own duplication and generation of multiple copies of itself in plants without causing disease symptoms. The terms "TGMV-A DNA" and "TGMV-A component" are hereinafter used interchangeably and all refer to the TGMV-A DNA shown in FIG. 1. Similarly, the terms "TGMV-B DNA" and "TGMV-B component" are hereinafter used interchangeably and all refer to the TGMV-B DNA shown in FIG. 1.

In one embodiment of the present invention, TGMV DNAs were introduced into plant cells by means of a larger, intermediate Ti plasmid that may or may not become inserted into the chromosomes of the treated plant cells. TGMV-A and -B components were individually inserted into separate and distinct Ti vectors to create chimeric Ti vectors. Specifically, TGMV-A and -B DNAs were individually inserted into the transfer DNA (T-DNA) region of separate and distinct disarmed Ti plasmids in a construction which contains the entire specific TGMV DNA flanked by TGMV common regions or in tandem with a second TGMV genome. The term "flanked" as used herein means having a defined DNA sequence (i.e. a TGMV common region) contiguous with both ends of a given DNA sequence or segment. These chimeric vectors were thereafter employed to transform plant cells. The term "transform" is herein understood to include such terms as transfect, infect, transduce and the like which collectively represent means for the introduction of and/or acceptance of DNA sequences into the genome of a host cell.

In one preferred embodiment of the present invention, TGMV-A DNA was obtained as a 2,588 bp EcoRI fragment (Hamilton et al., 1984) inserted in the EcoRI site of pAT153 to give pBH404 (Bisaro et al., 1982). (FIG. 2A). In order to test the ability of the TGMV-A genes to be expressed from integrated copies in the chromosomes of transformed plants, a 2.6 kb EcoRI fragment was purified from EcoRI-cleaved pBH404 DNA, mixed with EcoRI-digested pMON200 DNA (Fraley et al. 1985 and Rogers et al. 1985) and treated with DNA ligase to give rise to a chimeric Ti plasmid designated pMON305 (FIG. 2A).

pMON200 is an intermediate vector capable of integrating into an Agrobacterium Ti plasmid such as, but not limited to, pTiB6S3-SE, to form a cointegrate Ti plasmid having a functional disarmed T-DNA. *Agrobacterium tumefaciens* strain GV3111-SE carrying the pTiB6S3-SE plasmid has been deposited with the American Type Culture Collection, (ATCC) (Rockville, Md.) and has been given ATCC accession number 53002. pMON200, thus represents an example of a cointegrate Agrobacterium Ti plasmid delivery system. A binary delivery system, as described in more detail below, may alternatively be employed. As shown in FIG. 2, pMON200 carries a spectinomycin resistance gene (Spc$^R$) useful as a selectable marker in bacteria and a chimeric kanamycin resistance (NOS-NPTII'-NOS) gene useful as a selectable marker in plant cells. (Fraley et al. 1985 and Rogers et al. 1985). Other such selectable markers known to those skilled in the art may alternatively be employed.

Figure 2B:
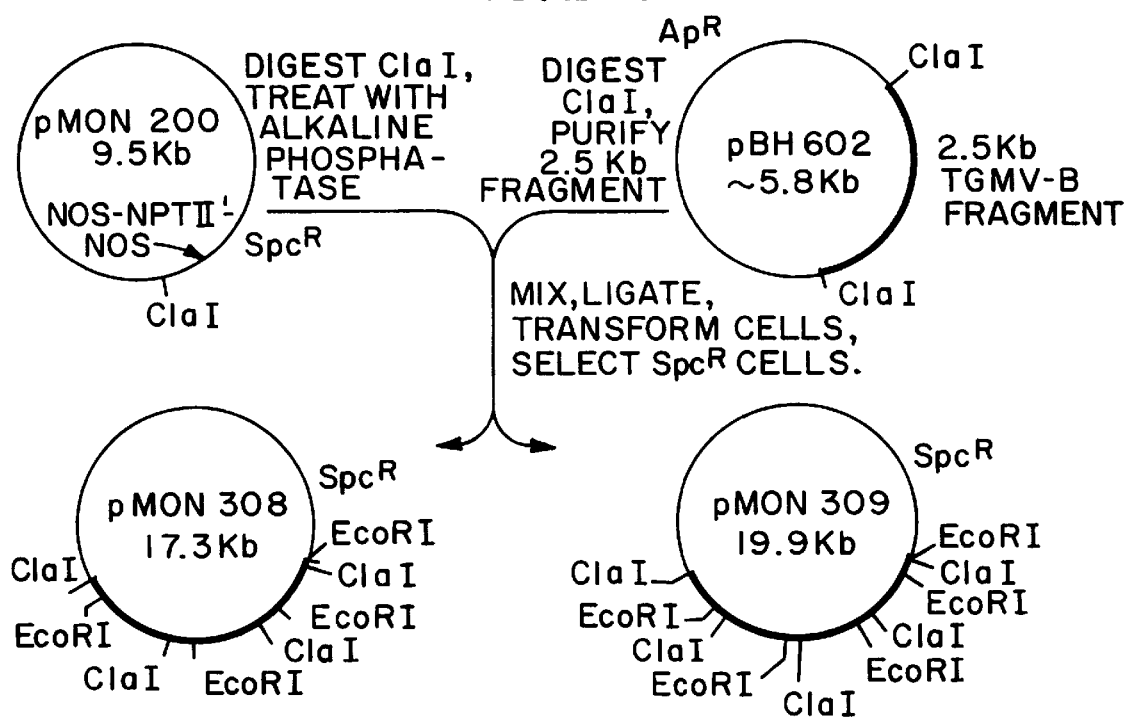
FIG. 2B depicts the construction of pMON308 and pMON309 comprising pMON200 having inserted therein at the ClaI restriction endonuclease site three or four copies of TGMV-B DNA, respectively. The blackened area represents TGMV-B DNA.

Resultant cointegrate plasmids comprising pMON200 carrying TGMV-A DNA were then mated into Agrobacterium and selected Agrobacterium carrying the resultant cointegrate plasmids were subsequently employed to insert the TGMV-A DNA into plant cells by conventional means. One of the resultant plasmids, pMON305, comprised pMON200 having two copies of the TGMV-A EcoRI fragment in direct repeats inserted in the EcoRI site of pMON200. *E. coli* strain MM294 carrying pMON305 has been deposited with the ATCC and has been given ATCC accession number 53304. A similar construct was made for the TGMV-B DNA which was obtained as a 2508 base pair (bp) ClaI insert in the ClaI site of pAT153 to yield pBH602 (Bisaro et al., 1982). DNA of pBH602 was cleaved with ClaI, the 2.5 kb fragment was purified and joined to pMON200 DNA that had also been cleaved with ClaI. One of the plasmids obtained carried three copies of the TGMV-B DNA ClaI fragment as direct repeats and was designated pMON308 (FIG. 2B). Another plasmid obtained carried four copies of the TGMV-B DNA ClaI fragment as direct repeats but in the opposite orientation of the inserts in pMON308. This plasmid was designated pMON309 (FIG. 2B).

The pMON305, 308 and 309 plasmids were introduced individually into separate *Agrobacterium tumefaciens* GV3111-SE cells using the tri-parental mating procedure described by Fraley et al.(1983, 1985) and the resulting Agrobacterium strains carrying the pMON305, pMON308 and pMON309 plasmids co-integrated into the resident, disarmed pTiB6S3-SE plasmid were each used separately in the leaf disc transformation procedure (Horsch et al., 1985) to obtain transformed regenerated petunia (*Petunia hybrida*) and tobacco (*Nicotiana benthamiana*) plants. Plants were regenerated in the presence of kanamycin as described previously (Horsch et al., 1985) and produced nopaline as expected for plants containing pMON200 derivatives. These plants, which contained integrated copies of either the two TGMV-A copies or three or four copies of the TGMV-B DNA, were normal in morphology.

The structure of the TGMV-A or -B DNAs in the transformed plants was determined by Southern hybridization analysis (Thomashow et al., 1980). As described more fully in the examples below, total DNA was prepared from leaves of the transformed petunia or infected tobacco plants and separated on agarose gels after cleavage with HindIII which does not cleave in either the TGMV-A or the TGMV-B DNA. The HindIII digestion was performed to reduce the size of the total leaf DNA to permit the entry of the DNA into the agarose gel. Any restriction endonuclease which does not cleave the A or B DNAs may, therefore, be employed.

Two duplicate gels were run for DNA separation. The separated DNAs were transferred to nitrocellulose filters and each filter was incubated separately with either radioactively-labelled TGMV-A specific cloned DNA (pMON349, FIG. 3), or TGMV-B specific cloned DNA (pMON350, FIG. 3). The construction of the pMON349 and pMON350 plasmids appears in FIGS. 3 and 5, and FIG. 3, respectively. As a positive control for the position of the various TGMV DNA forms, total DNA prepared from the leaves of TGMV virus-infected *N. benthamiana* plants was separated on the gels. For a negative control, total DNA from untreated petunia plant leaves was separated on the gels.

In the positive control, TGMV virus-infected *N. benthamiana* plants, both the TGMV-A and TGMV-B specific labelled DNAs hybridized to the total leaf DNA and showed the presence of three major intracellular forms (Hamilton et al., 1982) expected for the viral DNA (ss circles) and intra-cellular replicative forms (double-stranded nicked circles and covalently closed circles). It was then discovered that the total DNA prepared from the leaves of plants carrying pMON305, which contained tandem copies of the TGMV-A DNA, showed the same forms as the virus infected plants. These forms only contained TGMV-A sequences and no TGMV-B sequences. Leaf DNA prepared from a pMON308 plant did not show any free DNA forms. No hybridization with cloned TGMV-A or cloned TGMV-B DNA occurred with total leaf DNA from uninfected plants.

These results demonstrated that the TGMV-A DNA contains all of the functions necessary for replication and amplification of TGMV-A DNA sequences in plants and furthermore contains all of the functions necessary for the TGMV-A DNA to become free of its integrated position in the chromosome or T-DNA to give rise to single strand (ss) circlular DNA forms. These TGMV-A ssDNA forms can only arise as a result of TGMV-A DNA replication. It was thereby discovered that the TGMV-A DNA or the coat protein-encoding DNA of two genome (binary) geminiviruses have the capacity to replicate, in the absence of non-coat protein-encoding DNA sequences, in plants or plant cells. Furthermore, plants infected with only the TGMV-A component showed no symptoms of virus infection (e.g. disease symptoms).

Additional studies employing various cointegrate Ti plasmids carrying less than two complete tandem copies of the TGMV-A component revealed that plants regenerated from plant tissue transformed with these cointegrate plasmids similarly contained freely replicating TGMV-A DNA. These results indicated that plasmid DNA containing a coat protein-encoding geminivirus DNA, exemplified by TGMV-A DNA, can be created in plant cells from plant vector DNA and/or plant chromosomal DNA employing cointegrating and/or non-cointegrating (e.g. binary) plant vector constructs containing a coat protein-encoding geminivirus DNA flanked by directly repeating DNA segments which permit release (e.g. via recombination and/or replication) of plasmid DNA from the plant vector and/or plant chromosome.

It is anticipated that by employing the methods and compositions described herein, those skilled in the art can determine the optimal length and degree of nucleotide repetition of these directly repeating flanking DNA sequences. It is believed that such directly repeating flanking DNA sequences should comprise from about 50 to 600 base pairs in length, with a preferred length of about 250 to about 600 base pairs and a most preferred length of about 600 base pairs. In preferred embodiments, the degree of nucleotide repetition required in these directly repeating flanking DNA sequences is about 100 per cent, especially at lower nucleotide lengths. Additionally, such directly repeating flanking DNA sequences which permit the release of plasmid DNA from a given plant vector and/or plant chromosome can be derived from geminivirus DNA (see, for example, FIG. 31) or, alternatively, can comprise a heterologous DNA sequence.

As described more fully below, it was then determined that only a segment of the coat protein-encoding geminivirus DNA was required to permit autonomous replication of plasmid DNA in plant cells. Specifically, it was discovered that the DNA sequences coding for the geminivirus coat protein are not essential for autonomous replication of coat protein-encoding geminivirus DNA in plant cells. Thus, while geminivirus coat protein-encoding DNA lacking or interrupted in the coat protein coding sequence is able to replicate in plant cells, whole virus is not produced thereby likely preventing further transmission of viral DNA by insect vectors. Furthermore, it is anticipated that additional sequences or segments of the coat protein-encoding DNA not required for autonomous replication can now be determined by conventional mutagenesis and/or deletion experiments in accordance with the methods described herein.

Figure 31:
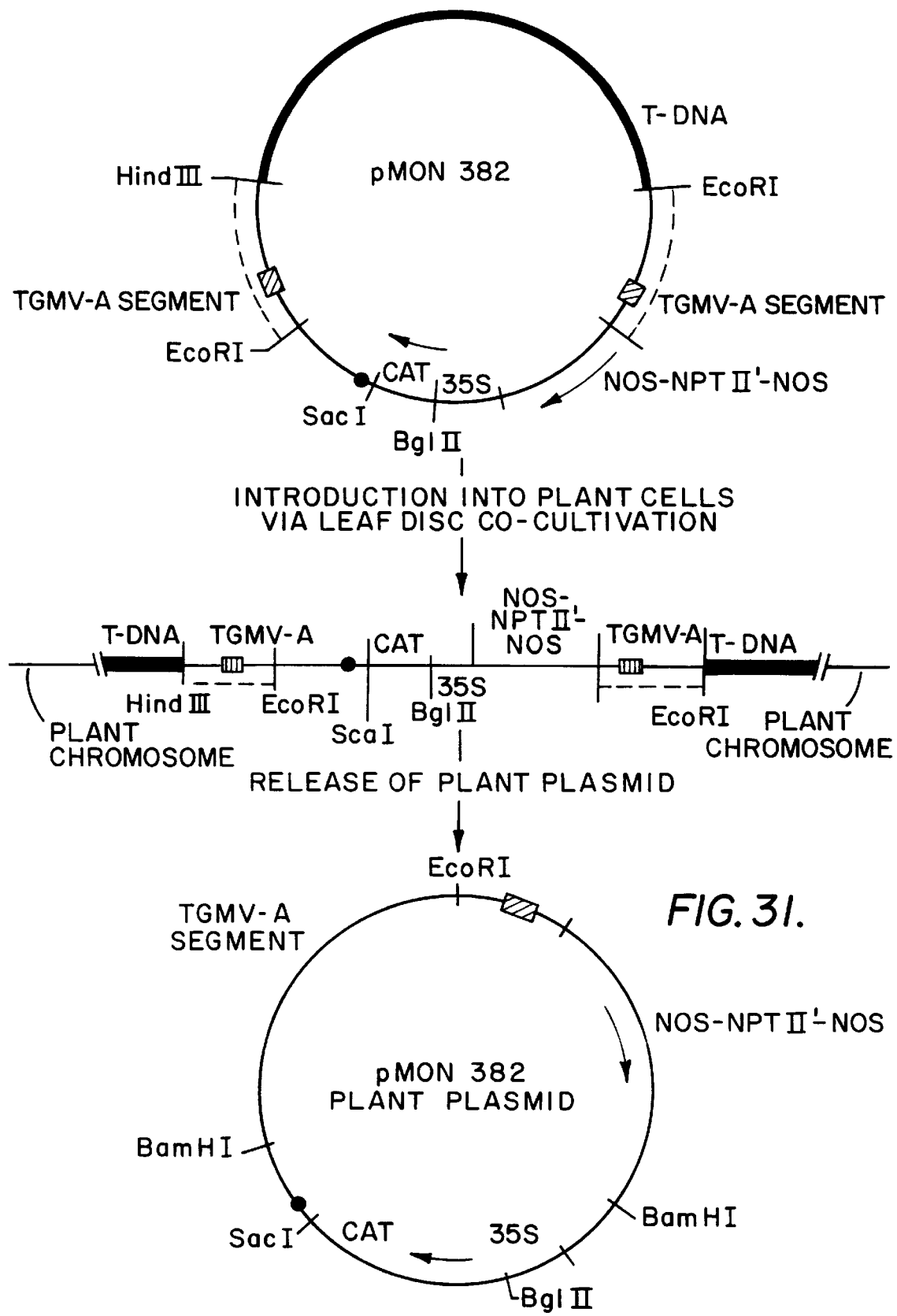
FIG. 31 depicts the production of a plant plasmid (pMON382 plant plasmid) in a plant cell genetically transformed with a plant vector (pMON382). The blackened line denotes *Agrobacterium tumefaciens* T-DNA (T-DNA), the hatched box denotes the TGMV common region, CAT denotes DNA sequences coding for chloramphenicol acetyl transferase, 35S denotes the CaMV 35S promoter sequence, NOS-NPTII'-NOS denotes the gene for kanamycin resistance, the darkened circle denotes the bidirectional TGMV-A DNA polyadenylation site and the broken line denotes directly repeating DNA sequences.

In accordance with the present invention, FIG. 31 presents a diagrammatic representation of the formation of a plant plasmid, shown as pMON382 plant plasmid, from a plant vector of the present invention, denoted pMON382, wherein the plant vector is constructed for, preferrably, a Ti plasmid delivery system. Although the diagrammatic representation shows the final plant plasmid as arising from a chromosomally integrated intermediate form of the plant vector DNA, the plant plasmid can alternatively arise (e.g. by recombination and/or replication) directly from the plant vector. Thus, while the diagrammatic plant vector is preferrably employed in a Ti plasmid based delivery system, the vector can alternatively be employed in conventional free DNA delivery systems. Additionally, the plant vector exemplified in FIG. 31 can be further modified for use in a free DNA delivery system by excising the T-DNA and transforming a plant cell with the remaining linear or recircularized vector fragment. Furthermore, as described more fully below, plant vectors useful in conventional free DNA delivery systems and permitting the formation of plant plasmid DNA can simply contain a DNA sequence and a segment of a coat protein-encoding geminivirus DNA which permits autonomous replication of plasmid DNA in a plant cell.

Construction of Geminivirus Replication and Expression Vectors

Having now demonstrated that the coat protein-encoding DNAs of binary geminiviruses, in particular, the TGMV-A component, are capable of autonomous replication in transformed plants, and, specifically, that these DNAs can generate autonomously replicating DNA from an integrated state in plant genomes, such coat protein-encoding geminivirus DNAs were modified so as to create vectors useful in Ti infections and/or free DNA delivery systems.

A primary characteristic of any vector is the presence of a site for insertion of a heterologous DNA sequence which site does not interfere with the ability of the vector to permit the replication of the heterologous DNA sequence in a host (e.g. plant) cell. Preferably, the plasmid vector should contain a restriction endonuclease site for insertion of a heterologous DNA sequence or gene desired to be replicated and/or expressed in plant cells. Such a restriction endonuclease site can be selected from existing sites in the geminivirus DNA, see, for example, FIG. 1, or may be introduced by conventional recombinant DNA techniques. Alternatively, the heterologous DNA sequence can be ligated (e.g. chemically) to the vector.

One of the criteria for selecting and/or altering existing sites and/or adding one or more restriction endonuclease sites is that such modifications and/or subsequent insertion of heterologous DNA sequences would not diminish the ability of the geminivirus DNA (e.g. coat protein-encoding DNA) to autonomously replicate in plant cells to an intolerable degree. This criteria can be established by, for example, assaying plants or plant cells transformed with the modified geminivirus DNA for the presence of geminivirus replicative forms (ss and/or ds circular DNAs) by the methods described below. Other selection criteria for useful restriction endonuclease sites include, but are not limited to, restriction sites which facilitate the insertion and/or subsequent manipulations of heterologous DNA sequences.

In one preferred embodiment of the present invention, an existing restriction endonuclease site, the ScaI site located within the DNA sequence coding for the TGMV coat protein (see FIG. 1) was selected and subsequently altered. As will be disclosed more fully below, it was thereby determined that the coat protein gene, which is required for encapsidation of the TGMV DNAs, can be eliminated or interrupted. Thus, the coat protein gene was demonstrated to represent a non-essential region for TGMV-A DNA replication in plants. These results also indicate that a full copy of a coat protein-encoding geminivirus DNA molecule, exemplified by TGMV-A DNA, is not essential for the generation in plants of plant plasmid molecules comprising geminivirus coat protein-encoding DNA.

Having now demonstrated that the coat protein gene sequences are not required for geminivirus-A DNA replication in plants, it is now possible to insert heterologous DNA sequences both shorter than the total number of bases coding for the geminivirus (e.g. TGMV) coat protein and/or at least as long as the coat protein gene sequence.

Indeed, as described more fully in the examples below, the DNA sequences coding for the geminivirus coat protein can be modified (e.g. interrupted and/or deleted) to carry and replicate a heterologous DNA insert. Additionally, in one embodiment, it was demonstrated that heterologous DNA sequences inserted into TGMV-A DNA can be longer than the DNA sequence encoding the TGMV coat protein. Hence, heterologous DNA sequences as small as a DNA segment carrying a restriction endonuclease site or multi-linker and at least as long as 4.3 kb (kilobases) can be replicated in plant cells as plasmid DNA employing the plant vectors of the present invention. Furthermore, as described more fully in the examples below, such heterologous DNA sequences are capable of being expressed in plant cells.

In one embodiment, a heterologous DNA sequence was inserted into the coat protein gene of TGMV-A DNA and, using an *Agrobacterium tumefaciens* intermediate Ti plasmid-based vector as the DNA delivery system into plant leaf cells, the heterologous DNA sequence was shown to replicate as part of freely (e.g. autonomously) replicating TGMV-A DNA in plants. As described more fully below, the geminivirus plant plasmid so produced in the transformed plant cells also contained a pUC18 origin of replication thereby enabling the plant plasmid vector to replicate in both plant and *E. coli* cells. This characteristic permits "rescue" of the released double-stranded circular forms by transformation of competent *E. coli* cells. Plasmids able to replicate in more than one host cell species (i.e. plant and bacterial cells) are often referred to as "shuttle vectors" and have the distinct advantage of affording both the rescue of the vector from one host cell species (e.g. plant cells) by another host cell species (e.g. bacteria) and allowing conventional recombinant DNA manipulations in such other hosts as bacteria.

In one preferred embodiment, the starting point for creation of a geminivirus vector was pMON505 (FIG. 4). pMON505 is an example of a binary Ti vector. An alternative geminivirus vector can be constructed employing other binary Ti vectors or a cointegrate Ti vector such as, but not limited to, pMON200 or pMON120 (Fraley et al. 1983). *E. coli* strain MM 294 carrying the Ti vector pMON505 as a plasmid DNA has been deposited with the ATCC and has been given ATCC accession number 53301.

Figure 4:
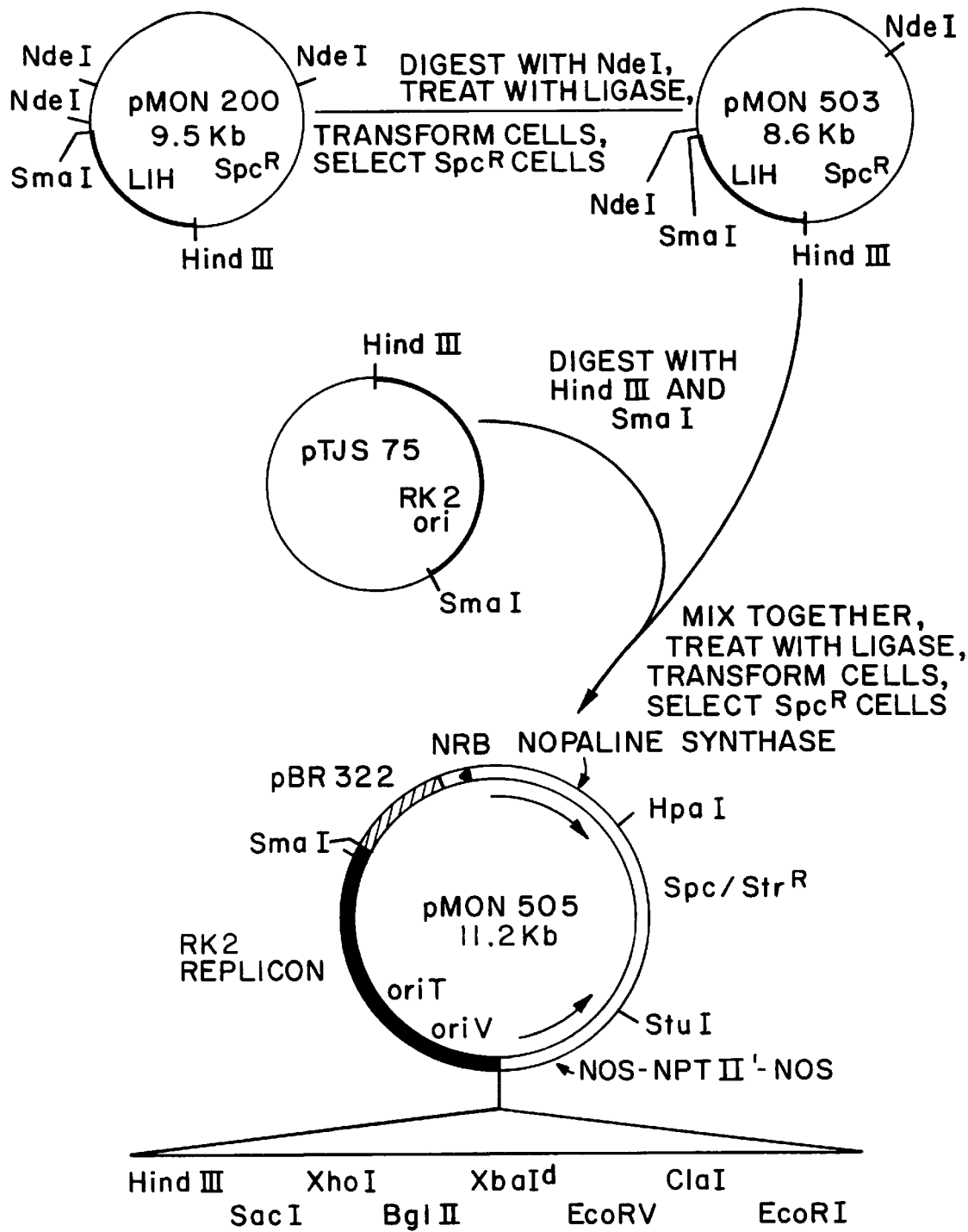
FIG. 4 depicts the construction of pMON505, a binary Ti plasmid vector, from pMON200, a cointegrate Ti plasmid vector. "NRB", shown as a blackened triangle denotes the nopaline T-DNA right border. RK2 shown as a blackened area denotes a bacterial origin of replication and origin for conjugational transfer wherein "oriT" denotes the origin of transfer and "oriV" denotes the origin of replication. The outset depicts the unique restriction endonuclease cleavage sites contained within pMON505 at the designated site. Spc/Str$^R$ denotes a spectinomycin/streptomycin resistance gene.

The pMON505 plasmid is a "binary vector" (Hoekema et al., 1983; Bevan, 1984) derivative of pMON200 (Fraley et al., 1985) in which the DNA segment (LIH) that provides homology with a Ti plasmid resident in Agrobacterium has been replaced with a small, 3.8 kb segment of an RK2 broad host range plasmid (RK2 replicon, FIG. 4). This replacement results in a Ti plasmid-based vector able to replicate in Agrobacterium cells thus obviating the need for recombination between the Ti vector and a resident Ti plasmid. As shown in FIG. 4, a portion of the homology region was deleted from pMON200 by partial digestion with NdeI and religation. Next, the 3.8 kb RK2 DNA segment (RK2 Replicon) was isolated from pTJS75 (Schmidhauser and Helinski, 1985) after cleavage with HindIII and SmaI and joined to the 7.4 kb fragment of pMON503 to yield pMON505. pMON505 (FIG. 4) carries a pBR322 origin of replication, the RK2 origin of replication and origin for conjugational transfer, a synthetic multilinker containing unique cleavage sites for EcoRI, ClaI, EcoRV, XbaI, BglII, XhoI, SacI and HindIII, the NOS-NPTII'-NOS chimeric gene for kanamycin resistance in plant cells, a bacterial spectinomycin/streptomycin resistance marker gene ($Spc^R$/$Str^R$) for the selection of pMON505 plasmid DNA in both *E. coli* and *A. tumefaciens*, an intact nopaline synthase gene and a single nopaline-type T-DNA right border sequence (NRB).

Figure 5:
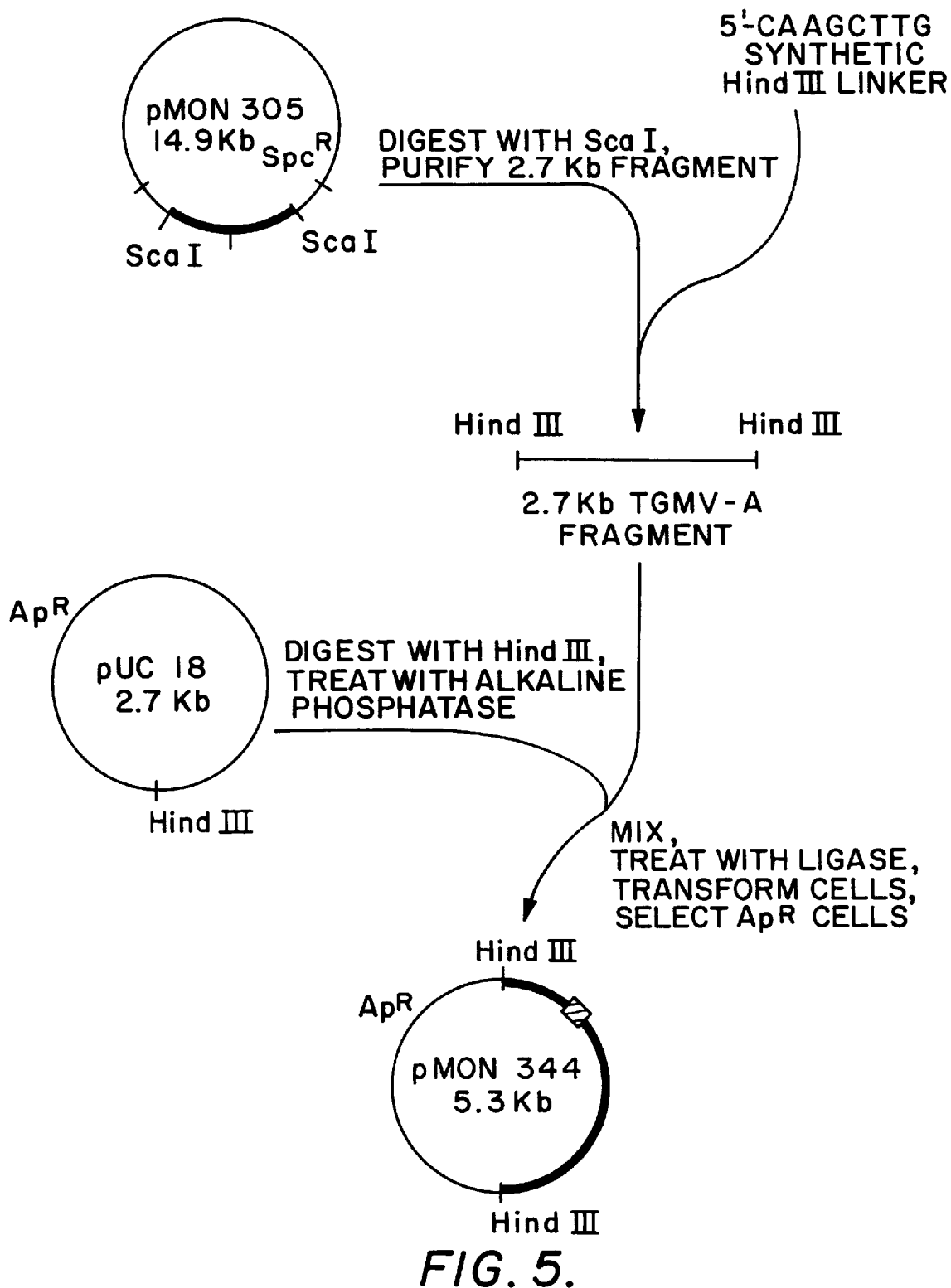
FIG. 5 depicts the construction of pMON344 comprising a pUC18 plasmid having inserted therein at the HindIII site the 2.6 kb ScaI fragment isolated from pMON305. The hatched box denotes the TGMV common region.
Figure 6:
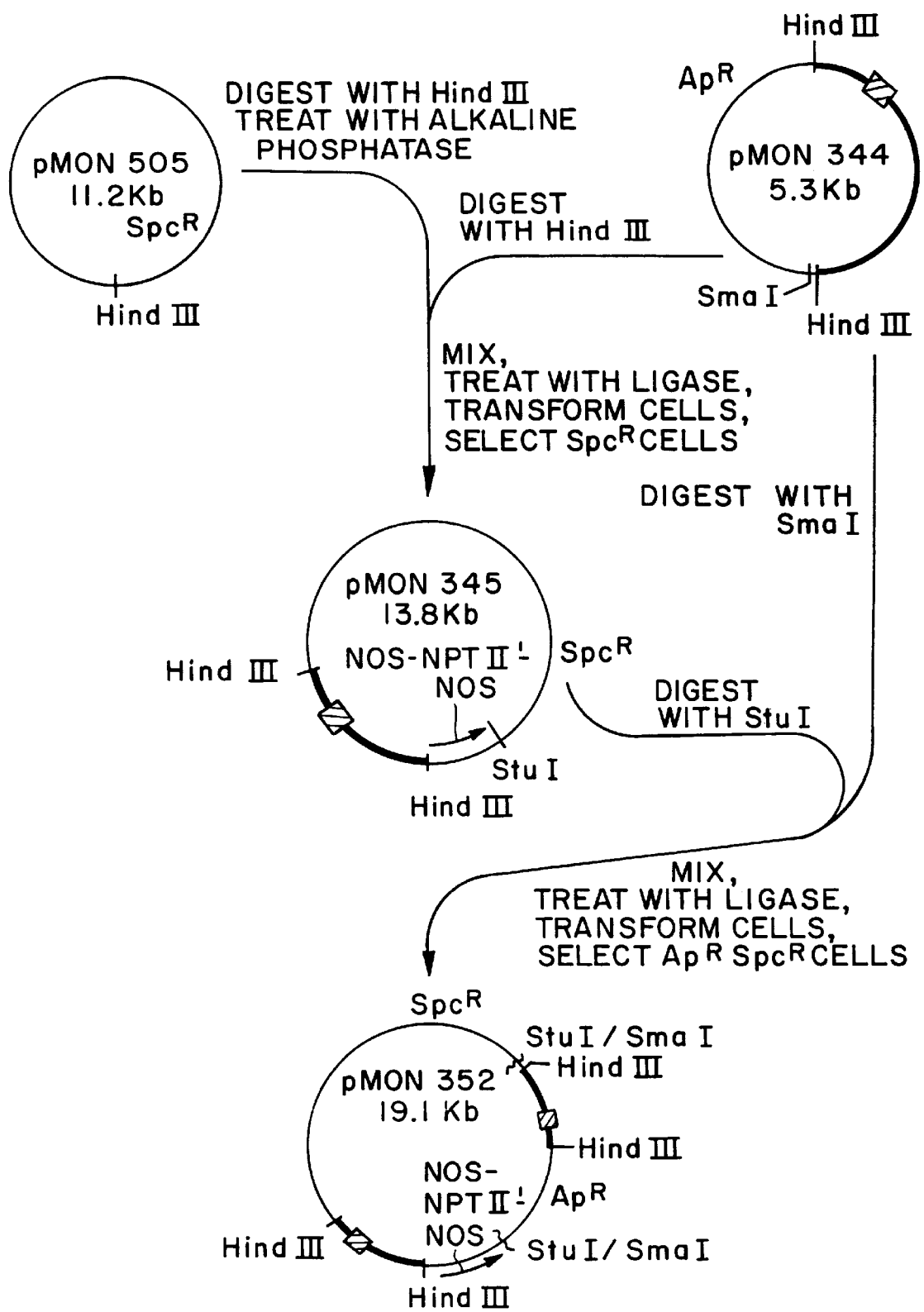
FIG. 6 depicts the construction of pMON352 which carries a dimer of TGMV-A DNA as directly repeating DNA sequences. TGMV-A DNA sequences are shown as blackened areas and the hatched box denotes the TGMV common region.

As shown in FIG. 5, to introduce an easily used, unique restriction site into the coat protein coding sequence, pMON305 DNA (FIG. 2A) was cleaved with ScaI which cleaves the TGMV-A DNA once in the coat protein coding sequence at base pair (bp) 791. This released a 2.6 kb ScaI fragment containing a complete TGMV-A DNA which was ligated to a synthetic HindIII linker (5'-CAAGCTTG, New England Biolabs, Beverly, Mass.). Following digestion with HindIII, the 2.6 kb HindIII linear fragment was introduced into pUC18 (Yanisch-Perron et al., 1985) (New England Biolabs, Beverly, Mass.) that had been previously cleaved with HindIII. The resulting plasmid was called pMON344 (FIG. 5). The 2.6 kb TGMV-A HindIII fragment was then purified from HindIII digested pMON344 and introduced into the HindIII site of pMON505. The resulting binary vector, pMON345, is shown in FIG. 6.

Figure 7:
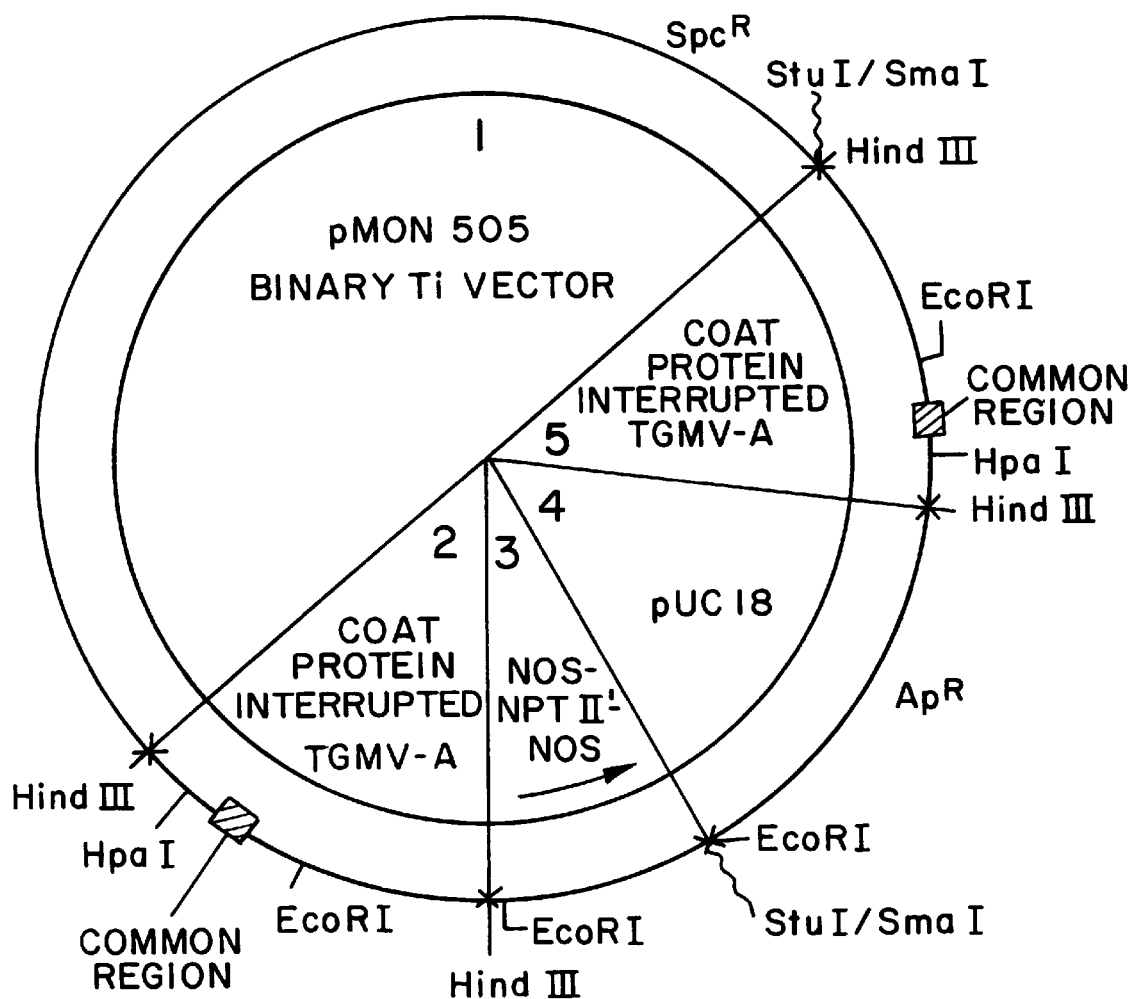
FIG. 7 depicts pMON352 wherein the relevant DNA coding sequences are identified as labeled thereon.

The pMON345 binary vector contains a unique StuI site located 142 bp beyond the 3' end of the NOS-NPTII'-NOS kanamycin resistance gene. pMON344 contains a unique SmaI site located in the pUC18 synthetic multilinker. DNA of pMON344 was cleaved with SmaI and mixed with pMON345 DNA cleaved with StuI and treated with DNA ligase. After transformation of cells and screening for a recombinant plasmid with the correct orientation (e.g. directly repeating) of the two TGMV-A components, plasmid pMON352 (FIGS. 6 and 7) was isolated. As shown in FIG. 7, plasmid pMON352 is a binary vector comprised of the following DNA segments:

a) A pMON505 "binary" type, Ti plasmid-based plant transformation vector (1).

b) One copy of the TGMV-A DNA cloned as a linear insert interrupted in the coat protein coding sequence (2).

c) The chimeric NOS-NPTII'-NOS kanamycin resistance gene for selection of transformed plant cells (3).

d) One copy of the *E. coli* pUC18 multicopy plasmid cloning vector (4).

e) A second copy of the TGMV-A DNA also cloned as a linear insert interrupted in the coat protein coding sequence (5). This copy is a direct repeat of the first TGMV-A DNA insert.

Plasmid pMON352 exemplifies one type of geminivirus plant vector useful in replicating and/or expressing heterologous DNA in plants. It is anticipated that geminivirus vectors of the pMON352-type can be introduced into plants by any conventional delivery method. It is further anticipated that various modifications or variants, made by conventional techniques, can be made in the pMON352 vector to yield equivalent geminivirus vectors useful in replicating and/or expressing heterologous DNA in plants or plant cells. Such modifications can include, but are not limited to, replacement and/or addition of an alternative marker gene, deletion and/or replacement of the pUC18 sequences with an alternative rescue DNA sequence as determined by the host (i.e. bacterial or yeast) chosen for rescue purposes, replacement of the TGMV-A DNA sequences with other, functionally, equivalent binary geminivirus coat protein-encoding DNA sequences, deletion of the pMON505 DNA sequences, and replacement of the pMON505 DNA sequences with cointegrate Ti vector DNA sequences. A geminivirus vector comprising a preferred variant of pMON352 is pMON382 described more fully below.

In one preferred embodiment, pMON352 was introduced into plant cells employing a Ti vector delivery system. Specifically, pMON352 was introduced into *Agrobacterium tumefaciens* cells containing pTiB6S3-SE plasmid using the tri-parental mating procedure described by Fraley et al. (1983, 1985). The resultant *Agrobacterium tumefaciens* cells carrying the pMON352 plasmid were then used to introduce the pMON352 sequences into plant cells using the leaf disc procedure (Horsch et al., 1985). pMON352 may alternatively be employed as a geminivirus plant plasmid vector for use in free DNA without modification or by such modifications as would remove the pMON505 DNA sequences.

The pMON352 DNA introduced into plant cells are incorporated into the genomes of the host cells and can become integrated into the chromosomes of the plant cell hosts. Thus, as previously discussed, freely replicating TGMV-A DNA forms comprising TGMV-A DNA interrupted in the coat protein gene and/or TGMV-A DNA having inserted therein at the HindIII site in the coat protein gene heterologous DNA sequences comprising NOS-NPTII'-NOS DNA and a pUC18 DNA, can arise through recombination between TGMV-A DNA sequences contained in non-integrated pMON352 DNA molecules and/or by recombination between non-integrated and chromosomally integrated TGMV-A DNA sequences and/or by direct replication of non-integrated or chromosomal copies of TGMV-A DNA.

By employing the analytical methods previously described for demonstrating the autonomous or independent replication of TGMV-A DNA in transformed plants, it was discovered that TGMV-A DNA interrupted in the DNA sequence coding for the TGMV coat protein was similarly able to freely (e.g. autonomously) replicate in transformed plant cells (e.g. leaf disc tissue). Specifically, extrachromosomal or plasmid DNA forms of pMON352 were identified by isolating DNA from pMON352 transformed leaf tissue, separating the forms by agarose gel electrophoresis, transferring to nitrocellulose, hybridizing the DNA with a radioactively labelled TGMV-A DNA or pUC18 specific probe and exposing the filter to x-ray film. The ability to select transformed leaf disc tissue on medium containing kanamycin demonstrates the ability of the geminivirus vector to allow expression of the kanamycin resistance (e.g. NOS-NPTII'-NOS) gene in plant cells. Additionally, the ss DNA and ds DNA forms detected were of a size consistent with the pMON358 structure shown in FIG. 8 (e.g. about 7.0 kb). Thus, these results demonstrate that a functional coat protein gene is not essential for the generation of freely replicating (e.g. plasmid) binary geminivirus coat protein-encoding DNA (e.g. TGMV-A DNA). These results further demonstrate that heterologous DNA can be successfully inserted into a geminivirus coat protein gene and thereafter replicated and expressed in plant cells as part of plasmid (e.g. extrachromosomal) DNA molecules comprising merely a segment of a coat protein-encoding DNA geminivirus. Additionally, such heterologous DNA can be of a size (e.g. base-pair number) greater than a geminivirus coat protein gene. Thus, in one embodiment of the present invention, pMON352 exemplifies one type of vector capable of allowing both replication and expression of heterologous DNA sequences in plants. Although the present embodiment employs a Ti plasmid-based delivery system into plant cells, it is anticipated herein that such binary geminivirus vectors as exemplified by pMON352 or variants thereof (i.e. pMON358, FIG. 8) can alternatively be employed in conventional free DNA delivery systems.

In another embodiment of the present invention, alternative vectors were constructed for use in free DNA delivery systems. Free DNA delivery systems afford the possibility of directly inserting plasmid DNA molecules into the genomes of plant cells. Such vectors can be particularly useful in transforming plant suspension cell cultures thereby providing an economic means for replicating and/or expressing heterologous DNA products.

Vectors for free DNA delivery systems which comprise plasmid DNA molecules typically contain a heterologous DNA sequence and a segment of a coat protein-encoding geminivirus DNA which segment permits autonomous replication of the plasmid DNA in a plant cell. As previously stated, the heterologous DNA sequence typically contains a gene for the polypeptide desired to be replicated and expressed in the transformed plant cell and, preferably, a marker for selection and/or identification of transformed plant cells. The segment of a coat protein-encoding geminivirus DNA minimally contains those DNA sequences which are essential for the replication of the plasmid DNA in a plant cell. An example of such a coat protein-encoding geminivirus DNA segment is an entire coat protein-encoding geminivirus DNA molecule excluding the DNA sequences coding for the geminivirus coat protein. Additionally, while applicants do not wish to be bound by the following theory of mechanism, it is believed that the geminivirus common region serves as an origin of replication. As such, the common region is a required component of the segment of a coat protein-encoding geminivirus DNA contained within the plasmid DNA molecules employed to either directly transform plant cells or which result from transformation of plants or plant cells with vectors which produce a plasmid DNA in a plant cell.

Figure 8:
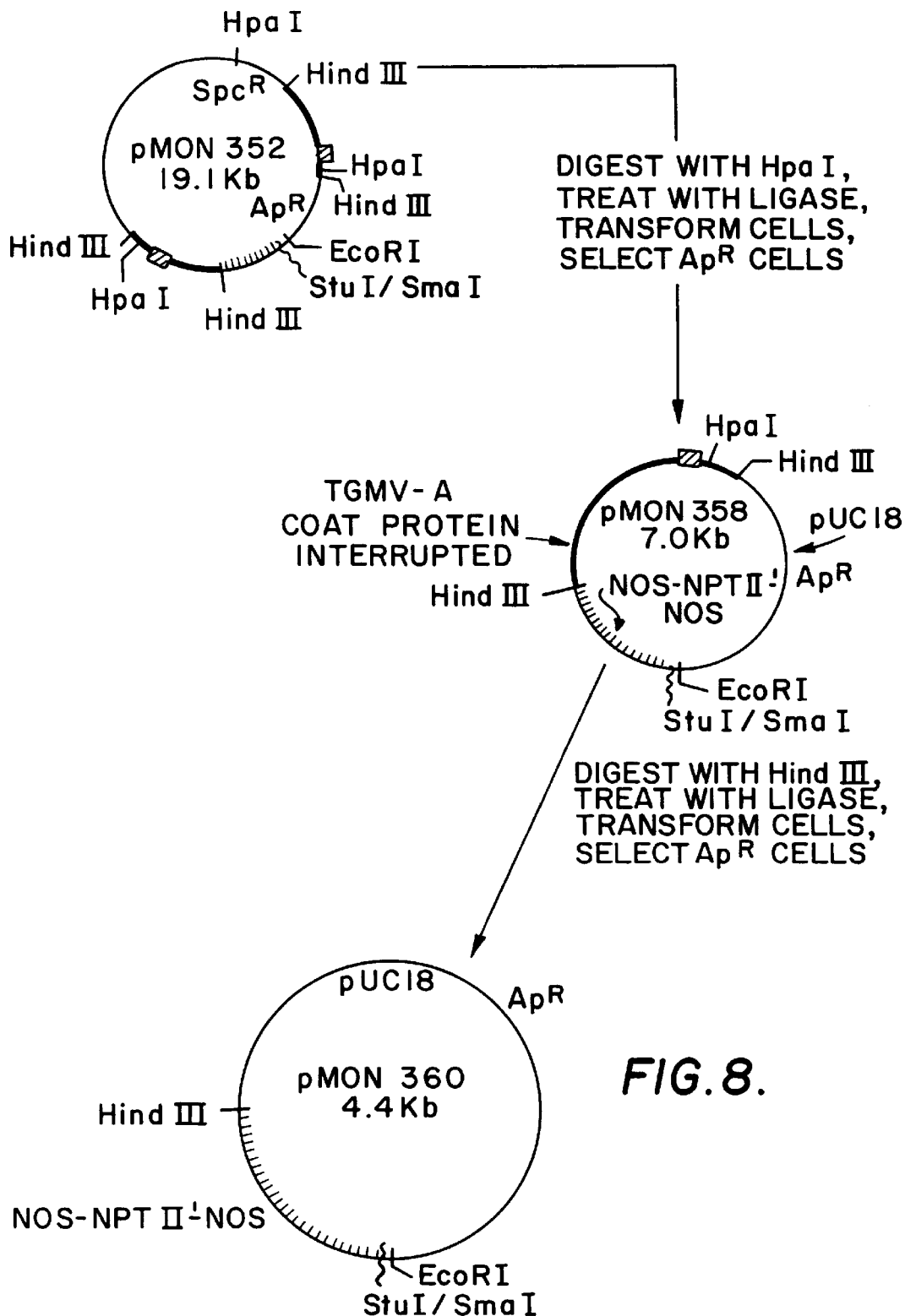
FIG. 8 depicts the construction of pMON360 from pMON352. The blackened line denotes TGMV-A DNA sequences, the hatched box denotes the TGMV common region and the stippled line denotes the kanamycin resistance gene (NOS-NPTII'-NOS).

In one preferred embodiment of the present invention, a vector for use in free DNA delivery systems was constructed, briefly, as follows. As shown in FIG. 8, pMON352 DNA was digested with HpaI to remove the pMON505 derived Ti plasmid DNA, rejoined with DNA ligase, and thereafter employed to transform a bacterial host cell. After transformation of the bacterial host cell, one plasmid was isolated and named pMON358 (FIG. 8).

The pMON358 plasmid can thereafter be introduced into plant protoplasts as free DNA using such conventional methods as polyethylene glycol, calcium phosphate, poly-L-ornithine (Marton et al., 1979; Freeman et al., 1984), micro-injection (Griesbach, 1983) or electroporation (Potrykus et al., 1985; Fromm et al., 1985). Plant protoplasts so transformed can then be analyzed for the presence of freely replicating pMON358 DNA forms employing the previously described TGMV-A DNA or pUC18 DNA probe-specific methods. As a control plasmid that should not be capable of autonomous replication in plant protoplasts a further derivative of pMON358 was created. Specifically, DNA of pMON358 was digested with HindIII, which releases the TGMV-A DNA, treated with DNA ligase and used to transform bacterial cells. One of these derivatives, deleted for the TGMV-A DNA, was isolated and called pMON360 (FIG. 8).

Purified DNA of pMON358 or pMON360 can then be mixed with $3\times10^6$ protoplasts derived from either petunia or carrot (*Daucus carota*) suspension cells and subjected to a high voltage. The treated protoplasts can then be diluted into growth medium and incubated at 25° C. for 48–72 hours. At this time, DNA would be prepared from the protoplasts and subjected to Southern blot analysis as described above using the TGMV-A specific pMON349 (FIG. 3) or pUC18 DNA (FIG. 5) as the radioactively labelled probe.

Replication of pMON358 DNA in the transformed protoplasts should give rise to single-stranded circular DNA characteristic of replicating TGMV-A DNA whereas the pMON360, lacking TGMV-A DNA would not. The single-stranded DNA form would be the size expected for the pMON358 DNA (about 7 kb).

As shown in FIG. 8, the pMON358 plant plasmid contains a pUC18 DNA sequence. This pUC18 sequence contains a bacterial origin of replication (e.g.replicon) thereby affording rescue and further manipulations of the pMON358 plasmid in such bacterial hosts as *E. coli*. As with all shuttle vectors described herein, it is anticipated that DNA sequences containing a yeast cell origin of replication such as one operable in *Saccharomyces cerevisiae* can be alternatively or additionally inserted into the plasmid and/or vector DNAs described herein to permit rescue and further manipulations in a yeast cell host.

Having demonstrated that coat protein-encoding geminivirus DNA can be successfully employed to replicate a heterologous DNA sequence in plants, additional novel plant expression vectors employing said geminivirus DNA can now be created. The novel expression vectors of the present invention will be useful in producing a desired chemical product in both plant cells and plants. The desired chemical products so produced can then be recovered by such conventional methods as affinity chromatography and/or conventional methods as determined by the site (e.g. plant cell or plant tissue) of production.

An expression vector should contain all the DNA sequences necessary for both replication and expression of a heterologous DNA sequence in a given host along with a marker for identification or selection of hosts transformed with said expression vector. In some instances, the heterologous products coded for by the heterologous DNA sequence can function as a marker for identification and/or selection of transformed host cells. In the event that a transformation marker other than the heterologous DNA gene product or chemical, compound or polypeptide caused to be synthesized by the heterologous DNA gene product is desired, such conventional markers as antibiotic resistance can be employed.

Expression of a heterologous DNA coding sequence in plants has been shown to require the following components:

a promoter sequence operable in plant cells, a transcriptional start or leader sequence (e.g. 5' non-translated region found in messenger RNA) which is typically contained adjacent to and within the promoter sequence, a DNA sequence coding for translation start-signal codon, a DNA sequence coding for the desired (e.g. heterologous) polypeptide product, at least one DNA triplet coding for a translation terminator codon, and a DNA sequence coding for a 3' non-translated region containing a polyadenylation signal.

As previously stated, any promoter operable in plant cells can be employed. An operable promoter is understood to mean a DNA sequence able to allow transcription of a given DNA sequence in a cell. Such promoters include, without limitation, the cauliflower mosaic virus (CaMV) 35S promoter, the CaMV 19S promoter, the NOS promoter and the promoter from genes encoding the small subunits of RuBP carboxylase from pea, petunia, soybean and tobacco wherein the preferred promoter is the CaMV 35S promoter. Additionally, as described more fully in the examples below, it was herein discovered that the TGMV coat protein promoter is effective for allowing expression of heterologous DNA sequences in plants. Similarly, any DNA sequence coding for 5' non-translated regions found in any eucaryotic cell preferably plant cell MRNA molecules or plant virus MRNA molecules, can be employed. Examples of DNA triplets coding for translation termination codons functional in plant cells include TAA, TAG and TGA. As in the case of DNA promoter sequences, any DNA sequence coding for a polyadenylation sequence operable in plant cells can be employed. Such DNA sequences include, without limitation, sequences from CaMV, geminivirus and from expressed or expressable plant cell genes, wherein the preferred sequences are obtained from NOS or the TGMV coat protein gene.

Typically, the heterologous DNA coding sequence is isolated from a genomic library, cDNA library or cells expressing the desired heterologous gene product by conventional means or is chemically synthesized. Such isolated or chemically synthesized heterologous DNA sequences typically contain translation start-signal and translation termination sequences. The term "expression cassette" as used herein means a DNA molecule or sequence which contains all the information required for expression of a heterologous DNA coding sequence in a host except the heterologous DNA coding sequence itself and the DNA sequences encoding the translation start-signal codon and translation termination codon, as the DNA sequences coding for the translation start-signal codon and translation termination codon are typically contained within the heterologous DNA coding sequence.

In one preferred embodiment, pMON382 (FIG. 18), in which the chloramphenicol acetyl transferase (CAT) DNA coding sequences are deleted would exemplify a vector containing such an expression cassette.

Typically, an eucaryotic expression vector is first assembled in easily manipulated and well developed host-vector systems such as bacteria or yeast. For example, a yeast or bacterial cloning vector with a known sequence, previously identified restriction endonuclease sites and known host is chosen. Such a host-vector system provides a means by which the components required for expression of a heterologous DNA coding sequence in plants can be assembled. An expression cassette can be inserted in the bacterial or yeast vector in total and/or can be inserted in a step-by-step assembly process employing conventional recombinant DNA tecniques.

Figure 9:
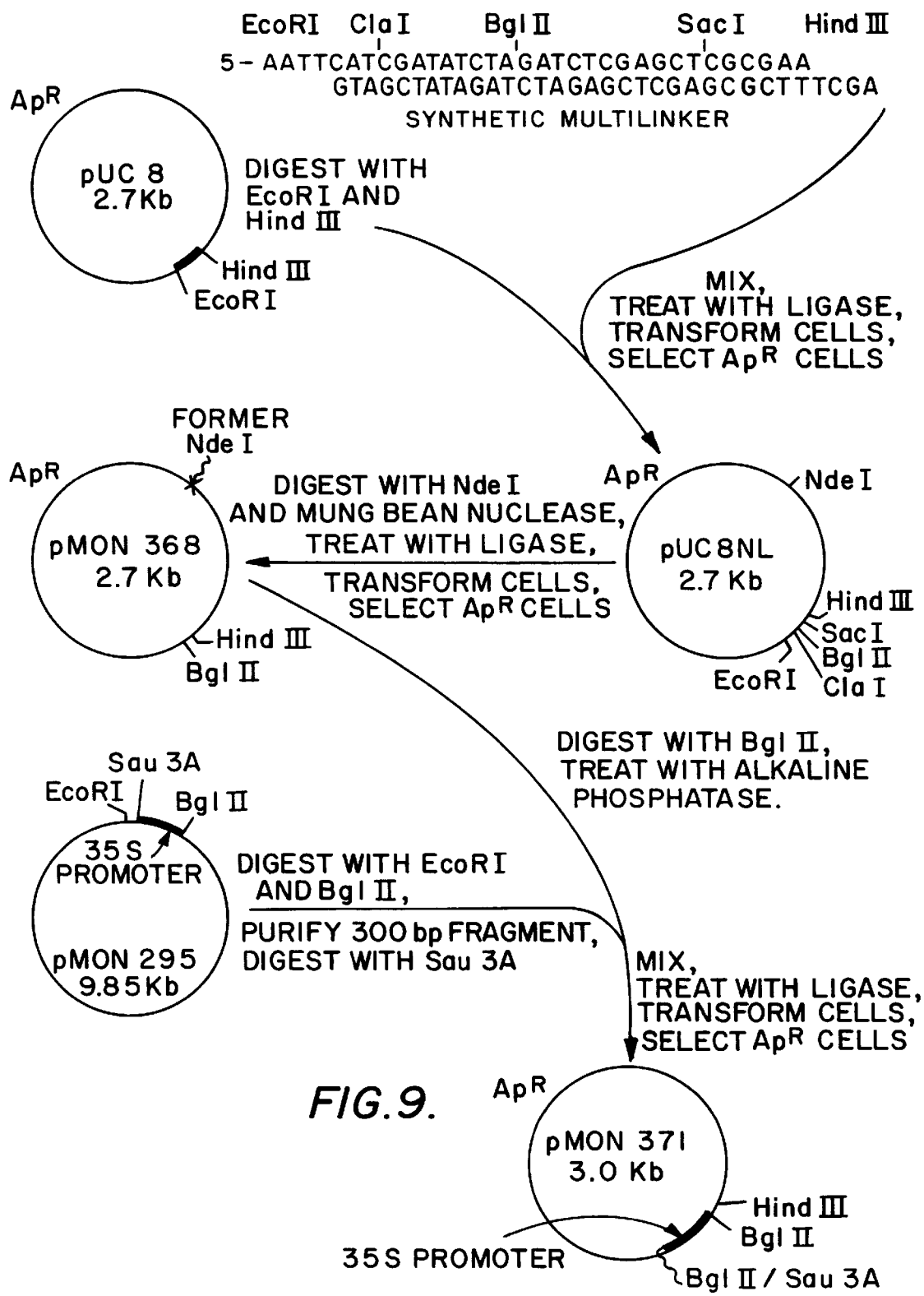
FIG. 9 depicts the construction of pMON371 which comprises a pUC8 plasmid modified to contain a unique BglII restriction endonuclease site into which site the CaMV 35S promoter has been inserted.

In one preferred embodiment of the present invention, a pUC8 plasmid (New England Biolabs, Beverly, Mass.) was chosen as a convenience in obtaining large amounts of the various intermediates in the construction. Specifically, as shown in FIG. 9, the pUC8 DNA was modified by replacement of the multi-linker contained between the EcoRI and HindIII sites with a new multilinker, also bounded by EcoRI and HindIII sites, consisting of the following sequence:

```
RcoRI    ClaI       BglII  SacI         HindIII
5'-GAATTCATCGATATCTAGATCTCGAGCTCGCGAAAGCTT-3'
```

Any similar such linker containing one or more restriction endonuclease cleavage sites can be employed which would provide for the ordered assembly of the desired DNA sequence or gene and/or expression components to be carried on the chosen geminivirus plasmid vector DNA for expression in plants.

The above, preferred, linker contains convenient restriction endonuclease sites (EcoRI, ClaI, BglII, SacI and HindIII) for use in assembling the plant plasmid vector from its component parts. The modified pUC8 cloning vehicle was called pUC8NL (FIG. 9). A further modification of the pUC8NL was made by deleting the single NdeI site that occurs at base pair 183 of the pUC8 sequence (Yanisch-Perron et al., 1985) by treatment of the plasmid with NdeI, mungbean nuclease and re-joining with ligase. The resultant plasmid shown in FIG. 9, was called pMON368.

In one preferred embodiment, the Cauliflower Mosaic Virus (CaMV) 35S promoter which encodes both the promoter and transcription start-signal sequence was chosen. Other promoters operable in plants or plant cells can be employed and are known to those skilled in the art. The CaMV 35S promoter carried on a 300 base pair Sau3A-BglII fragment was purified from pMON295 (FIG. 9) and introduced into the BglII site of the pMON368 such that the BglII site nearest to the HindIII site end of the linker was recreated. As shown in FIG. 9, the resultant plasmid was called pMON371. *E. coli* strain MM 294 carrying the pMON295 plasmid has been deposited with the ATCC and given ATCC accession number 53303.

Figure 10:
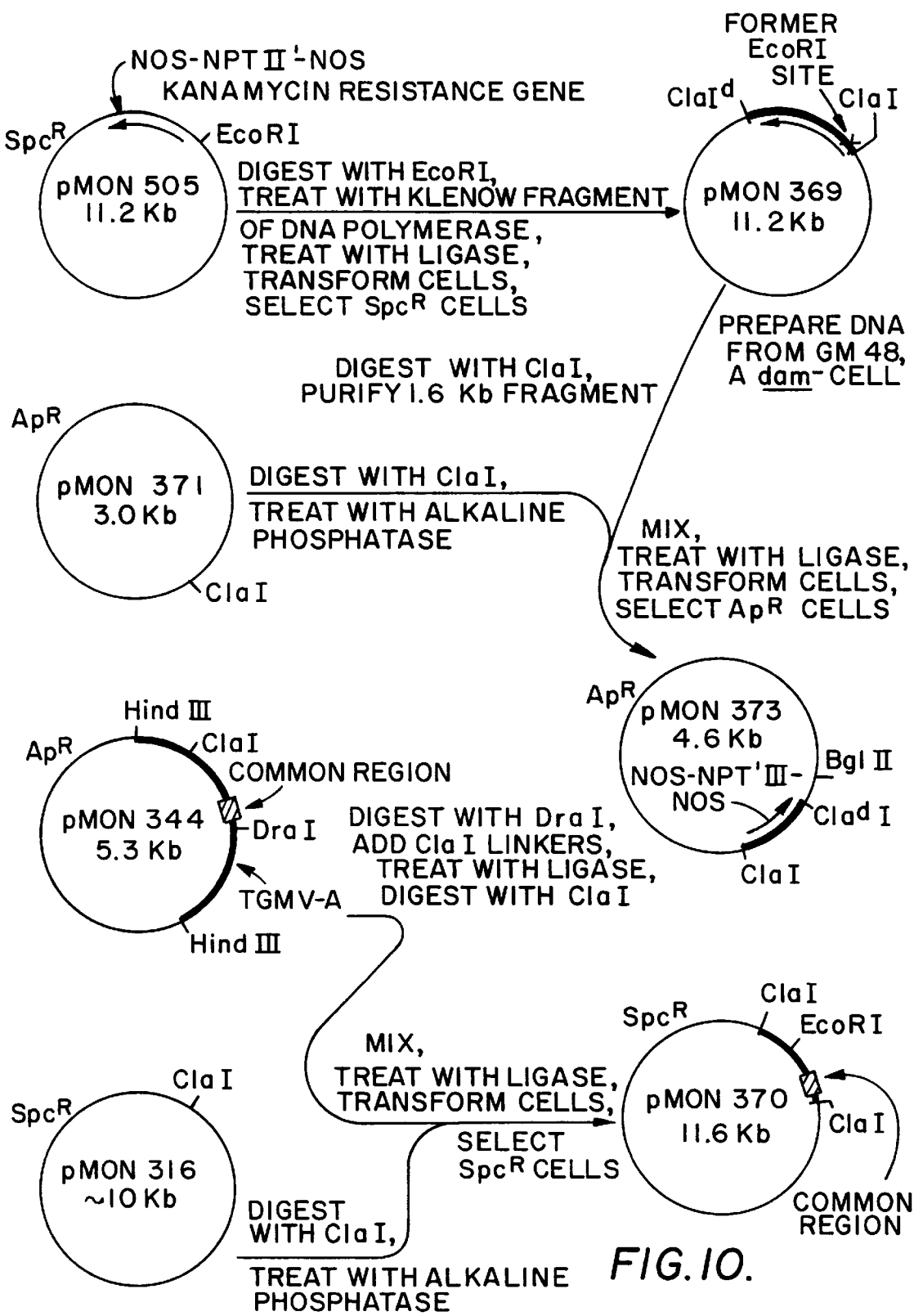
FIG. 10 depicts the construction of pMON373 and pMON370. The blackened area on pMON370 denotes TGMV-A DNA and the hatched box denotes the TGMV common region.

Next, a selectable marker functional in plants and/or plant cells was added. In one preferred embodiment, kanamycin resistance was chosen and was constructed as follows. The nopaline synthase promoter was joined to the modified bacterial Tn5 neomycin phosphotransferase (NOS-NPTII'-NOS) coding sequence (from which the extra AUG translational initiator signal was removed) and followed by the nopaline synthase 3' nontranslated sequences previously described (Fraley et al. 1983). This marker gene is carried on a 1.6 kb ClaI fragment obtained from pMON369 (FIG. 10), a derivative of pMON505, that had been treated with EcoRI and the Klenow fragment of DNA polymerase to remove the EcoRI site. The 1.6 kb ClaI fragment, isolated from pMON369 DNA prepared in a DNA adenine methylase deficient strain of *E. coli*, was introduced into the unique ClaI site of pMON371 to yield pMON373 (FIG. 10). Since the cleavage of the ClaI site at the 3' end of the marker gene is prevented by methylation of the overlapping 5'- GATC sequence in DNA prepared from DNA adenine methylase proficient strains of *E. coli*, pMON373 DNA prepared from such a strain contains a unique, cleavable ClaI site.

Figure 11:
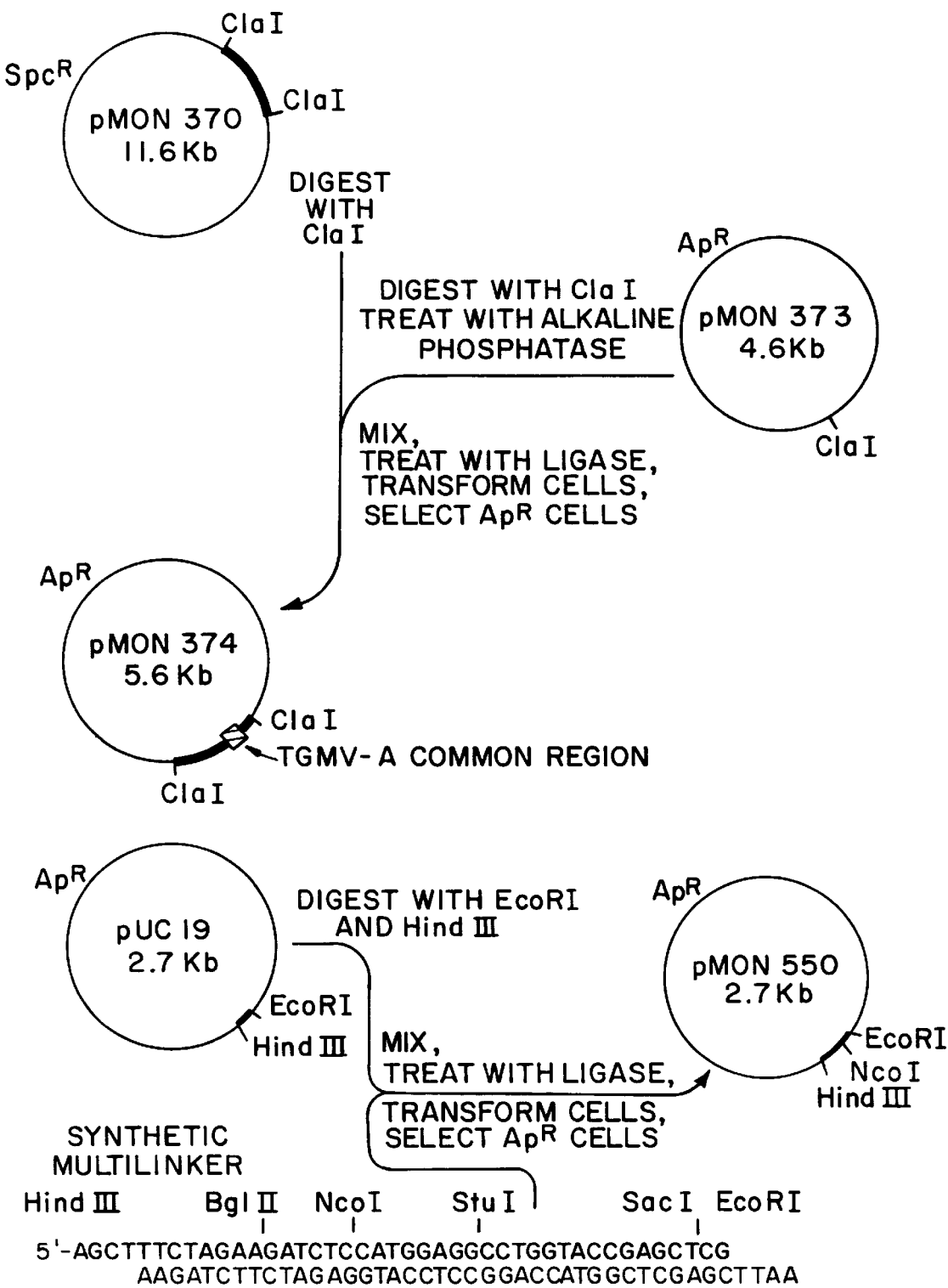
FIG. 11 depicts the construction of pMON374 comprising pMON373 having inserted therein at the ClaI site a 1 Kb fragment of TGMV-A DNA carried on a ClaI fragment isolated from pMON370. This figure also depicts the construction of pMON550 comprising pUC19 modified by the insertion of a synthetic multilinker in place of the pUC19 EcoRI-HindIII fragment. The blackened area on pMON550 denotes the synthetic multilinker.

A portion of the TGMV-A DNA from the ClaI site at base pair 1814 and extending through the common region to the AhaIII (DraI) site at base pair 259 was inserted into the single, cleavable ClaI site of pMON373. The DraI end of the TGMV-A DNA segment had been modified by addition of a synthetic ClaI linker (New England Biolabs, Beverly, Mass., 5'-CATCGATG) to permit insertion into the ClaI site of pMON373. The resultant plasmid was called pMON374 (FIG. 11).

Next, a heterologous DNA coding sequence was inserted. Any heterologous DNA sequence isolated by conventional techniques from biological material or chemically synthesized encoding a desired (e.g. heterologous) chemical product, protein, or fragment thereof can be employed. Examples of such heterologous DNA coding sequences are well known and available to those skilled in the art and include, but are not limited to the heterologous chemical products previously enumerated.

In one preferred embodiment, a DNA sequence encoding E. coli chloramphenicol acetyl transferase (CAT) was selected for insertion into the geminivirus vector of the present invention. As known to those skilled in the art, the CAT coding sequence can be isolated from E. coli plasmid pBR325 (available from Bethesda Research Laboratories, Inc., Gaithersburg, Md.) or chemically synthesized. The CAT protein was chosen as it can readily be assayed and accurately quantified in small amounts of plant tissue or plant cells. Enzyme activity can be detected in as little as $3 \times 10^6$ plant protoplasts (Fromm et al., 1985). Any other foreign gene that makes a protein that is detectable in plant extracts by such means as radio-immune assay or enzymatic assay can alternatively be incorporated into the plasmid for expression purposes. Examples of such proteins include, but are not limited to, the alpha subunit of human chorionic gonadotropin, growth hormone, tissue plasminogen activator, insulin-like growth factors, atrial peptides, useful enzymes, previously enumerated chemical products and the neomycin phosphotransferase II enzyme which was also carried in the plasmid as a selectable marker.

Figure 12:
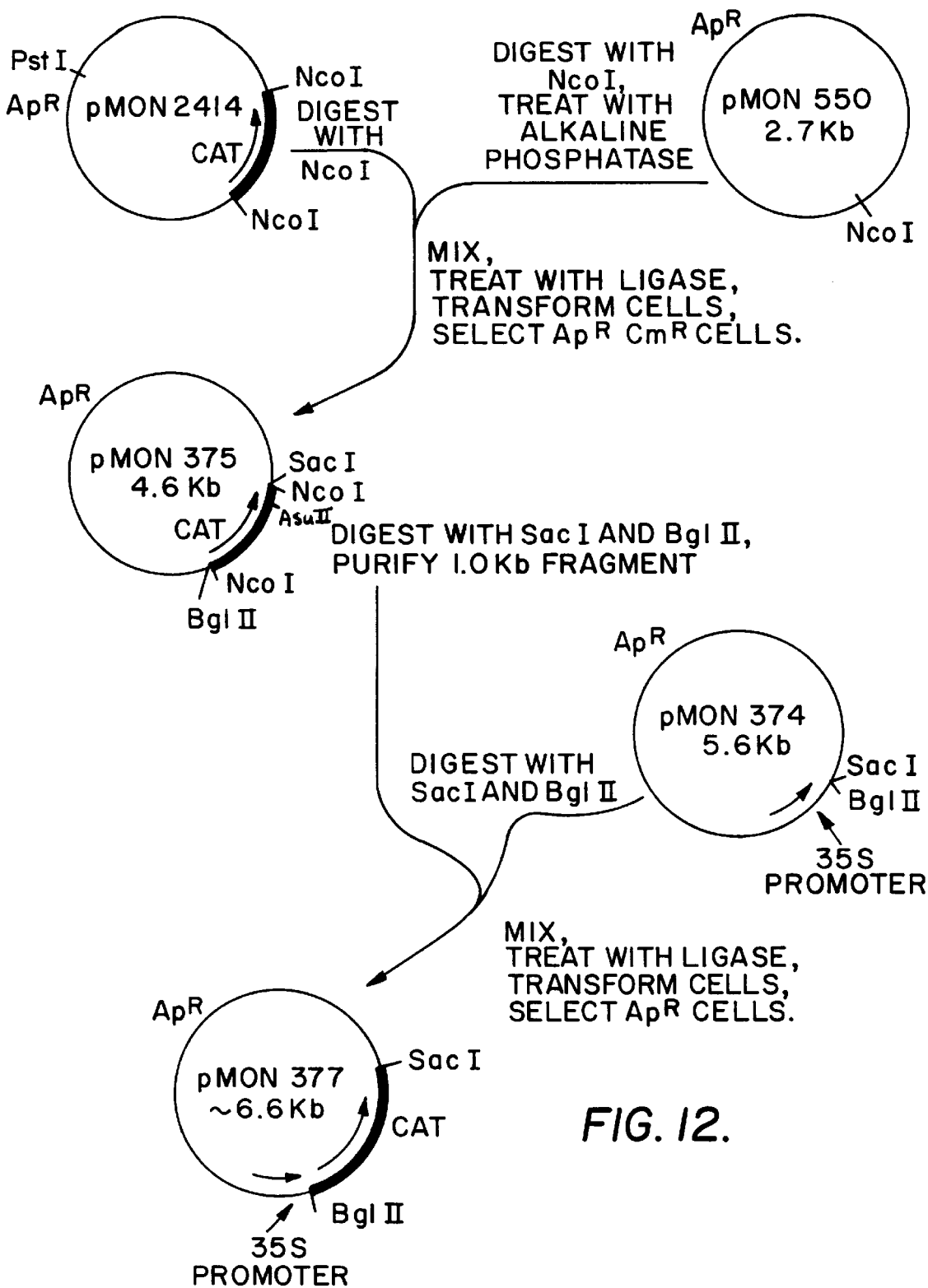
FIG. 12 depicts the construction of pMON377. The blackened area denotes the CAT DNA coding sequence.

For reasons of convenience in construction, the CAT coding sequence was obtained from plasmid pMON2414 (FIG. 12). The CAT gene in this plasmid had been modified to contain an NcoI site at the starting ATG of its coding sequence and both the internal NcoI and EcoRI sites had been removed by oligonucleotide-directed site-specific mutagenesis (Zoller and Smith, 1982). In addition, a second NcoI site was located 200 base pairs 3' downstream of the end of the CAT coding region.

To obtain a BglII site at the 5' end of the coding fragment and a SacI site at the 3' end of the coding region fragment, the NcoI fragment was inserted into the unique NcoI site of pMON550 (FIG. 12). The pMON550 plasmid is a derivative of pUC19 (Yanisch-Perron et al., 1985) in which the multilinker between the HindIII and EcoRI sites was replaced with the synthetic sequence below also bounded by HindIII and EcoRI sites:

```
HindIII    BglII NcoI              Sac    EcoRI
5'-AAGCTTTCTAGAAGATCTCCATGGAGGCCTGGTACCGAGCTCGAATTC
```

Again, any multilinker containing at least one unique restriction endonuclease cleavage site can be employed to facilitate the ordered assembly of a heterologous DNA sequence. The above preferred sequence contains unique cleavage sites for BglII, NcoI and SacI. The resultant plasmid was called pMON375 (FIG. 12) and permitted the isolation of the CAT coding sequence on a 960 bp BglII-SacI fragment. As shown in FIG. 12, this fragment was inserted next to the 35S promoter in pMON373 at the BglII-SacI sites. The resulting plasmid was called pMON377 (FIG. 12).

The final piece that was assembled to make the expression vector was a modified TGMV-A genome made deficient in the coat protein coding sequence by insertion of a synthetic HindIII linker (New England Biolabs, Beverly, Mass., 5'-CAAGCTTG) at the unique ScaI site at base pair 791 of the standard TGMV-A sequence (Hamilton et al., 1984). This was accomplished by cleavage of pMON305 with ScaI, ligation of the synthetic linkers to the products, cleavage with excess HindIII, the resulting 2.6 kb fragment was inserted into pUC18 cleaved with HindIII to give plasmid pMON344 (FIG. 13).

Plasmid pMON344 was further modified by digestion with AsuII, which cleaves pMON344 once in the TGMV-A DNA insert at bp 1037, and SmaI, which cleaves pMON344 once in the pUC18 multilinker. The digestion products were treated with the Klenow fragment of DNA polymerase and DNA ligase. The resulting plasmid, pMON376 (FIG. 13), carries the modified TGMV-A genome as an asymmetric fragment with a SacI site bounding the 3' portion of the interrupted coat protein coding sequence and a HindIII site adjacent to the 5' portion of the interrupted coat protein coding sequence.

Figure 13:
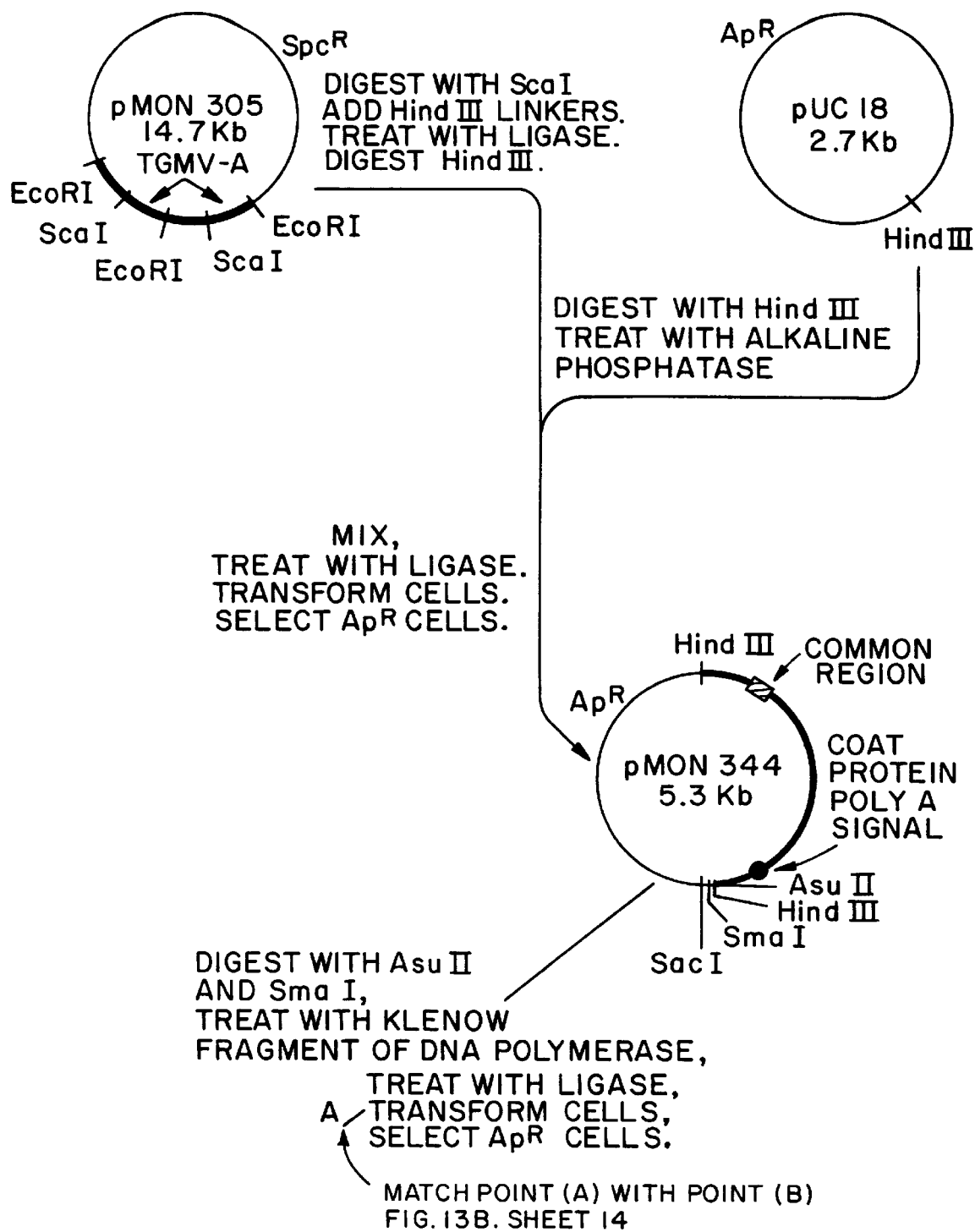
FIGS. 13A–13B depict the construction of pMON378. The blackened area represents DNA sequence 6 as labeled in FIG. 14. The hatched boxes represent TGMV common regions. The blackened circle represents the TGMV coat protein (CP) polyA DNA signal sequence.
Figure 13B:
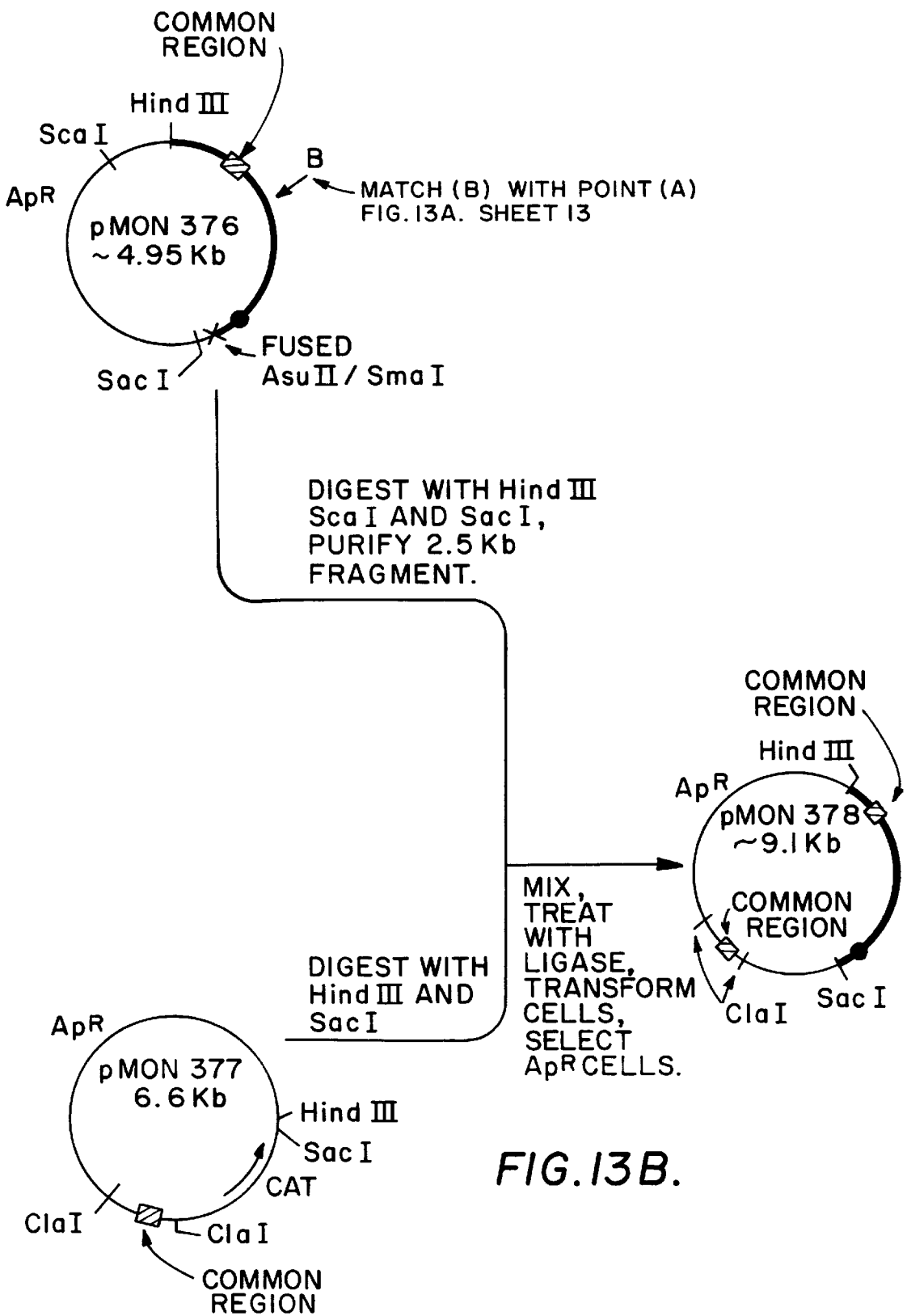
Figure 14:
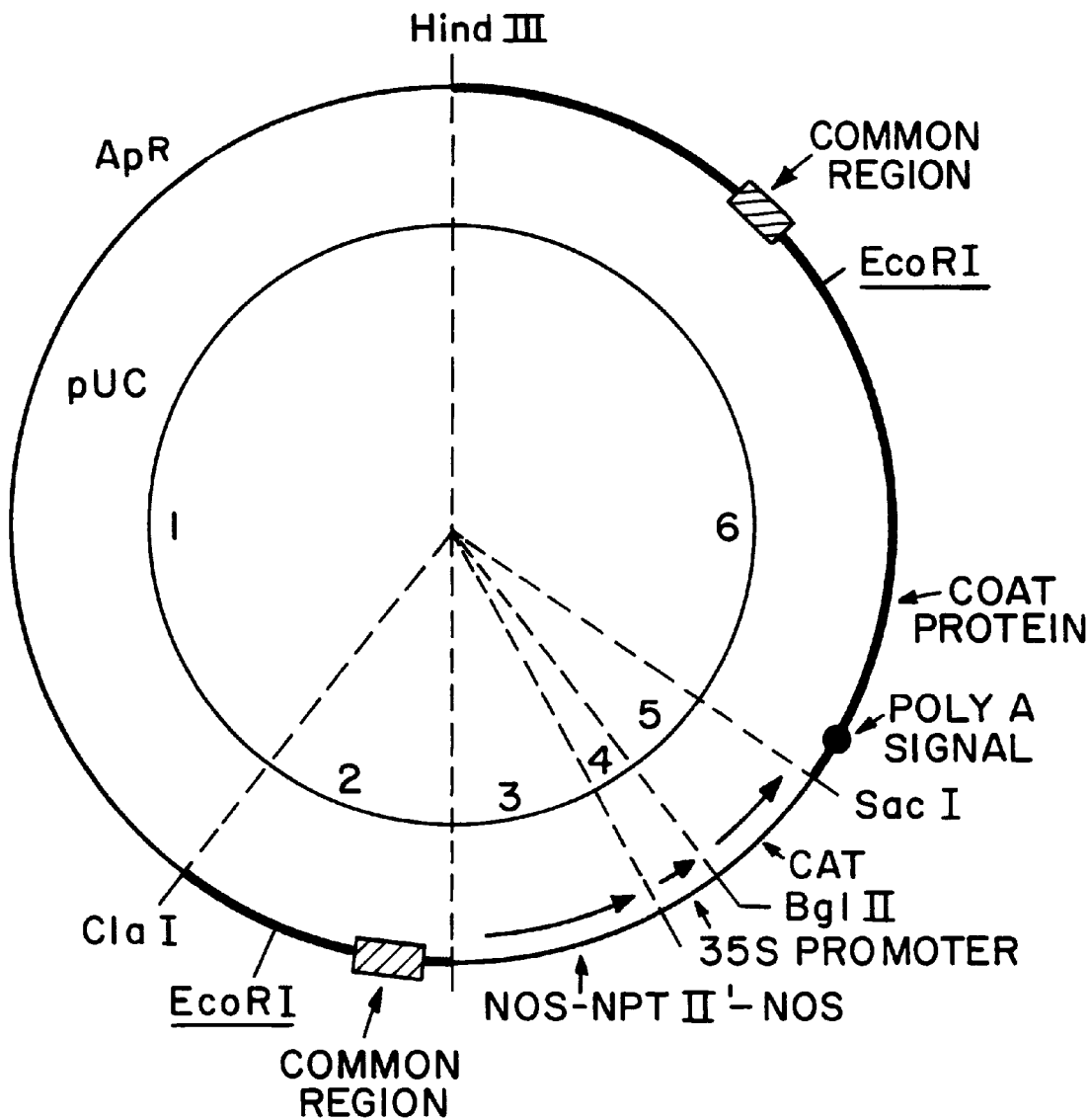
FIG. 14 depicts pMON378 wherein the relevant DNA coding sequences are identified as labeled thereon. The blackened circle represents the TGMV coat protein (CP) polyA (polyadenylation) DNA signal sequence.

As shown in FIG. 13, in one preferred embodiment of the present invention, a complete expression vector intermediate was assembled in the following manner. Plasmid pMON377 was cleaved with SacI and HindIII and mixed with the 2.6 kb SacI-HindIII TGMV-A fragment purified from pMON376. As shown in FIG. 14, the resulting plasmid, pMON378 contains the following features: For replication in E. coli, there is a pUC8 replicon (1) containing an ampicillin resistance gene for selection in E. coli. Next, there is a segment of TGMV-A DNA (2) from base pair 1814 to base pair 259 that includes the common region. Next to this segment is the chimeric NOS-NPTII'-NOS gene (3) that functions as a selectable kanamycin resistance marker in plant cells and plants. This chimeric gene is arranged so that its direction of transcription is away from the common region and in the same direction as the coat protein gene. Next to this is the CaMV 35S promoter (4) joined to the CAT coding sequence (5) also transcribed in the same direction as the NOS-NPTII'-NOS gene. The next segment is the modified TGMV-A genome (6) arranged with the 3' end of the coat protein coding sequence and its poly-adenylation signal adjacent to the 3' end of the CAT coding sequence. The other end of the modified TGMV-A genome is joined through the HindIII site to the pUC8 plasmid. The above components represent examples of the functional components which can be employed to create an expression vector.

Figure 15:
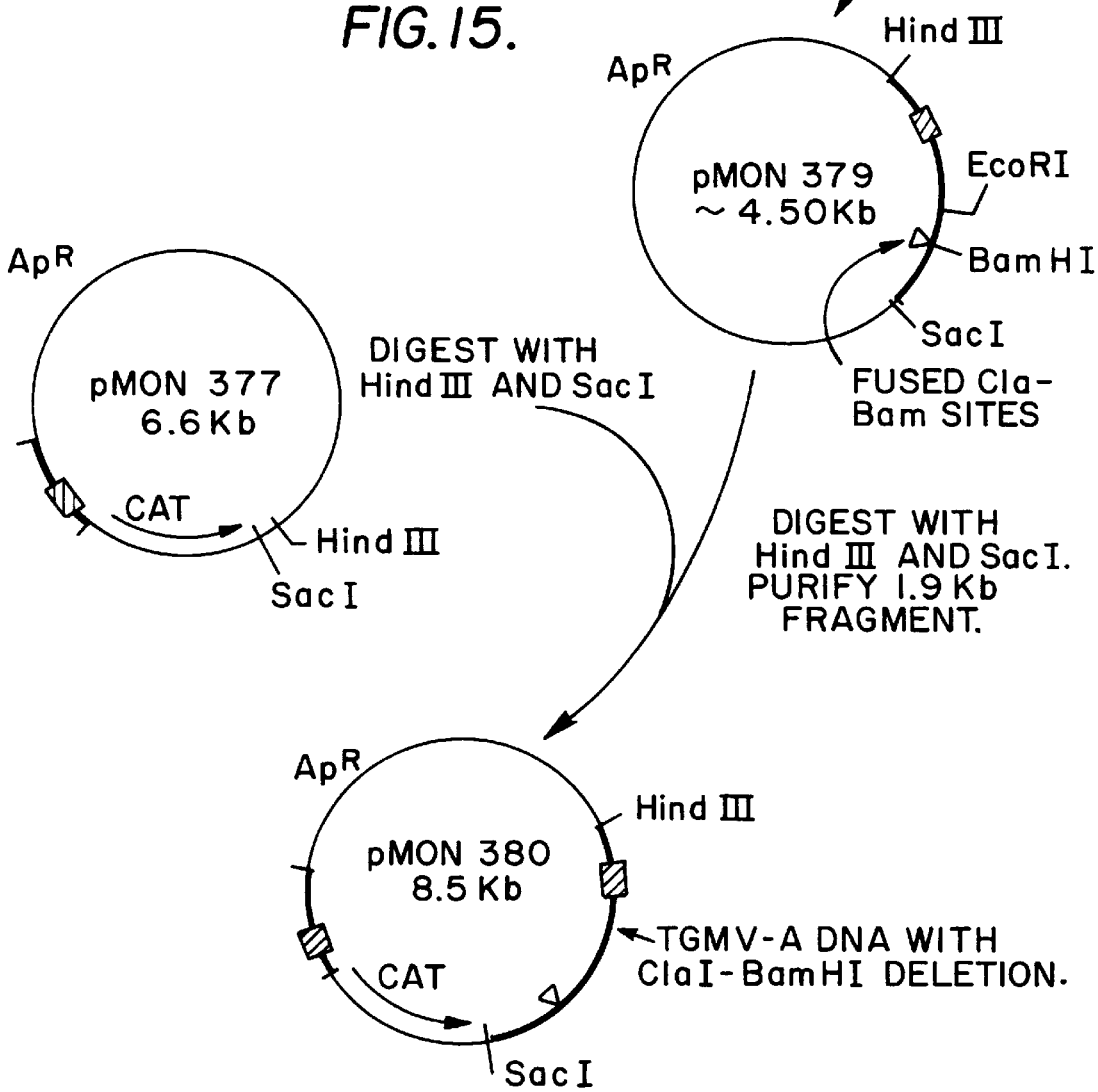
FIG. 15 depicts the construction of pMON380 comprising pMON377 having inserted therein in place of its HindIII-SacI fragment the TGMV-A DNA (blackened area) deleted from the ClaI to BamHI restriction endonuclease sites. The hatched box denotes the TGMV common region.

The pMON378 plasmid (FIG. 14) can be directly introduced into plant protoplasts by conventional means. Alternatively, since this plasmid contains two EcoRI sites that permit the release of the plant plasmid from the pUC vector, the intermediate plasmid DNA can be treated by cleavage with EcoRI, and the linear plant plasmid fragment introduced into plant protoplasts by convention means. Following the introduction of such DNAs into plant protoplasts or plant suspension cell cultures, an extract can be prepared from the transformed cells and assayed for CAT enzyme activity using the method of Fromm et al., 1985. As a control, protoplasts are treated with an equivalent amount of DNA of plasmid pMON380 (FIG. 15). The pMON380 plasmid is similar to pMON378 except that the Bam HI (base 1354) to ClaI (base 1814) fragment of TGMV-A DNA has been deleted. This results in loss of portions of the AL1, AL2 and AL3 (FIG.1) open reading frame coding information. The coat protein polyadenylation signals would still be located adjacent to the CAT gene to provide signals necessary for mRNA stability.

The successful transformation and resultant expression of the CAT gene would be indicated by an increase in the amount of CAT enzyme activity produced following transformation of the plant cells with the pMON378 plasmid as compared to the pMON380 plasmid. Since the only difference between the two plasmids is the presence of a complete, coat protein-deficient TGMV-A DNA in the pMON378 but not in the pMON380 plasmid, one could conclude that the this TGMV-A segment confers on the pMON378 plasmid the ability to replicate to high copy number in the plant protoplasts amplifying the copies of the CAT gene and the resultant amount of CAT enzyme produced by these cells.

As previously described, a alternative method for introduction of the intermediate DNA capable of generating plant plasmids in plant cells was developed using the *Agrobacterium tumefaciens* Ti plasmid transformation system (Fraley et al., 1983, 1985; Horsch et al., 1985). Among the advantages of this system is the high frequency at which the Agrobacterium can deliver DNA into plant cells. In addition, DNA sequences capable of generating the plant plasmids are introduced into the chromosomes of plant cells so that if plant plasmids are lost from the plant cell due to various causes such as instability due to expression of a certain heterologous gene product, they may be readily replenished by release of the plant plasmid from the chromosomal sequences by recombination or replication. Furthermore, heterologous DNA sequences so delivered are seed transmitted by the resultant, regenerated transformed plants.

The following describes a preferred construction and use of a Ti plasmid-based expression vector which produces plasmid DNA in transformed plant cells.

Plasmid pMON120 (Fraley et al., 1983) was cleaved with StuI and EcoRI and mixed with pMON521 DNA also cleaved with StuI and EcoRI. The pMON521 plasmid is a derivative of pMON505 from which the unique SmaI site was deleted by cleavage with XmaI, filling in the ends by treatment with the Klenow fragment of DNA polymerase and ligation. The plasmid resulting from the joining of fragments from pMON120 and pMON521, pMON372 (FIG. 16), no longer contains the chimeric kanamycin resistance gene but retains the multilinker of pMON521. The TGMV-A DNA, selectable marker and chimeric CaMV 35S promoter-CAT coding sequence was then introduced into pMON372 in the following manner. Plasmid pMON377 was digested with EcoRI and SacI and the resulting 3.5 kb fragment carrying the TGMV-A common region, chimeric NOS-NPTII'-NOS kanamycin resistance, the 35S promoter and CAT coding sequence inserted into pMON372 DNA that had also been cleaved with EcoRI and SacI. The resulting plasmid, pMON381, is shown in FIG. 17.

Figure 17A:
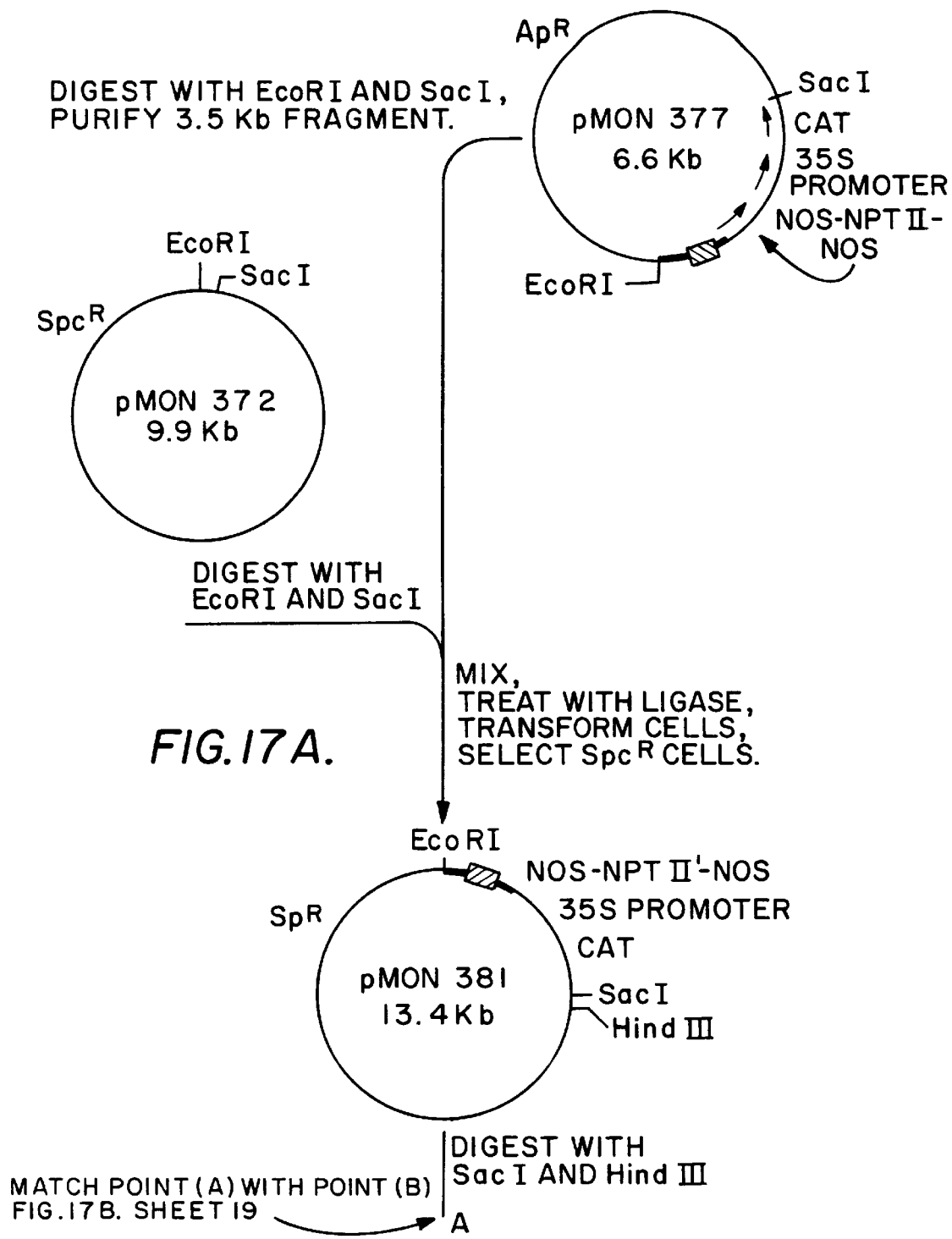
FIGS. 17A–17B depict the construction of pMON382 comprising pMON372 having inserted therein at the EcoRI-SacI site the 3.5 Kb EcoRI to SacI fragment from pMON377 carrying 600 bp of TGMV-A DNA, including the TGMV common region (hatched box), CaMV 35S promoter and CAT DNA coding sequence and having inserted therein at the SacI-HindIII site the SacI to HindIII fragment from pMON376 carrying a TGMV-A DNA segment lacking the C-terminal portion of the coat protein coding sequence. The blackened area on pMON382 represents TGMV-A DNA sequences and the hatched boxes represent TGMV common regions.
Figure 17B:
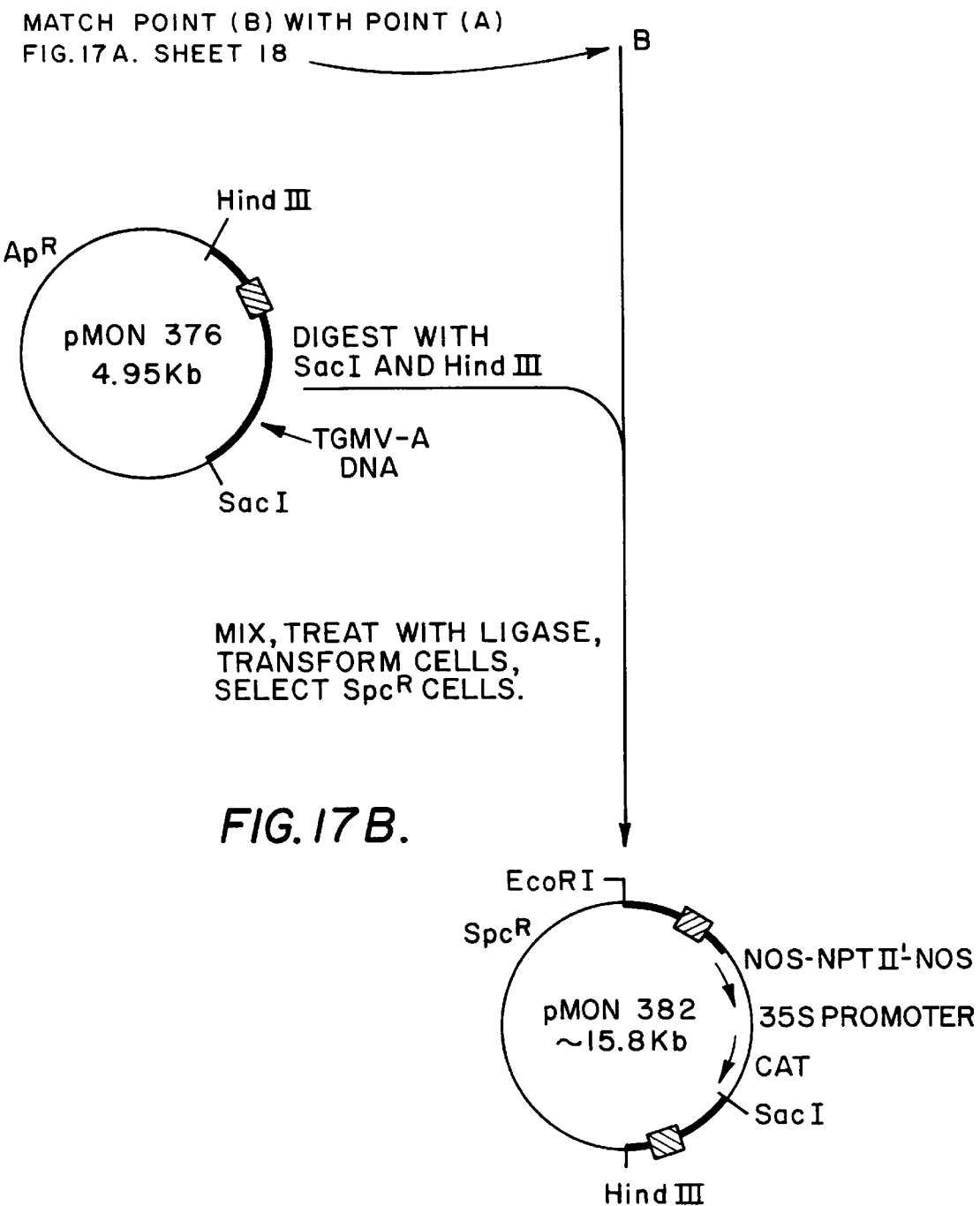
Figure 18:
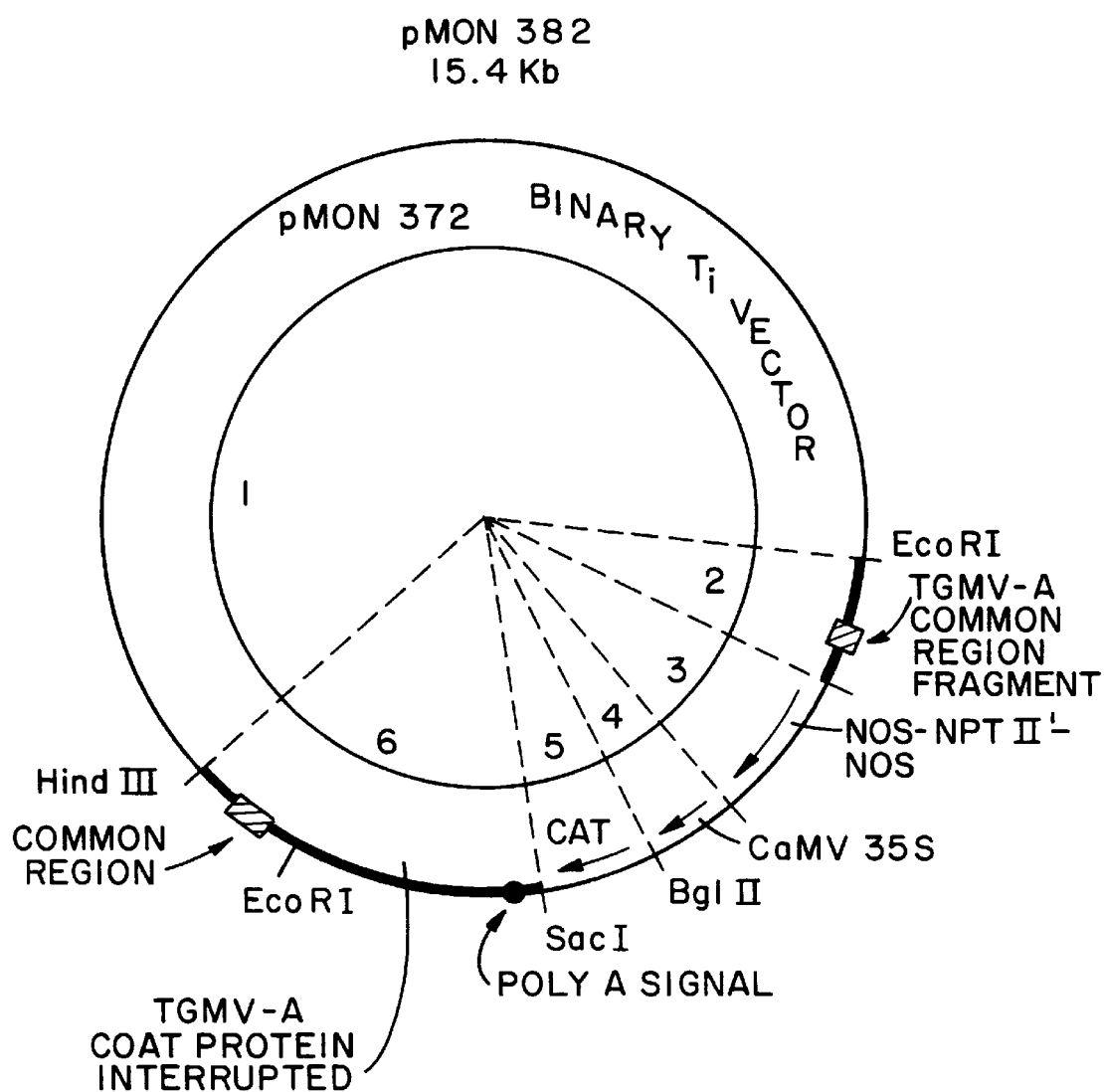
FIG. 18 depicts pMON382 wherein the relevant DNA sequences are identified as labelled thereon.

As shown in FIG. 17, full length TGMV-A DNA cleaved in the coat protein, was isolated from pMON376 cleaved with SacI and HindIII and joined to pMON381 also cleaved with SacI and HindIII. The resulting plasmid, pMON382 (FIGS. 17 and 18), was then introduced into *Agrobacterium tumefaciens* cells using the tri-parental mating procedure described in Fraley et al. (1983, 1985). As shown in FIG. 18, plasmid pMON382 is comprised of the following DNA segments:

a) A pMON372 "binary" type, Ti plasmid-based plant transformation vector (1).

b) A segment of the TGMV-A DNA containing the common region (2).

c) The chimeric NOS-NPTII'-NOS kanamycin resistance gene for selection of transformed plant cells (3).

d) The 35S CaMV promoter (4).

e) The CAT coding sequence (5).

f) A copy of the TGMV-A DNA cloned as a linear insert interrupted in the coat protein coding sequence (6). The common region in this TGMV-A DNA is a direct repeat of the first common region insert (2).

Plasmid pMON382 thus exemplifies a variant of plasmid pMON352 and was similarly demonstrated to be useful in both replicating and expressing heterologous DNA sequences in plants.

Figure 19:
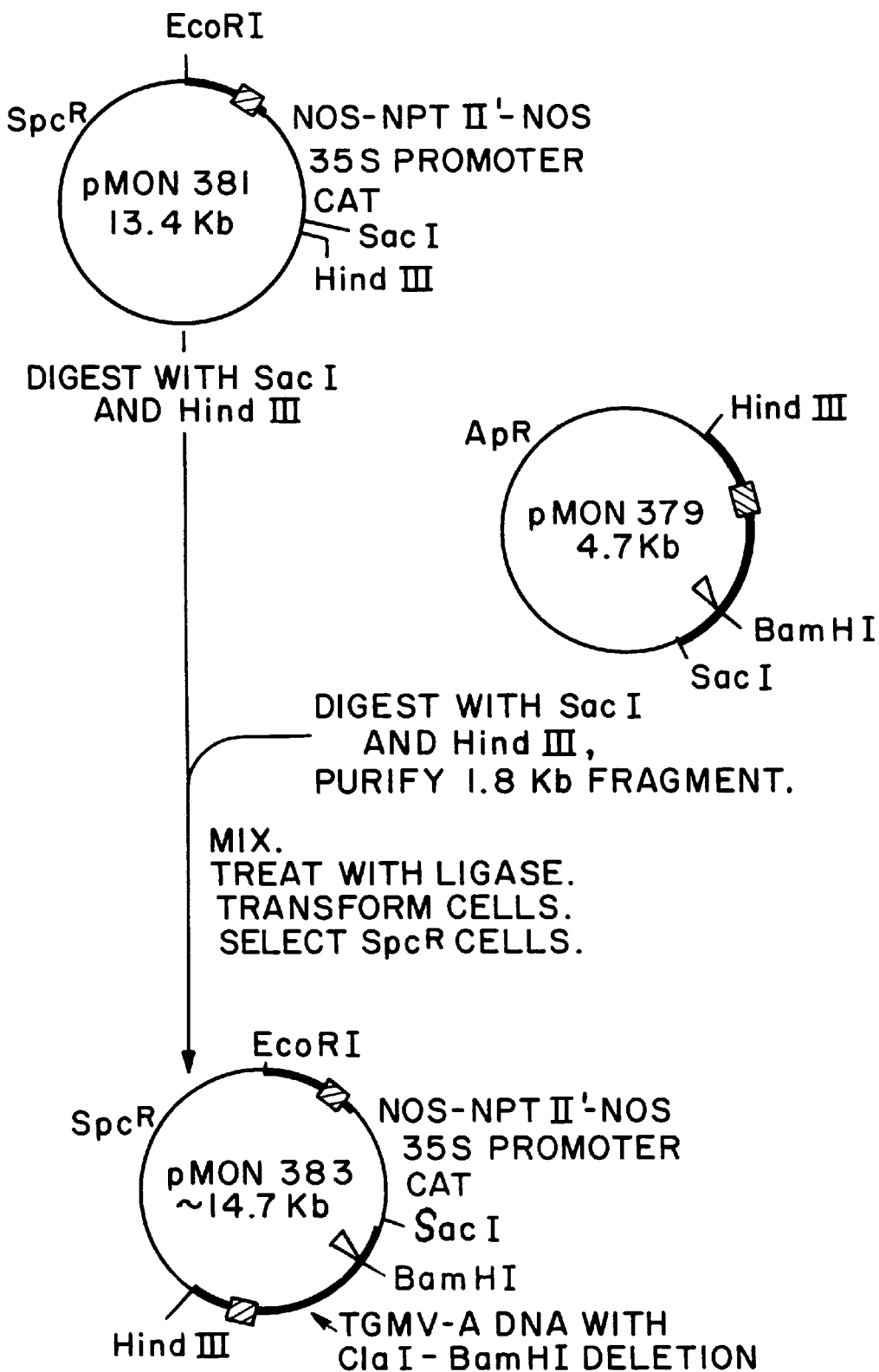
FIG. 19 depicts the construction of pMON383 comprising pMON381 having inserted therein in place of the SacI to HindIII fragment the blackened SacI to HindIII fragment from pMON379. The open triangle denotes a deletion of the ClaI to BamHI fragment from TGMV-A DNA. The hatched boxes represent the TGMV common region.

As a control, a sequence that does not encode a complete coat protein deficient TGMV-A DNA was inserted into pMON381 in the following manner. Plasmid pMON381 was cleaved with SacI and HindIII and the 1.2 kb SacI-HindIII fragment of pMON379 was inserted into the pMON381 plasmid to yield plasmid pMON383 (FIG. 19). This plasmid was introduced into *Agrobacterium tumefaciens* cells using the procedure of Fraley et al. (1983, 1985).

Agrobacterium cells carrying the pMON382 and 383 plasmids were employed to introduce the T-DNAs carrying the intermediate plant plasmid sequences into petunia cells using the leaf disc procedure described by Horsch et al. (1985). The ability to select for plant tissue able to grow in kanamycin-containing medium indicated successful expression of the kanamycin gene (NOS-NPTII'-NOS) is transformed tissue. Additionally, freely replicating ds DNA forms of geminivirus-containing DNA of the size (e.g. about 4.6 kb) expected for geminivirus plasmids able to replicate the heterologous (e.g. NOS-NPTII'-NOS and CAT) DNA contained therein was detected. These replicative DNA forms were detected in accordance with previously described methods.

As previously indicated, the present invention anticipates that expression vectors can be created from the coat-protein encoding genomes of any geminivirus. The following gives a preferred method for creation of such an expression vector from the coat protein-encoding cassava latent virus (CLV) DNA 1.

The starting segment comprising CLV-1 DNA can be obtained by isolation from the double stranded forms of the CLV-1 DNA produced in *N. benthamiana* infected with the West Kenyan 844 isolate of the virus (Stanley and Gay, 1983). The infected *N. benthamiana* plants can be obtained by inoculation of young plants with extracts of infected leaves using the procedure of Bisaro et al. (1982). After three weeks at 25° C., leaves from the plants showing maximum symptom development (curled, wrinkled leaves and yellowing) can be collected and treated as described in Dellaporta et al. (1983) to isolate the infected plant DNA.

A subfragment of the coat protein-encoding CLV-1 circular DNA that is interrupted in the coat protein coding sequence can be obtained as follows. Total CLV infected leaf DNA (50 $\mu$g) can be digested to completion with BamHI (100 units) and loaded on a preparative agarose gel. After sufficient time, the resultant 2585 bp BamHI fragment of CLV-1 DNA that includes the common region will be clearly separated on the gel and can then be purified using the NA-45 membrane procedure. The purified 2.6 kb fragment (0.2 $\mu$g) can be cloned by mixing with 0.2 $\mu$g of pUC18 (Yanisch-Perron et al., 1985) DNA that had been previously digested with BamHI and treated with alkaline phosphatase. Following transformation of *E. coli* MM294 cells and selection for ampicillin resistant colonies, plasmid DNA minipreps can be digested with BamHI to show the presence of the 2.6 kb insert and with EcoRI to determine the orientation of the inserted CLV-1 DNA. One plasmid of each orientation can be saved (FIG. 20) and called pMONa and pMONb, respectively.

Figure 20:
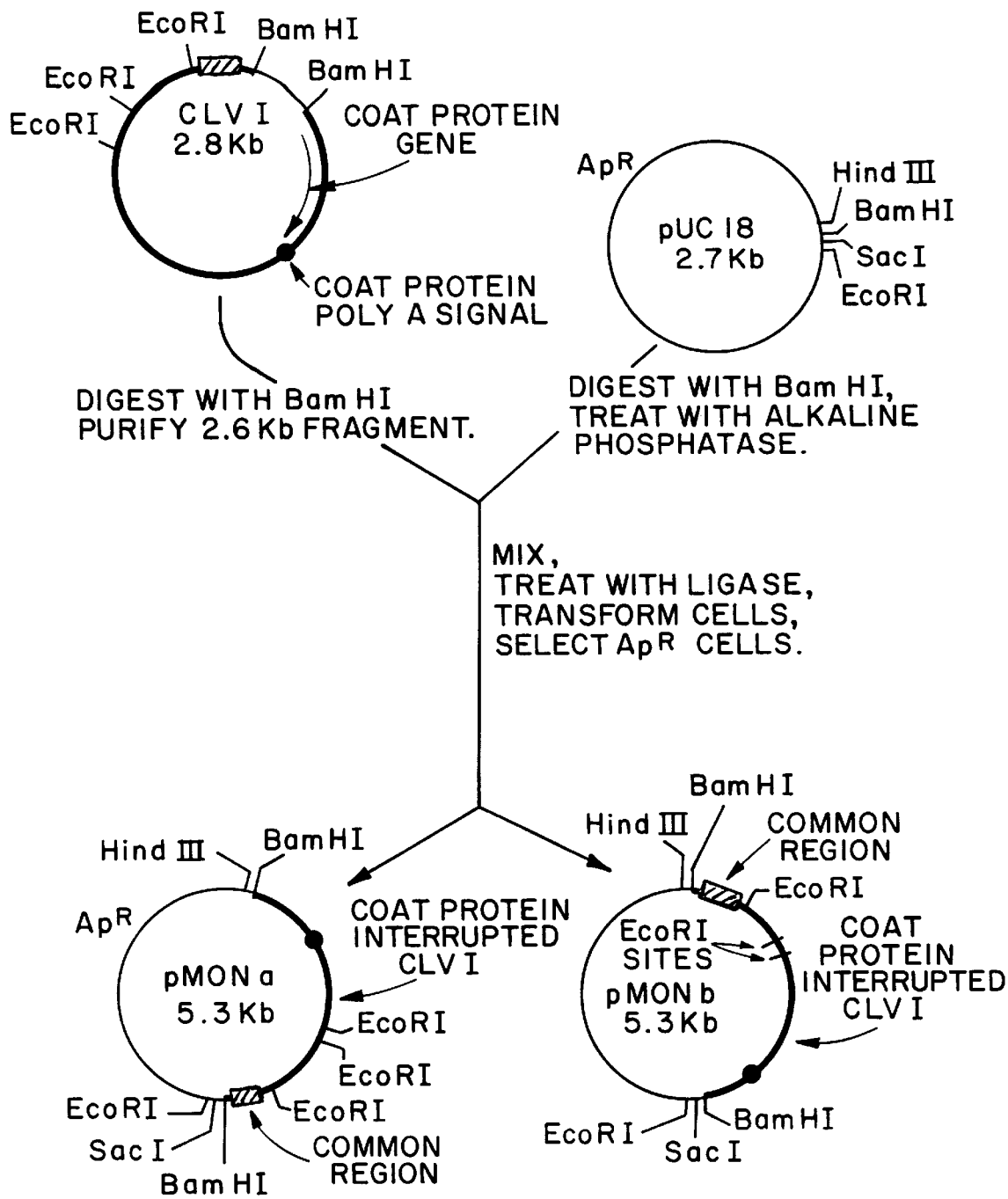
FIG. 20 depicts the construction of pMONa comprising pUC18 carrying a 2.6 kb BamHI fragment (blackened area) of CLV DNA 1 inserted into its BamHI restriction endonuclease site in one orientation. This figure also depicts the construction of pMONb comprising pUC18 carrying a 2.6 kb BamHI fragment (blackened area) of CLV DNA 1 inserted into its BamHI restriction endonuclease site in an alternate orientation. The CLV common region is shown by the hatched box and the blackened circle denotes the polyA signal DNA coding sequence.

As an acceptor plasmid for the CLV-1 common region fragment, a derivative of pMON377 can be created by digestion of 0.5 μg of the plasmid DNA with 2 units of ClaI to excise the 1 kb TGMV-A common region fragment. After ligation and transformation of E. coli MM294 cells, DNA mini-preps can be made from the resulting ampicillin resistant colonies. The mini-prep DNAs can be digested with ClaI to test for loss of the 1 kb insert. A plasmid lacking the insert can be saved and called pMONc (FIG. 20).

Figure 21A:
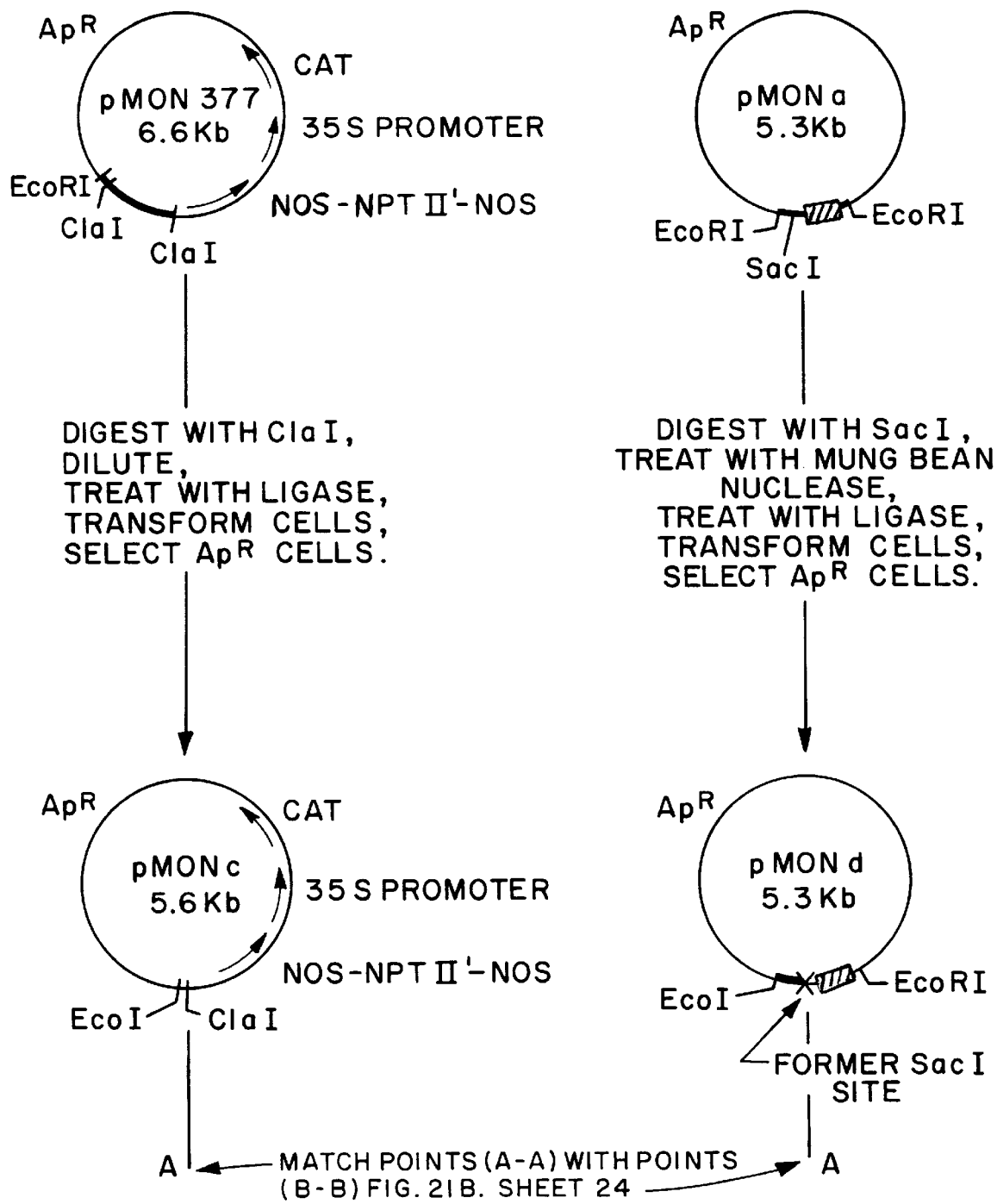
Figure 22:
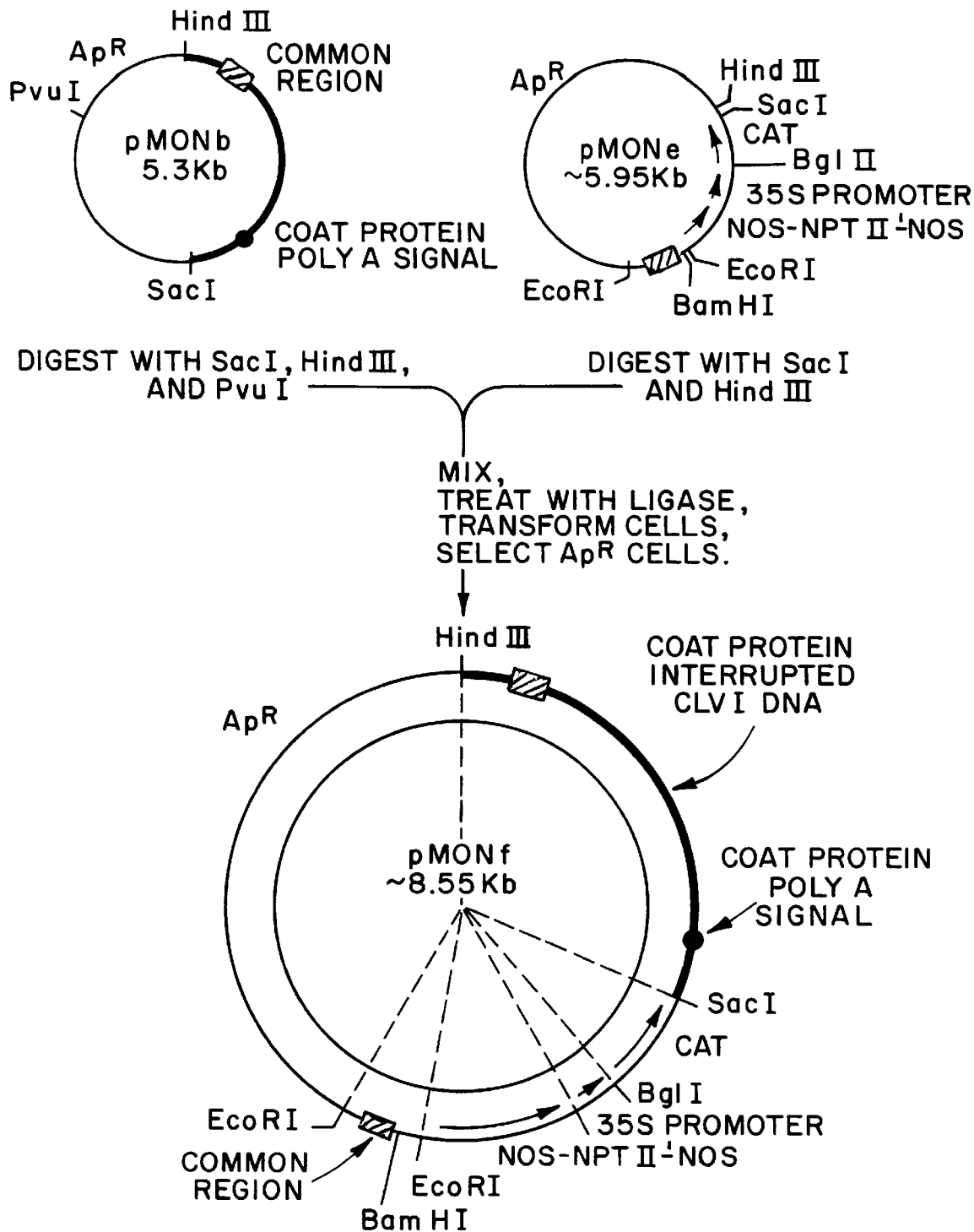
FIG. 22 depicts the construction of pMONf comprising pMONe carrying a 2.6 kb SacI to HindIII fragment (blackened area) isolated from pMONb and inserted into the SacI-HindIII site in pMONe. The hatched box denotes the CLV common region, and the blackened circle denotes the polyA signal. DNA coding sequence. The relevant DNA coding sequences on pMONf are identified as labeled thereon.

As a donor for the CLV-1 common region fragment, plasmid pMONa DNA (1 μg) can be digested with SacI (2 units) and treated with mungbean nuclease to remove the SacI cleavage site sequences. Following ligation and transformation of E. coli MM294 cells, DNA mini-preps can be made from the resulting ampicillin resistant colonies and digested with SacI to show the loss of the SacI cleavage site and EcoRI to show that the 350 bp common region fragment remains. One of these plasmids can be saved and called pMONd (FIG. 21).

The CLV-1 common region fragment can be joined to the NOS-NPTII'-NOS kanamycin resistance marker for plant cells and the CaMV 35S promoter joined to the chloramphenicol acetyl transferase (CAT) coding sequence as follows. Plasmid pMONd DNA (20 μg) can be digested with EcoRI (20 units) and the resulting 350 bp fragment isolated using the NA-45 membrane procedure. The 350 bp fragment (0.2 μg) can be mixed with 0.5 μg of pMONc DNA that is prepared by digestion with EcoRI and treatment with calf alkaline phosphatase. Following ligation and transformation of E. coli MM294 cells with selection for ampicillin resistant colonies, DNA mini-preps can be prepared from some of these colonies. The DNAs can be digested with EcoRI to demonstrate the presence of the 350 bp fragment and with BamHI to determine the orientation of the inserted fragment. A plasmid carrying the insert and having two BamHI sites located 1.3 kb apart can be saved and called pMONe (FIG. 21).

To complete the assembly of an intermediate plasmid carrying a coat protein deficient CLV-1 DNA bounded by two common regions and carrying a kanamycin resistance marker for plants and the CaMV 35S promoter joined to the CAT gene, the following can be done. Plasmid pMONb DNA (2 ug) can be digested with SacI (4 units) and HindIII (4 units) to release the 2.6 kb coat protein interrupted CLV-1 DNA and further digested with PvuI (4 units) to inactivate the pUC portion of the pMONb DNA. This digested DNA can then be combined with 1 μg of pMONe DNA that has been digested with SacI (2 units) and HindIII (2 units). Following treatment with ligase and transformation of *E.coli* MM294 cells, DNA mini-preps can be made from the resulting ampicillin resistant colonies. The mini-prep DNAs can be digested with SacI and HindIII to demonstrate the presence of the 2.6 kb insert into the 6 kb pMONe plasmid. A plasmid having these characteristics can be saved and called pMONf (FIG. 22).

The resulting pMONf plasmid would be the CLV-1 analogue of the pMON378 plasmid (FIG. 14) and would possess the same characteristics as described for pMON378 in this application.

Introduction of the CLV-1 analogous segments into a Ti plasmid based vector can be accomplished in a manner analogous to that for the creation of pMON382 (FIG. 18).

The following examples illustrate preferred embodiments of the present invention and are not intended to limit the invention's scope in any way. While this invention has been described in relation to its preferred embodiments, various modifications thereby will be apparent to one skilled in the art from reading this application.

Microorganisms and Plasmids

The following microorganisms are available from the American Type Culture Collection (ATCC), 12301 Parklawn Drive, Rockville, Md., 20852, U.S.A.:

ATCC 53303-*E. coli* MM294 (pMON295)

ATCC 53304-*E. coli* MM294 (pMON305)

ATCC 53301-*E. coli* MM294 (pMON505)

ATCC 53302-*Agrobacterium tumefaciens* GV3111-SE (pTiB6S3-SE)

These deposits are available to the public upon the grant of a U.S. patent to the assignee of this application, Monsanto Company. These deposits will be available for the life of any such U.S. patent having the benefit of the filing date of this application. However, it should be understood that the availability of a deposit does not constitute a license to practice the subject invention in derogation of patent rights granted by governmental action. Furthermore, the present invention is not to be limited in scope by the microorganisms deposited, since the deposited embodiments are intended only as specific illustrations of the invention.

Materials and General Methods

All restriction enzymes were obtained from New England Biolabs (Beverly, Mass.), Promega-Biotech (Madison, Wis.), Boehringer Mannheim Biochemicals (Indianapolis, Ind.) and Bethesda Research Laboratories (Gaithersburg, Md.) and used according to the manufacturers' instructions. Recognition sequences can be found in Kessler et al.(1985). Bacteriophage T4 DNA ligase was prepared using a modification of Murray, et al.(1979). DNA ligations were carried out in a volume of 15 to 100 ul in a buffer consisting of 25 mM Tris-HCl pH 7.6, 10 mM $MgCl_2$, 10 mM dithiothreitol, 0.2 mM spermidine and 1 mM ATP. Generally, 10 to 30 units were added and the reaction mixture incubated for 16 hours at 12° C. Klenow polymerase and calf alkaline phosphatase were obtained from Boehringer Mannheim Biochemicals (Indianapolis, Ind.) and used according to the manufacturers' instructions. Mungbean nuclease was obtained from Pharmacia-PL Biochemicals (Piscataway, N.J.) and used according to the manufacturer's instructions.

Plasmid DNA for rapid screening was prepared by the alkaline extraction method of Ish-Horowicz and Burke (1981). Large scale plasmid DNA purifications were done according to Davis et al. (1980) or by using the modified alkaline lysis procedure of Ish-Horowicz and Burke (1981) followed by NACS-52 column purification as per manufacturers' instructions (Bethesda Research Laboratories, Gaithersburg, Md.).

DNA restriction fragments were isolated after electrophoresis in horizontal agarose using NA-45 DEAE membrane (Schleicher and Schull, Keene, N.H.) according to manufacturers' instructions.

Synthetic DNA multilinkers used to construct certain of the plasmids were assembled on an Applied Biosystems DNA Synthesizer (Applied Biosystems, Inc., Foster City, California) following the manufacturer's recommended procedures.

The following *E. coli* strains were used as recipients in transformation

LE392 and MM294 (Maniatis et al., 1982)

JM101 (Vieira and Messing, 1982)

GM48 (Bale et al., 1979)

*E. coli* strains LE392, MM294, and JM101 may be obtained from the ATCC under ATCC accession numbers 33572, 33625, and 33876, respectively. *E. coli* GM48, a $dam^-$, $dcm^-$, strain, may be obtained from M. G. Marinus, Department of Pharmacology, University of Massachusetts Medical School, Worcester, Mass., 01605.

E. coli strains were transformed according the methods of Maniatis et al. (1982).

Luria broth (LB) and plates were prepared as described by Davis et al. (1980). Antibiotics, filter sterilized and stored frozen, were used in the following concentrations: ampicillin (Ap) 200 µg/ml; spectinomycin (Spc) 50 µg/ml. For certain clonings into pUC plasmids or their derivatives, the medium also contained 10 µg/ml IPTG (isopropyl-β-D-thioga-lactoside) and 25 µg/ml Xgal (5-bromo-4-chloro-3-indolyl-β-D-galactopyranoside).

Agarose gel electrophoresis was performed in Tris-acetate EDTA buffer containing 1 µg/ml ethidium bromide as described in Maniatis et al. (1982). The agarose concentration was 0.8% (w/v).

Isolation of DNA from plant materials was carried out using the procedure of Dellaporta et al. (1983).

Assays for chloramphenicol acetyl transferase were carried out essentially as described by Canon and Primrose (1974). The bacterial standard employed was chloramphenicol 3-0-acetyletransferase, E.C.2.3.1.28, Sigma No. C-2900 (Sigma, St. Louis, Mo.) reconstituted with 5.0 milliliters (ml) 0.25M Tris, pH 7.8, to a final concentration of 0.1 units (U) per microliter (µl). Other reagents included acetyl CoA, Sigma No. A-2897 (tri-sodium, tri-hydrate) (Sigma, St. Louis, Missouri), $^{14}$C chloramphenicol (NEN 408, dichloroacetyl-1, 2–$^{14}$C) (New England Nuclear) with specific activity of 45.5 mCi/mmole, in ethanol; and 100% ethyl acetate stored at 4° C. A typical assay was conducted as follows. Leaf tissue was ground-up in 200 microliters (µl) of 0.25 M Tris, pH 7.8, in microfuge tubes containing microbeads, vortexed 30 seconds (sec.) and then centrifuged for 10 minutes (min.) at 4° C. in a microfuge. The supernatant was then heated at 65° C. for 15 min. and 150 µl of the heated extract was then mixed with 10 µl $^{14}$C chloramphenicol and incubated at 37° C. for 5 min. 20 µl of 4 mM acetyl CoA was then added, the mixture vortexed and incubated at 37° C. for 30 min. The reaction was stopped by adding 2 ml of cold (4° C.) ethyl acetate and then vortexed. The organic layer was then removed and dried in an evaporator, resuspended in 30 µl ethyl acetate and then spotted on silica gel TLC plates and run (ascending) in 95:5 chloroform-methanol for about 45 min. The plates were air dried and exposed to x-ray film overnight.

For Southern blot analysis, DNA (usually 0.5–1 µg) was loaded onto 0.8% (w/v) agarose gel, prepared as described above, containing 1 µg/ml ethidium bromide and electrophoresed until sufficient separation was achieved (4 hours at 85 V). The gel was then exposed to UV light for 15–30 seconds. Next, the gel was washed twice (each time for 10–15 minutes) with 0.25M hydrochloric acid and then rinsed with distilled water. After rinsing, the gel was washed twice (each time for 30 minutes, 1 hour total) with denaturing solution containing 0.5N NaOH, 1.5M NaCl and then rinsed again with distilled water. Next, the gel was washed twice (each time for 30 minutes, 1 hour total) with neutralizing solution containing 0.5M Tris (pH7), 3M NaCl.

At this point the gel was placed on 2 layers of Whatman 3MM paper on top of a sponge (Cellogel) saturated with 20×SSC (3M NaCl, 0.3M NaCitrate). Nitrocellulose membrane (Schleicher and Schull, Keene, New Hampshire), prewetted with 20×SSC, was placed on top of the gel, followed by 2 more layers of Whatman 3MM paper, several layers of paper towels, and a small weight to ensure good contact during transfer of the DNA from the gel to the nitrocellulose membrane. After 4 hours, the nitrocellulose membrane was removed, rinsed in 20×SSC, and then baked under vacuum at 80° C. for 2 hours.

After baking the nitrocellulose membrane was incubated at 42° C. in hybridization buffer containing 50% formamide, 5×SSC, 5×Denhardt's solution (Maniatis et al, 1982), 0.2% SDS, and 100 µg/ml denatured salmon sperm DNA for 2 hours. Next, the nitrocellulose membrane was incubated in fresh hybridization buffer containing boiled and quenched $^{32}$P-labelled probe DNA (Rigby et al., 1977) for 48 hours at 42° C. After hybridization the nitrocellulose membrane was washed twice with 2×SSC, 5Mm EDTA, 0.2% SDS for 30 minutes each at 65° C. and once with 0.2×SSC, 5 mM EDTA, 0.2% SDS for 30 minutes at 65° C. The nitrocellulose membrane was then sealed in a plastic bag and exposed to X-ray film to visualize DNAs that hybridize to the radioactive probe.

EXAMPLE 1

The following example demonstrates the construction of three geminivirus DNA containing vectors used to establish autonomous replication of the coat protein-encoding DNA of a binary geminivirus, in particular, the TGMV-A component, in plants. The creation of plants containing TGMV-A or TGMV-B component DNAs and a demonstration of the autonomous replication of TGMV-A DNA in transformed plants is also described.

a. Construction of pMON305

Plasmid pBH404 (Bisaro et al., 1982) DNA (20 ug) was digested with EcoRI (40 units) and the 2.6 kb TGMV-A fragment was purified using NA-45 membrane. Two ug of the purified fragment was mixed with 0.1 μg of pMON200 DNA that had been cleaved with EcoRI and treated with calf alkaline phosphatase. After ligation and transformation of *E. coli* MM 294 cells with selection for spectinomycin resistance, fifty colonies were obtained. DNA mini-preps were made from twelve of these. Restriction endonuclease analysis with EcoRI and ClaI showed that one of these plasmids contained two tandem inserts of the TGMV-A fragment with the structure shown in FIG. 2. This plasmid was called pMON305.

b. Construction of pMON308 and pMON309

Plasmid pBH602 (Bisaro et al., 1982) DNA (20 ug) was digested with ClaI (50 units) and the 2.5 kb TGMV-B fragment was purified. Two μg of the purified fragment was mixed with 0.1 μg of pMON200 (Fraley et al., 1985) DNA that had been previously cleaved with ClaI and treated with calf alkaline phosphatase. After ligation and transformation of *E. coli* MM 294 cells, 100 spectinomycin resistant colonies were obtained. DNA mini-preps were made from twelve of these colonies. Restriction endonuclease analysis showed that one of these plasmids contained three tandem inserts of the TGMV-B DNA and another contained four tandem inserts. These plasmids were named pMON308 and pMON309 and have the structures shown in FIG. 2.

c. Creation of Plants Containing TGMV-A or -B Component DNAs

The kanamycin resistant petunia and tobacco callus obtained as described in Example 13 was grown on regeneration medium (MS104) media, (Horsch et al. 1985) containing 500 μg/ml carbenicillin and 300 μg/ml kanamycin for 3–6 weeks until healthy shoots grew out of the callus. When these shoots reached a reasonable size (1.5–2.5 cm) they were excised from the callus tissue and placed onto rooting medium (MSO) (Horsch et al. 1985) with the cut end of the shoot embedded into the medium to stimulate root formation. After 1–5 weeks shoots which had formed roots were put into soil and grown to maturity.

To insure that the plants obtained in this manner contained integrated T-DNA including the NOS gene and NOS-NPTII'-NOS gene found in all of the constructs listed above, the following tests were performed. Assays for expression of nopaline in these plants were performed according to Rogers et al. (1986). To assay for expression of the NOS-NPTII'-NOS gene in transformed petunia plants, leaf tissue was excised from these plants and placed on MS104 medium containing 300 μg/ml kanamycin. Growth of callus from the leaf tissue confirmed expression of this gene in these plants. For tobacco, seeds were taken from self crossed transformed plants and placed on MSO medium containing 300 μg/ml kanamycin. Seeds capable of germinating and growing on this medium were obtained in a ratio expected from normal Mendelian inheritance of the NOS-NPTII'-NOS gene from the transformed parent plants.

d. TGMV-A and TGMV-B Components in Tranformed Petunia and Tobacco

Total DNA was isolated from petunia and tobacco plants transformed with *A. tumefaciens* containing pMON305, electrophoresed on 0.8% (w/v) agarose gel, blotted onto nitrocellulose, and hybridized to a probe containing pUC8 and an insert specific for the TGMV-A component (pMON349). These DNA's from both petunia and tobacco contained bands which hybridized to the TGMV-A probe and comigated with TGMV viral DNA in both ds and ss forms.

To verify the existence of the TGMV-B components in transformed tobacco plants, free DNA delivery experiments were performed as follows. Leaves of kanamycin resistant progeny from transgenic plants obtained by transformation with *A. tumefaciens* containing pMON308 and pMON309 were innoculated with pMON337 DNA (10 μg/plant) after wounding the leaf surface by light rubbing with carborundum. Symptoms characteristic of TGMV infection were present on the plants 10–20 days after innoculation. Since both TGMV components are required for symptom production, this experiment demonstrates the existence of the TGMV-B component in plants transformed with *A. tumefaciens* containing pMON308 or pMON309.

For petunia, the existence of the TGMV-B component in transformed plants was verified by crossing with TGMV-A transformed plants. Progeny from nop⁺, kanamycin resistance petunias transformed with *A. tumefaciens* containing either pMON308 or pMON309 were crossed with progeny from transformed petunias known to contain integrated and freely replicating TGMV-A viral DNA. Progeny from these crosses displayed symptoms characteristic of TGMV infection at a ratio expected from simple Mendelian inheritance of the TGMV-A component from one parent and the TGMV-B component from the other. This result demonstrates the existence of the TGMV-B component in plants transformed with *A. tumefaciens* containing pMON308 or pMON309.

EXAMPLE 2

The following example demonstrates the construction of cloned TGMV-A and -B components each lacking the TGMV common region. These cloned TGMV components are useful in identifying TGMV-A and -B DNA forms.

a. Construction of pMON344

To construct pMON344, it was necessary to first alter the unique ScaI site located in the coat protein coding sequence of TGMV-A to a HindIII site. This was accomplished by cleaving 5 μg of pMON305 DNA with 10 units of ScaI. The ScaI cleaved pMON305 DNA was treated with ligase in the presence of 40 ng of synthetic HindIII linkers (5'-pCAAGCTTG, New England Biolabs). After 16 hours at 14° C., the ligase was heat inactivated at 70° C. for 15 minutes, cooled to room temperature and treated with excess HindIII (20 units) for 3 hours at 37° C. Approximately 2.5 μg of this DNA was added to 1.0 μg of pUC18 DNA which had been cleaved with HindIII and treated with calf alkaline phosphatase. *E. coli* JM101 cells were transformed with the ligation mixture and selected on LB Ap plates containing Xgal and IPTG. Fifty colonies, two of which were white indicating that they carried an inserted DNA, were recovered. These colonies were grown up in ampicillin containing media and the DNA recovered by alkaline lysis. Restriction enzyme digestion analysis with HindIII, BamHI, ClaI, and KhoI showed that one of these was correct. Orientation of the inserted DNA was determined from the BamHI digestion pattern. The construct was then named pMON344 (FIG. 5).

b. Construction of pMON349

Plasmid pMON344 (FIG. 5) DNA (2 μg) was digested with HindIII (10 units) and EcoRI (10 units). Following heat inactivation of the restriction endonucleases the digestion mixture was treated with ligase. The mixture was transformed into JM101 cells and plated on LB Ap plates containing Xgal and IPTG. Approximately 400 colonies were obtained 150 of which were white indicating that the plasmid carried an insert. DNA mini preps were made from twelve of these and digested with BamHI, EcoRI and HindIII. One of these proved to carry a 1460 bp EcoRI-HindIII fragment. This plasmid was saved and called pMON349 (FIG. 3).

c. Construction of pMON350

Plasmid pUC8NL (FIG. 9) DNA (2 μg) was cleaved with BglII (10 units), ClaI (10 units) and calf alkaline phosphatase. After heat inactivation (70° C., 10 min.) This DNA was combined with 5 μg of pMON309 DNA that had been digested with 10 units each of BglII and ClaI followed by heat inactivation. The mixture was treated with DNA ligase and used to transform JM101 cells with selection for ampicillin resistance. Twelve of the 300 colonies obtained were used to prepare DNA mini-preps. The DNAs were digested with ClaI and BglII to screen for the presence of a 1570 bp ClaI-BglII fragment. One plasmid containing this fragment was saved and called pMON350 (FIG. 3).

EXAMPLE 3

The following example demonstrates the construction of an intermediate vector useful in constructing an intermediate binary Ti plasmid vector, in particular, pMON505, into which a geminivirus plasmid vector may be inserted.

a. Construction of pMON503

Plasmid pMON200 (Fraley et al., 1985) DNA (4 ug) was digested with NdeI and treated with DNA ligase. After transformation of *E. coli* MM294 cells and selection of spectinomycin resistant cells, 300 colonies were obtained. DNA mini-preps were made from 24 of these and digested with NdeI to show the absence of a 900 bp NdeI fragment, and BamHI, PstI, or BamHI and EcoRI to determine the orientation of the remaining NdeI fragments. One plasmid showing the correct orientation and loss of the 900 bp NdeI fragment was saved and called pMON503 (FIG. 5).

b. Construction of pMON505

Plasmid pMON503 DNA (4 µg) was digested with SmaI and HindIII and mixed with 4 µg of pTJS75 DNA also cleaved with SmaI and HindIII. After treatment with DNA ligase and transformation, 250 spectinomycin resistant *E. coli* MM294 colonies were obtained. DNA mini-preps were made from 12 of these and screened for the 3.8 kb HindIII-SmaI fragment by digestion with SmaI and HindIII, PstI, SalI and PstI and PstI and SmaI. One of these showing the correct structure was saved and called pMON505 (FIG. 4).

EXAMPLE 4

The following example demonstrates various intermediate plasmid vectors useful in assembling a TGMV-A component for insertion into a Ti plasmid for delivery into plant cells. Specifically, the TGMV-A DNA is assembled so that the coat protein-encoding DNA sequences are interrupted to create a coat protein minus (CP⁻) A DNA sequence flanked by TGMV common regions. The resultant pMON352 vector may also be employed in a free DNA delivery system to give rise to geminivirus plant plasmid.

a. Construction of pMON345

Plasmid pMON344 (FIG. 6) DNA (10 µg) was digested with HindIII and ScaI and the 2.6 kb HindIII TGMV-A fragment was purified using the NA-45 membrane procedure. Five µg of the purified fragment were mixed with 1 µg of pMON505 DNA that had been cleaved with HindIII and treated with calf alkaline phosphatase. Following ligation and transformation of *E. coli* MM294cells, 470 spectinomycin-resistant colonies were obtained. Twelve of the colonies were tested for ampicillin resistance and eight were found to be sensitive. DNA mini-preps were made from these eight colonies and screened for the presence of the 2.6 kb HindIII fragment. Two of the plasmids contained the insert and EcoRI digestion showed that one had the orientation shown in FIG. 6. This plasmid was saved and called pMON345.

b. Construction of pMON352

Plasmid pMON345 DNA (5 µg) was digested with StuI which cuts the DNA once at a site 142 bp beyond the 3' end of the NOS-NPTII'-NOS gene. This DNA was mixed with 5 µg of pMON344 DNA that had been cleaved at its unique SmaI site located in the pUC18 synthetic multilinker. Following ligation and transformation of pM294 cells, 56 colonies resistant to both ampicillin and spectinomycin were obtained. Plasmid mini-preps were made from 12 of these and screened for the correct structure by digestion with BamHI, EcoRI, BglII and NdeI for the correct orientation shown in FIGS. 6 and 7. One of these plasmids was saved and named pMON352.

EXAMPLE 5

The following example demonstrates the construction of a geminivirus plant plasmid vector (pMON358), in particular, a TGMV-A component plant plasmid vector, for use in a free DNA delivery system. Also demonstrated is the construction of a negative control vector (pMON360) lacking the TGMV-A DNA sequences for use in free DNA delivery systems.

a. Construction of pMON358

Plasmid pMON352 DNA (1 µg) was digested with HpaI, diluted 5-fold and treated with DNA ligase. Following transformation of MM294 cells, 2000 ampicillin-resistant colonies were obtained. Sixty-five of these colonies were streaked on plates containing 50 µg/ml spectinomycin. None of the colonies were spectinomycin resistant. DNA mini-preps were made from 12 of these colonies and digested with HpaI and HindIII. Eleven of the colonies contained the 2.6 kb HindIII fragment and a single HpaI site. One of these was saved and called pMON358 (FIG. 8).

b. Construction of pMON360

Plasmid pMON358 DNA (1 µg) was digested with HindIII, diluted five-fold and treated with DNA ligase. Following transformation of pMON294 cells, about 2000 ampicillin resistant colonies were obtained. Plasmid DNA mini-preps were made from twelve of these and digested with HindIII. Eleven of the twelve had a single HindIII site and had lost the 2.6 kb HindIII fragment. One of these was saved and called pMON360 (FIG. 8).

EXAMPLE 6

The following example demonstrates the construction of various intermediate plasmids which provide for assembly of the geminivirus expression vector pMON378 useful in free DNA delivery systems. pMON378 can be cleaved with BglII and SacI to remove the CAT DNA coding sequence and provide an insertion site for any desired DNA coding sequence into the geminivius expression vector pMON378.

a. Construction of pUC8NL

Plasmid pUC8 (Vieira and Messing, 1982) obtained from Bethesda Research Laboratories, Inc. Gaithersburg, Md., DNA (1 µg) was digested with EcoRI and HindIII. Next 40 ng of a synthetic multilinker constructed with EcoRI and HindIII cohesive termini was added and the mixture was treated with DNA ligase. Following transformation of JM101 and selection of white colonies on plates containing ampicillin, Xgal and IPTG, approximately 500 colonies were obtained. DNA mini-preps were made from twelve of these colonies and tested by digestion for the presence of unique EcoRI, HindIII, ClaI, BglII, SacI and XhoI sites. One plasmid showing these properties was saved and called pUC8NL (FIG. 9).

b. Construction of pMON368

Plasmid pUC8NL DNA (1 µg) was digested with NdeI and treated with mungbean nuclease to remove the single strand ends. Following treatment with DNA ligase and transformation of *E. coli* MM294 cells, 200 ampicillin resistant colonies were obtained. DNA mini-preps were made from twelve of these colonies and screened for the loss of the unique NdeI site. One plasmid that had lost the NdeI site was saved and called pMON368 (FIG. 9).

c. Construction of pMON371

Plasmid pMON295 is a derivative of pMON200 that carries a 320 bp DNA fragment derived from the 35S promoter region cauliflower mosaic virus. The sequence of this fragment appears below and its construction is described in Rogers et al. (1985).

```
     EcoRI  Sau3A
1           |                                                           66
5'-GAATTCCCGATCcTATCTGTCACTTCATCAAAAGGACAGTAGAAAAGGAAGGTGGCACTACAAATG 67                                                                     136
   CCATCATTGCGATAAAGGAAAGGCTATCGTTCAAGATGCCTCTGCCGACAGTGGTCCCAAAGATGGACCC 137                                                                    206
   CCACCCACGAGGAGCATCGTGGAAAAAGAAGACGTTCCAACCACGTCTTCAAAGCAAGTGGATTGATGTG

TATA
207                                                            |       276
   ATATCTCCACTGACGTAAGGGATGACGCACAATCCCACTATCCTTCGCAAGACCCTTCCTCTATATAAGG

5' mRNA                          Sau3A
277                |                              |    334
   AAGTTCATTTCATTTGGAGAGGACACGCTGAAATCACCAGTCTCTCTCTACAGATCT-3'
```

The numbering of the CaMV 35S promoter sequence from 5' to 3' for diagrammatic purposes only.

Plasmid pMON295 DNA (20 μg) was digested with 40 units each of BglII and EcoRI. The resultant 330 bp fragment was then purified using the NA-45 membrane method and the purified fragment was digested with 10 units of Sau3A. The Sau3A digested fragment was mixed with 1 μg of pMON368 DNA that had been digested with BglII (5 units) and treated with calf alkaline phosphatase. Following ligation and transformation of E. coli MM294 cells, 100 ampicillin resistant colonies were obtained. DNA mini-preps were made from twelve of these and digested with PvuII to demonstrate the presence of a 330 bp insert and with BglII, EcoRV and XmnI to determine the orientation of the inserted fragment. Two of the twelve contained the 35S promoter fragment in the orientation with the BglII site nearest the HindIII site of pMON368. One of these was saved and called pMON371 (FIG. 9).

d. Construction of pMON369

Plasmid pMON505 DNA (2 μg) was digested with EcoRI (10 units) and treated with the large Klenow fragment of E. coli DNA polymerase in the presence of the four deoxynucleotide triphosphates. Following ligation and transformation of E. coli MM294, about 500 spectinomycin resistant colonies were obtained. Plasmid mini-preps were made from twelve of these and digested with EcoRI. One of the twelve had lost the EcoRI site and was saved. This plasmid was called pMON369 (FIG. 10).

e. Construction of pMON373

Twenty micrograms of plasmid pMON369 DNA prepared from E. coli GM48 dam⁻ cells was digested with 20 units of ClaI and the 1.6 kb fragment carrying the NOS-NPTII'-NOS kanamycin resistance gene was purified using the NA-45 membrane procedure. The purified fragment (1 μg) was mixed with 1 μg of pMON371 DNA that had been digested with 2 units of ClaI and treated with calf alkaline phosphatase. After ligation and transformation of E. coli MM294 cells, about 800 ampicillin resistant colonies were obtained. DNA mini-preps were made from twelve of these and digested with ClaI and BglII to show the presence of the 1.6 kb fragment and its orientation. One of these plasmids that showed the correct structure was saved and called pMON373 (FIG. 10).

f. Construction of pMON370

Plasmid pMON344 (FIG. 5) DNA (1 μg) was digested with DraI, an isoschizomer of AhaIII, mixed with 40 ng of synthetic ClaI linkers (5'pCATCGATG, New England Biolabs, Beverly, Mass.) and treated with DNA ligase. After digestion of the ligation mixture with ClaI (50 units) these DNA fragments were added to pMON316 DNA (1 μg) that had been cleaved with ClaI and treated with calf alkaline phosphatase. Following ligation and transformation, 500 spectinomycin resistant colonies were obtained. DNA mini-preps were made from twelve of these colonies and digested with ClaI. One of these plasmids carried a 1 kb ClaI fragment that contained an EcoRI and NcoI site. This plasmid was saved and called pMON370 (FIG. 10).

g. Construction of pMON374

Plasmid pMON370 DNA (5 μg) was digested with ClaI (20 units) and mixed with 0.2 μg of pMON373 DNA that had been digested with ClaI (2 units) and treated with calf alkaline phosphatase. Following ligation and transformation of E. coli MM294 cells, 300 ampicillin resistant colonies were obtained. DNA mini-preps were made from twelve of these colonies that were selected for sensitivity to spectinomycin. Six of the colonies carried the 1 kb ClaI fragment. Screening by digestion with EcoRI showed that four of these plasmids carried the ClaI fragment in the orientation shown in FIG. 12. One of these was saved and called pMON374.

h. Construction of pMON550

Plasmid pUC19 (Yanisch-Perron et al., 1985) DNA (1 μg) was digested with HindIII (2 units) and EcoRI (2 units) and mixed with 50 ng of a synthetic DNA multilinker (FIG. 11). Following ligation and transformation of E. coli JM101 cells, about 500 colonies were obtain on ampicillin, Xgal and IPTG plates. DNA mini-preps were made from twelve of the blue colonies and digested with EcoRI, BglII, NcoI, SacI and HindIII. One plasmid containing unique sites for these endonucleases was saved and called pMON550 (FIG. 11).

i. Construction of pMON375

Plasmid pMON2414 (FIG. 12) DNA (20 μg) was digested with NcoI (50 units) and the 940 bp fragment carrying the chloramphenicol acetyl transferase (CAT) coding sequence was purified using the NA-45 membrane method. The fragment (2 μg) was mixed with plasmid pMON550 DNA (1 μg) that was previously digested with NcoI (5 units) and treated with calf alkaline phosphatase. Following ligation and transformation of E. coli MM294 cells, about 500 ampicillin colonies were obtained. DNA mini-preps were made from twelve of these. The same twelve colonies were tested for chloramphenicol resistance on LB plates containing 25 μg/ml chloramphenicol. Six of these colonies were resistant to chloramphenicol. These same six carried the 940 bp NcoI fragment in the pMON550 plasmid in the orientation shown in FIG. 12. One of these plasmids was saved and called pMON375.

j. Construction of pMON377

Plasmid pMON375 DNA (50 μg) was digested with SacI (50 units) and BglII (50 units) and the resulting 960 bp fragment carrying the CAT coding sequence was purified using the NA-45 membrane procedure. This BglII-SacI fragment (lug) was mixed with 1 μg of pMON374 DNA that had been digested with BglII (5 units) and SacI (3 units). Following ligation and transformation of *E. coli* MM294 cells, ampicillin resistant colonies were obtained. These colonies were tested for resistance to 25 μg/ml chloramphenicol. DNA mini-preps were made from twelve of these DNAs and analyzed by BglII and SacI digestion for the presence of the 960 bp CAT fragment. One of the plasmids showing the correct structure (FIG. 12) was saved and called pMON377.

k. Construction of pMON376

Plasmid pMON344 (FIGS. 5 and 13) DNA (5 μg) was digested with SmaI (10 units) and AsuII (10 units) and treated with the large Klenow fragment of DNA polymerase. Following ligation and transformation of *E. coli* MM294 cells, one ampicillin resistant colony was obtained. A DNA mini-prep was made and digested with SmaI, HindIII and SphI to test for deletion of the SmaI to AsuII fragment. It showed the correct structure was saved and called pMON376 (FIG. 13).

l. Construction of pMON378

Plasmid pMON376 DNA (20 μg) was digested with HindIII (20 units) and SacI (20 units) and the resulting TGMV-A 2.5 kb fragment was purified by the NA-45 membrane procedure and mixed with pMON377 DNA (1 μg) that had been digested with HindIII and SacI. Following ligation and transformation, ampicillin resistant colonies were obtained. DNA mini-preps were made from twelve of these colonies and digested with SacI and HindIII and EcoRI. One of the plasmids showing the correct insert and two EcoRI sites located 5.4 kb apart was saved and named pMON378 (FIGS. 13 and 14).

EXAMPLE 7

The following example demonstrates the construction of plasmid pMON380 via an intermediate plasmid pMON379. pMON380 carries a TGMV-A component in which every major known reading frame has been interrupted. pMON380 is useful as a negative control in free DNA delivery systems as the TGMV-A DNA so delivered should be unable to replicate in transformed plant cells.

a. Construction of pMON379

One μg of plasmid pMON376 DNA was digested with ClaI (2 units) and BamHI (2 units) and treated with the large Klenow fragment of DNA polymerase. Following ligation and transformation of *E. coli* MM294 cells, ampicillin resistant colonies were obtained. DNA mini-preps were made from twelve of the colonies and digested BamHI which cleaves the deletion derivative and with ClaI, which does not cut the desired deletion derivative, prepared in a dam+ cell like *E. coli* MM294, and HindIII and SacI to identify the deleted fragment which was approximately 1.9 kb in size. One of the plasmids with these characteristics was saved and named pMON379 (FIG. 15).

b. Construction of pMON380

Plasmid pMON379 DNA (20 μg) was digested with SacI (20 units) and HindIII (20 units) and the resulting 1.9 kb fragment purified using the NA-45 membrane procedure. The fragment (3 μg) was mixed with 1 μg of pMON377 DNA that had been digested with SacI (2 units) and HindIII (2 units). Following ligation and transformation, ampicillin resistant colonies were obtained. DNA mini-preps were made from twelve of these colonies analyzed for the presence of the 1.9 kb SacI-HindIII fragment. One of the plasmids showing this structure was saved and called pMON380 (FIG. 15).

EXAMPLE 8

The following example demonstrates the construction of various intermediate vectors which provide for the conversion of pMON378, useful as a vector for free DNA delivery systems, to pMON382, useful as a plant plasmid vector for Ti delivery systems. Specifically, the pUC DNA sequences carried on pMON378 were replaced with pMON505 DNA sequences.

a. Construction of pMON521

Figure 16:
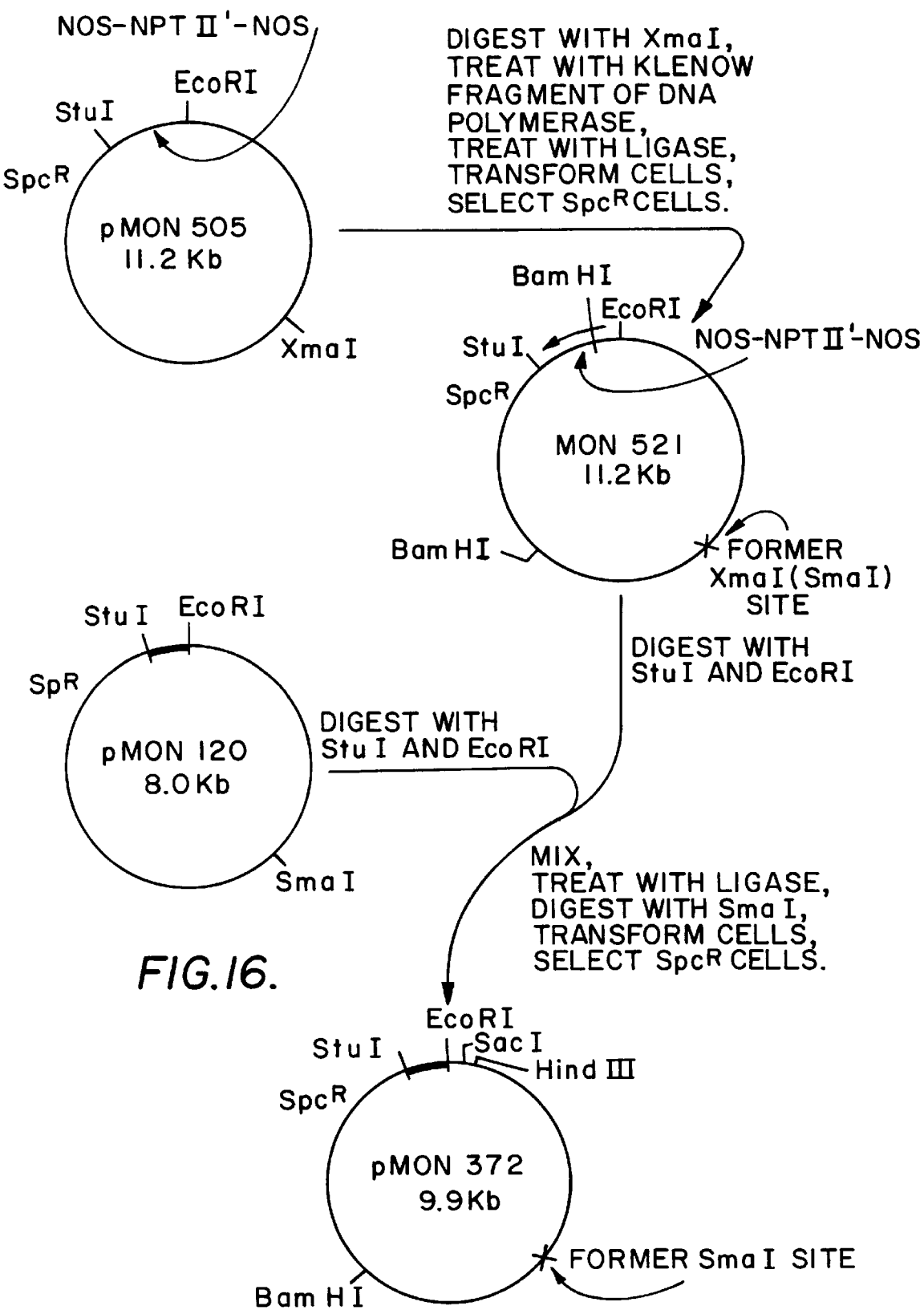
FIG. 16 depicts the construction of pMON372 comprising pMON505 modified to remove its XmaI (SmaI) site and thereafter having inserted therein in place of its StuI-EcoRI fragment carrying the NOS-NPTII'-NOS DNA sequence, a StuI-EcoRI fragment obtained from pMON120. The blackened area on pMON372 represents the StuI-EcoRI fragment from pMON120.

Plasmid pMON505 DNA (1 μg) was digested with XmaI (2 units) and treated with the large Klenow fragment of DNA polymerase. Following ligation and transformation of JM101 cells, 80 spectinomycin resistant colonies were obtained. DNA mini-preps were made from twelve of these colonies and digested with SmaI to show loss of the SmaI (XmaI) site. One of the plasmids that had lost the SmaI site was saved and called pMON521 (FIG. 16).

b. Construction of pMON372

Plasmid pMON120 (Fraley et al., 1983) DNA (20 μg) was digested with StuI (20 units) and EcoRI (20 units) and mixed with 1 μg of pMON521 that was digested with StuI (2 units) and EcoRI (2 units). Following ligation the mixture was digested with 20 units of SmaI and used to transform *E. coli* MM294 cells. Over 400 spectinomycin resistant colonies were obtained. DNA mini-preps were made from twelve of these colonies and screened for the absence of an SmaI site and loss of the 1.6 kb NOS-NPTII'-NOS fragment by absence of a second BamHI site. One of these plasmids showing the correct structure was saved and called pMON372 (FIG. 16).

c. Construction of pMON381

Plasmid pMON377 DNA (20 μg) was digested with SacI (20 units) and EcoRI (20 units) and the larger 3.5 kb fragment purified using the NA-45 membrane procedure. Five μg of the purified fragment was then be mixed with 1 μg of pMON372 DNA that had been cleaved with EcoRI (2 units) and SacI (2 units) and treated with DNA ligase. Following transformation of *E. coli* MM294 cells, about 100 spectinomycin resistant colonies were obtained. DNA mini-preps were made from twelve of these colonies and digested with EcoRI and SacI to show the presence of the 3.5 kb insert. One of the plasmids carrying the insert was saved and called pMON381 (FIG. 20).

d. Construction of pMON382

Plasmid pMON376 DNA (20 μg) was digested with HindIII (20 units) and SacI (20 units) and the resultant 2.5 kb fragment was purified using the NA-45 membrane procedure. Two μg of the fragment was mixed with pMON381 DNA (1 μg) that had been cleaved with two units each of HindIII and SacI. Following ligation and transformation of E. coli MM294 cells, spectinomycin resistant colonies were obtained. DNA mini-preps were made from twelve of these colonies and digested with HindIII and SacI to demonstrate the presence of the 2.5 kb insert. One of the plasmids with the insert was saved and called pMON382 (FIGS. 17 and 18).

EXAMPLE 9

The following example demonstrates the construction of a vector which was employed as a negative control in the Ti plasmid delivery system. Specifically, pMON383 carries a TGMV-A DNA which has been deleted in portions of the AL1, AL2 and AL3 open reading frame coding information.

a. Construction of pMON383

Plasmid pMON379 DNA (20 μg) was digested with HindIII (20 units) and SacI (20 units) and the resultant 1.9 kb fragment was purified using the NA-45 membrane procedure. Two μg of the 1.9 kb fragment was mixed with one μg of pMON381 DNA that had been digested with HindIII (1 unit) and SacI (2 units). Following ligation and transformation of E. coli MM294 cells, spectinomycin resistant colonies were obtained. DNA mini-preps were made from twelve of these and digested with HindIII and SacI to demonstrate the presence of the 1.9 kb insert. One of the plasmids with the insert was saved and called pMON383 (FIG. 19).

EXAMPLE 10

The following example demonstrates the construction of pMON417 comprising a Ti plasmid having inserted therein a TGMV-A DNA carrying a CAT gene in place of its coat protein gene and wherein the TGMV-A DNA is flanked by directly repeating DNA segments.

a. Construction of pMON333

Figure 23:
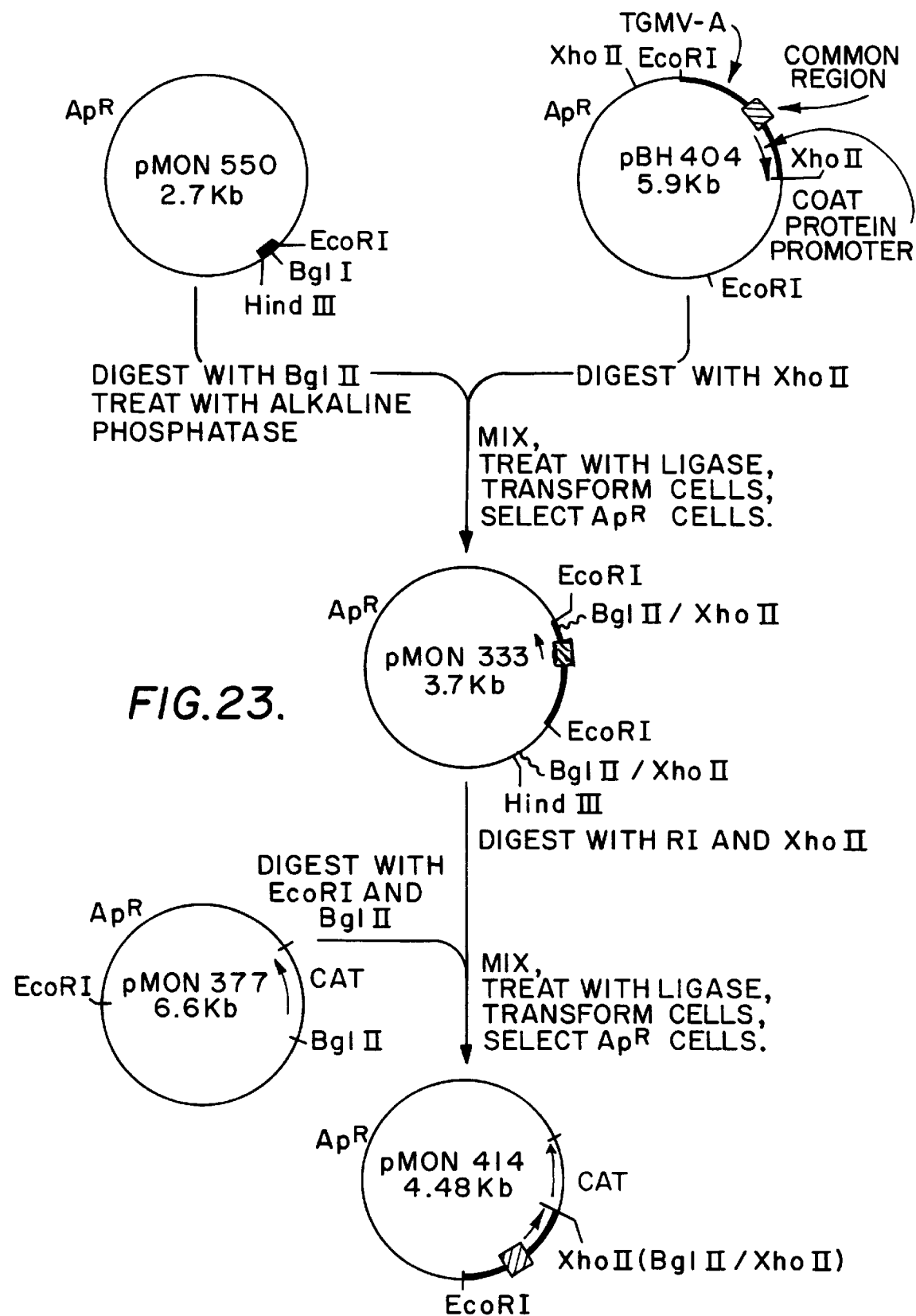
FIG. 23 depicts the construction of pMON414 comprising pMON505 having inserted therein a segment of TGMV-A DNA including the TGMV coat protein promoter and the TGMV common region and a chloramphenicol acetyl transferase (CAT) gene. The blackened line denotes TGMV-A DNA and the hatched box denotes the TGMV common region.

Two micrograms of pMON550 was digested with five units of BglII, treated with calf alkaline phosphatase, and combined with two micrograms of pBH404 which had been digested with ten units of XhoII. After treatment with DNA ligase and transformation into E. coli MM394 cells, 200 ampicillin resistant were obtained. Twelve colonies were screened by restriction analysis and one which showed the correct construct was saved and designated pMON333 (FIG. 23).

b. Construction of pMON414

Five micrograms of plasmid pMON333 DNA was digested with 10 units of EcoRI and 10 units of XhoII, treated with calf alkaline phosphatase and combined with five micrograms of pMON377 DNA digested with 10 units each EcoRI and BglII, treated with DNA ligase and used to transform E. coli MM294 cells. Twelve out of 173 ampicillin resistant colonies were subjected to alkaline lysis and screened by restriction analysis. One colony that showed the correct pattern was saved and designated pMON414 (FIG. 23).

c. Construction of pMON351

Figure 24B:
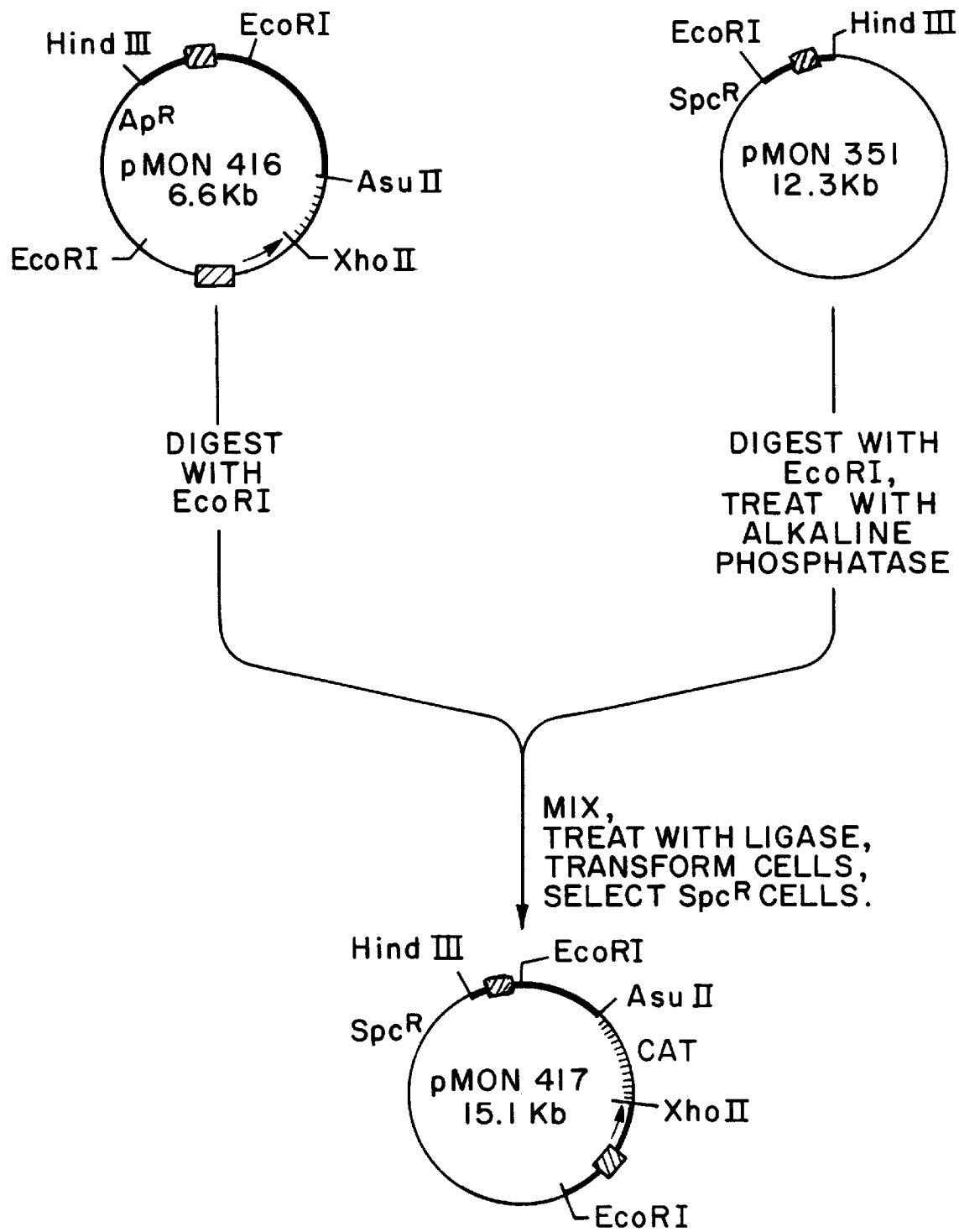

Two micrograms of pMON345 DNA was digested with five units of EcoRI, diluted five-fold, treated with DNA ligase and used to transform E. coli MM294 cells. Mini-prep DNA from 12 of approximately 250 spectinomycin resistant colonies was screened for the loss of a 2.8 kb EcoRI fragment. One colony which had lost the fragment was saved and designated pMON351 (FIG. 24).

d. Construction of pMON416

Five micrograms of pMON414 DNA was digested with 10 units each HindIII and AsuII, mixed with five micrograms of pMON344 previously digested with 10 units each HindIII and AsuII; treated with DNA ligase and used to transform E. coli MM294 cells selecting for ampicillin resistance. Twelve out of 300 colonies were subjected to alkaline lysis and restriction enzyme analysis. One colony having the correct restriction pattern was saved and designated pMON416 (FIG. 24).

e. Construction of pMON417

Figure 25:
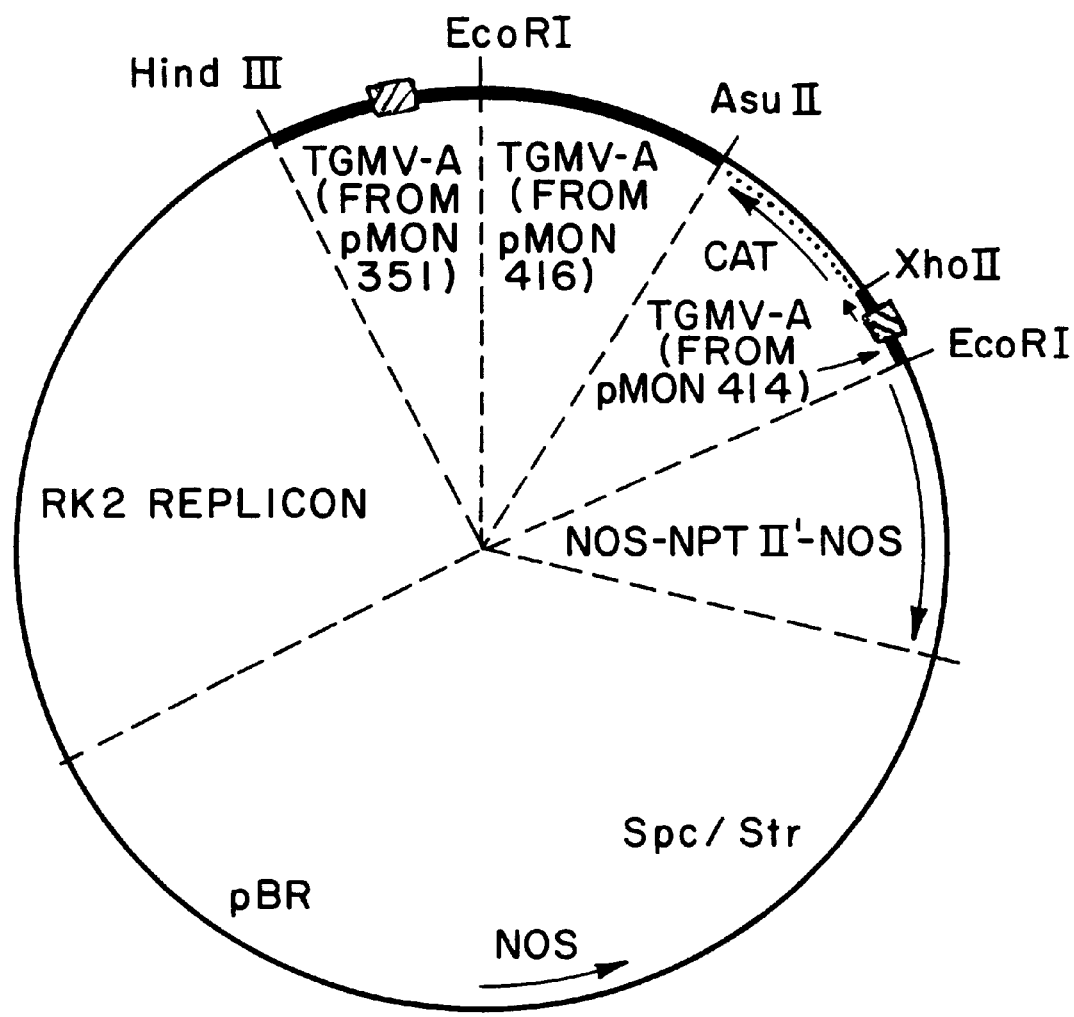
FIG. 25 depicts pMON417 wherein the relevant DNA sequences are identified as labeled thereon.

Five micrograms of pMON351 DNA was digested with 10 units of EcoRI, treated with calf alkaline phosphatase and combined in the presence of DNA ligase with five micrograms of pMON416 DNA digested with 10 units of EcoRI. Following ligation, transformation of E. coli MM294 cells yielded 300 spectinomycin resistance colonies. Twelve of these colonies were screened by restriction enzyme analysis and one of these with the correct pattern was saved and was designated pMON417 (FIGS. 24 and 25).

EXAMPLE 11

This example demonstrates the construction of pMON354 comprising a gene able to cause expression of a DNA sequence coding for a protein able to confer methotrexate resistance in cells transformed therewith flanked by directly repeating DNA segments comprising TGMV-A DNA sequences or a portion thereof. The construction of various intermediate vectors are also described.

a. Construction of pMON800

Figure 26:
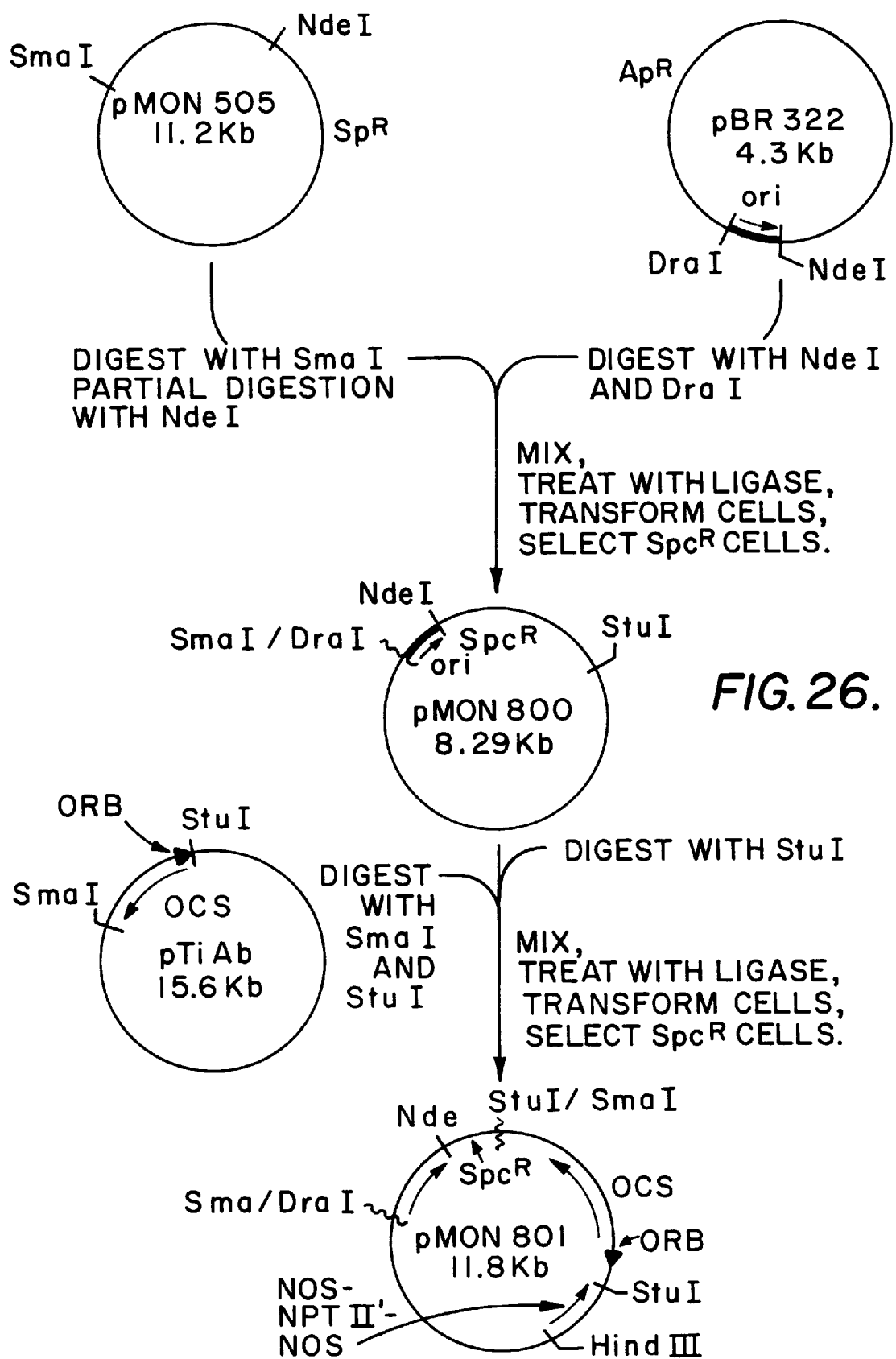
FIG. 26 depicts the construction of pMON801 comprising pMON505 having inserted therein an origin of replication (ori) for pBR322, an octopine synthase (OCS) gene and a octopine-type $T_L$ T-DNA right border sequence (ORB) wherein the ORB is denoted by the blackened triangle.

Ten micrograms of pMON505 (FIG. 5) DNA was digested to completion with SmaI and partially with NdeI and a resulting 7.3 kb fragment was joined to the pBR322 0.9 kb NdeI (nucleotide number, n.,2297) to DraI (n. 3232) fragment. The nucleotide numbers are from the sequence of Sutcliff (1978). Following ligation and transformation of competent JM101 cells one plasmid was identified that contained these two fragments joined together. This plasmid was saved and called pMON800 (FIG. 26).

b. Construction of pMON801

A 3.5 kb SmaI (n. 11207) to StuI (n. 14675) fragment of pTiA6 containing the octopine synthase gene and octopine T-DNA TL right border sequence was inserted into the unique StuI site of pMON800. pTiA6 is an octopine-type Ti plasmid. Thus, equivalent DNA fragments containing the octopine synthase gene and octopine T-DNA TL right boarder can be obtained from such alternative octopine-type Ti plasmids as pTiB6S3, pTiACH5 or pTi15955. The nucleotide numbers are from the sequence of Barker et al. (1983). Following transformation of JM101 cells and selection for spectinomycin resistant transformants, a clone was identified that carried the pTiA6 fragment in the correct orientation (FIG. 26). This plasmid was called pMON801.

c. Construction of pMON809

Figure 27:
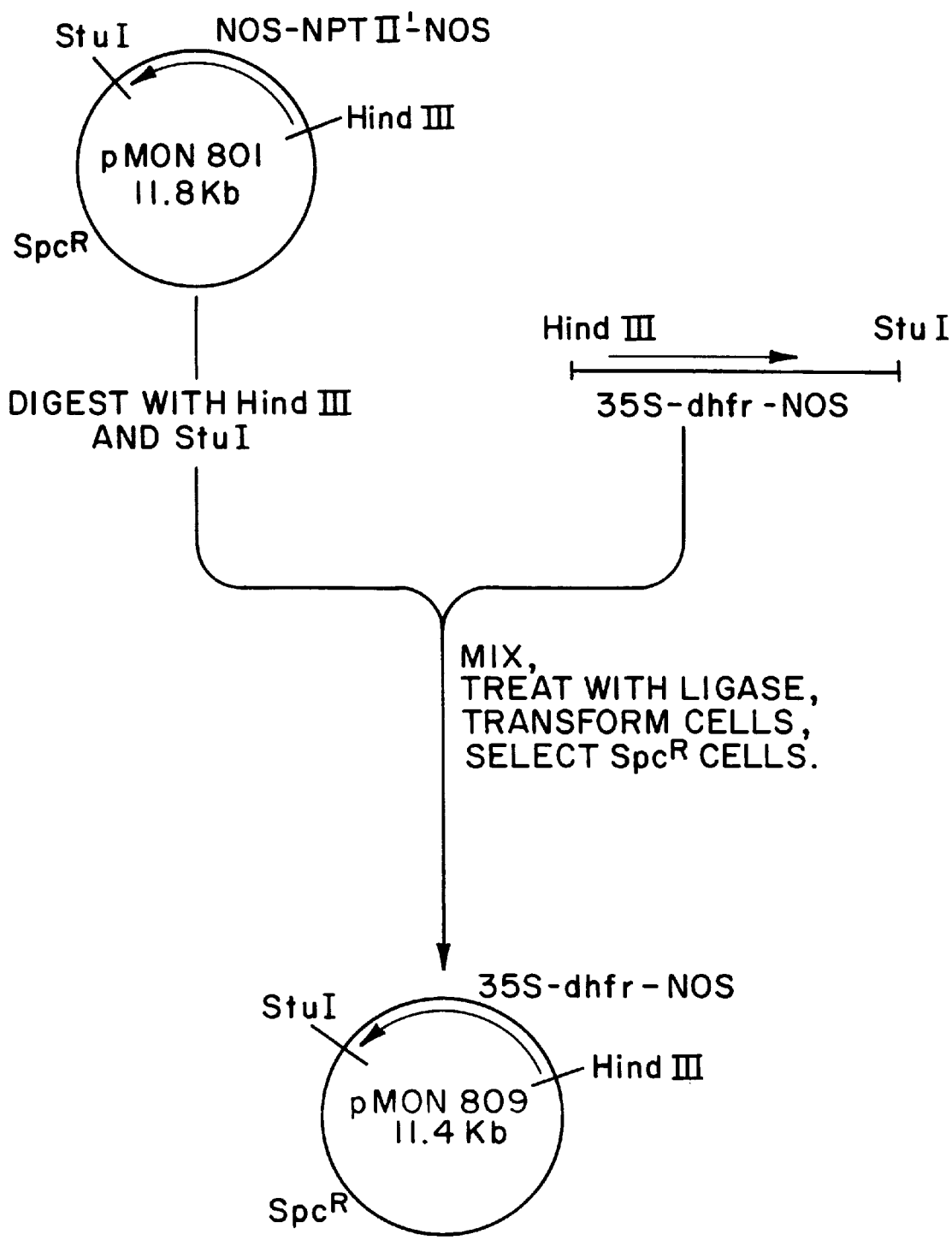
FIG. 27 depicts the construction of pMON809 comprising pMON801 in which the NOS-NPTII'-NOS DNA sequence has been replaced with a DNA fragment containing a 35S promoter sequence (35S), a dihydrofolate reductase coding sequence (dhfr) and a nopaline synthase 3' non-coding sequence (NOS).

The 1.8 kb StuI to HindIII fragment of pMON801 which encodes the chimeric NOS-NPTII'-NOS kanamycin resistance gene was replaced with a 1.4 kb StuI-HindIII fragment carrying a chimeric methotrexate resistance gene. This chimeric gene consists of the CaMV 35S promoter from pMON295 (FIG. 12) joined to a 660 bp fragment carrying a mouse di-hydrofolate reductase (dhfr) coding sequence which encodes a methotrexate resistant dhfr enzyme. Polyadenylation signals are provided by the NOS 3' non-translated region. The resulting plasmid was called pMON809 (FIG. 27).

d. Construction of pMON347

Figure 28:
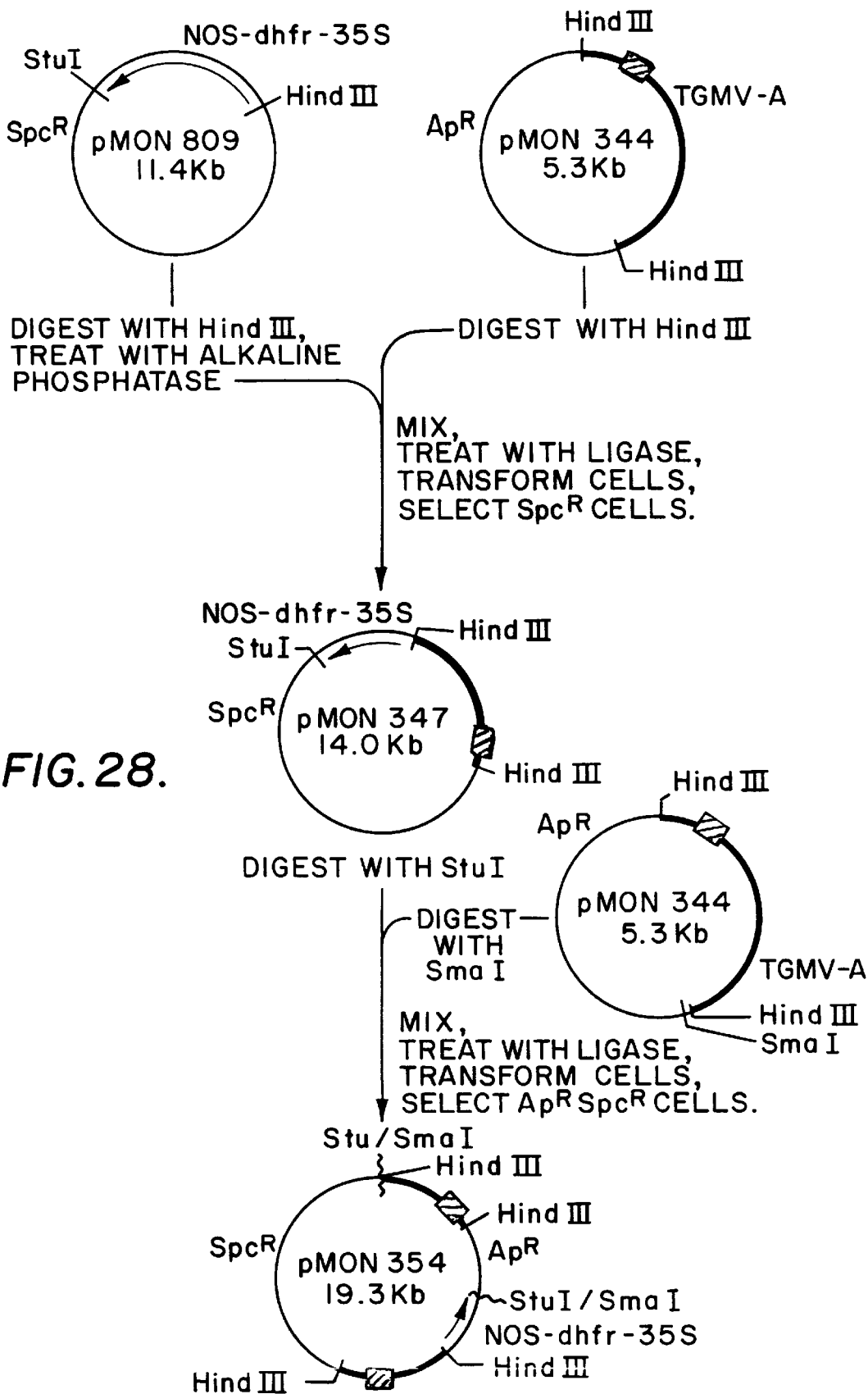
FIG. 28 depicts the construction of pMON354 comprising pMON505 having inserted therein an expression cassette comprising a 35S promoter sequence (35S), a dihydrofolate reductase coding sequence (dhfr) and a nopaline synthase coding sequence (NOS) and wherein the expression cassette is flanked by TGMV-A DNA, denoted by the blackened line. The hatched box denotes the common region.

Five micrograms of plasmid pMON809 was digested with HindIII and treated with calf alkaline phosphatase. Five micrograms of plasmid pMON344 DNA was digested with HindIII and mixed with HindIII-digested pMON809 DNA, treated with DNA ligase and used to transform competent *E. coli* MM294 cells. Approximately 130 ampicillin colonies were obtained; 12 of which were subjected to alkaline lysis and restriction analysis. One of these plasmids which showed the correct structure was saved and designated pMON347 (FIG. 28).

e. Construction of pMON354

Five micrograms of pMON347 DNA prepared from *E. coli* GM48 dcm⁻ cells was digested with 10 units of StuI and mixed with five micrograms of pMON344 DNA digested with 10 units of SmaI. After treatment with DNA ligase, the mixture was used to transform MM294 cells. Fifty ampicillin-spectinomycin resistant colonies were obtained and 12 of these were subjected to alkaline lysis and restriction analysis. One of these which showed the correct structure was saved and designated pMON354 (FIG. 28).

EXAMPLE 12

The following example demonstrates the construction of pMON337 comprising a pMON505 vector having inserted therein at an EcoRI site a complete copy of the TGMV-A component contiguous with a TGMV common region. This Example 12 also demonstrates the construction of pMON341 comprising a pMON505 vector having inserted therein a complete copy of the TGMV-A component contiguous with a TGMV-A DNA sequence that does not contain a TGMV common region. The construction of various intermediate vectors are also described.

a. Construction of pMON337

Figure 29:
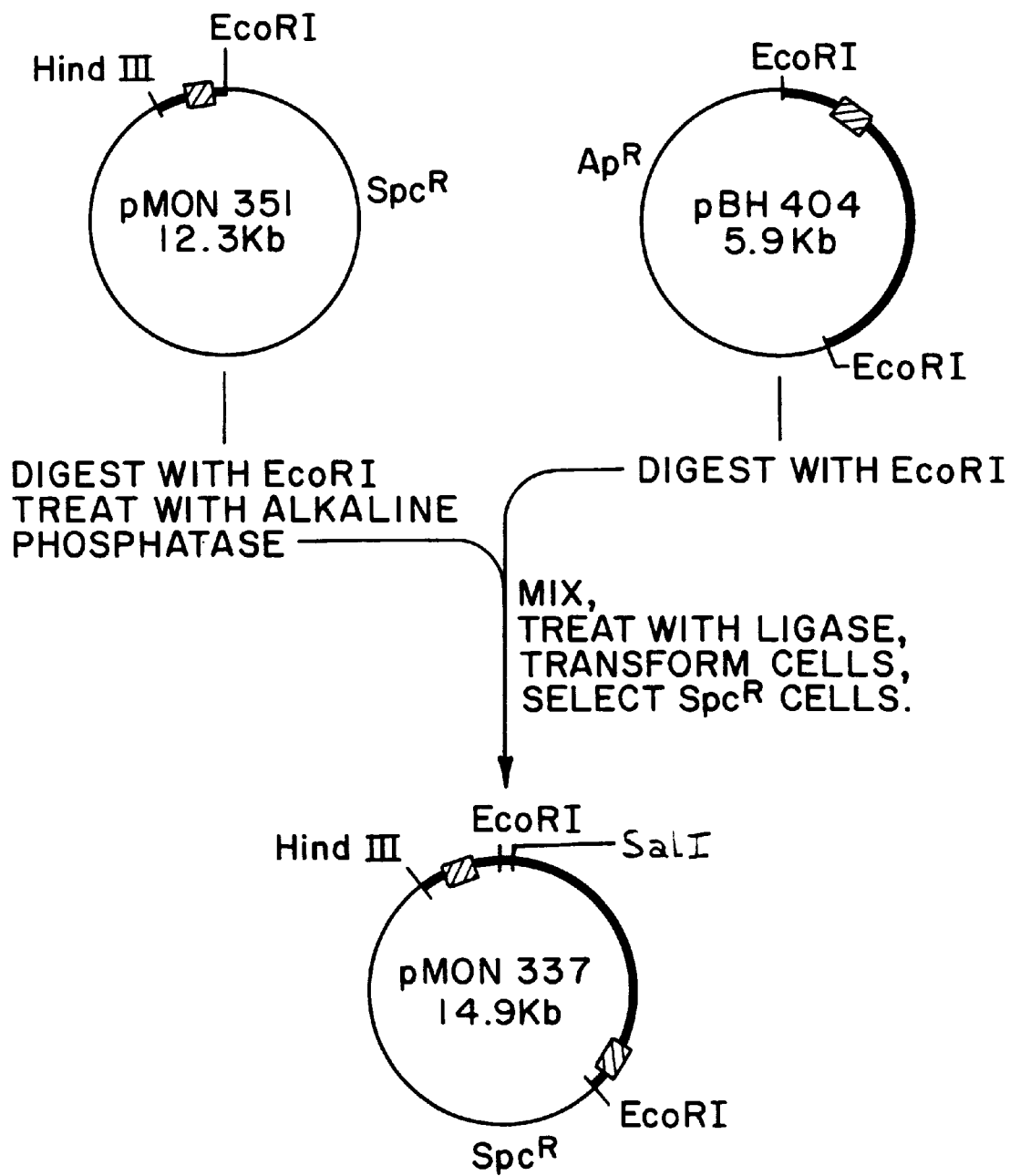
FIG. 29 depicts the construction of pMON337 comprising pMON505 having inserted therein one and one half copies of TGMV-A DNA, denoted by the blackened line. The TGMV common region is denoted by a hatched box.

Five micrograms of pMON351 DNA was digested with 10 units of EcoRI, treated with calf alkaline phosphatase and combined in the presence of DNA ligase with five micrograms of pBH404 DNA digested with 10 units of EcoRI. Following ligation, transformation of *E. coli* MM294 cells yielded 50 spectinomycin resistant colonies. Twelve of these colonies were screened by restriction enzyme analysis and one of these with the 2.6 kb TGMV-A EcoRI insert of pBH404 in pMON351 in the same orientation as the TGMV-A sequences present in pMON351 was saved and designated pMON337 (FIG. 29).

b. Construction of pMON346

Ten micrograms of pMON505 (FIG. 5) DNA was digested to completion with HindIII, treated with alkaline phosphatase, and ligated with ten micrograms of pMON344 DNA digested with HindIII. Transformation of competent MM294 cells yielded 50 spectinomycin resistant colonies. Twelve of these colonies were screened by restriction enzyme analysis and one of these with the 2.6 kb TGMV-A HindIII insert of pMON344 in pMON505 was saved and designated pMON346.

c. Construction of pMON336

Figure 30:
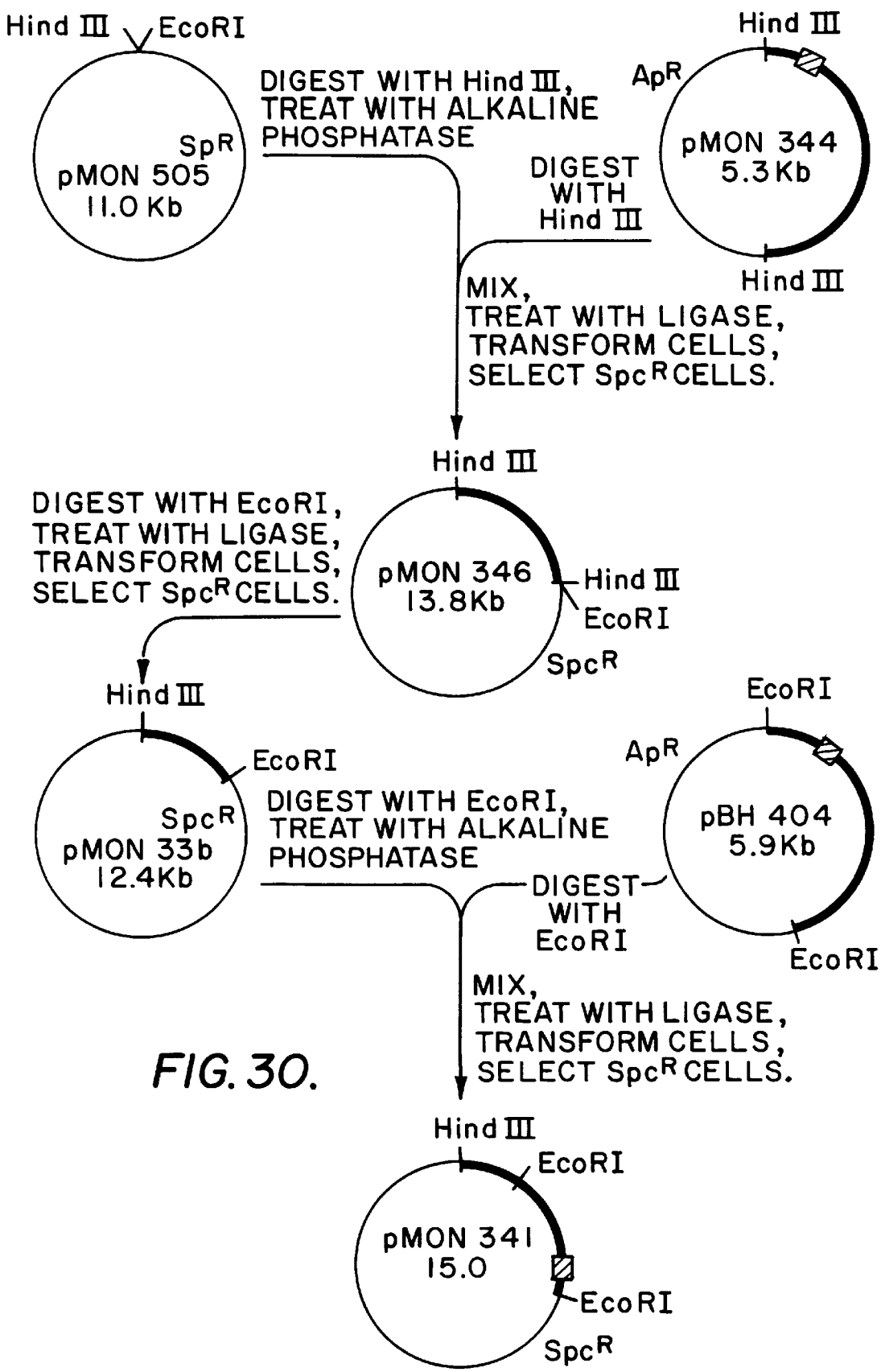
FIG. 30 depicts the construction of pMON341 comprising pMON505 having inserted therein one and one half copies of TGMV-A DNA, denoted by the blackened line. The TGMV common region is denoted by the hatched box.

Ten micrograms of pMON346 DNA was digested to completion with EcoRI. Ligation of this DNA and transformation into competent MM294 cells yielded 50 spectinomycin resistant colonies. Twelve of these colonies were screened by restriction analysis and one of these which had lost a 1.4 kb EcoRI fragment was saved and called pMON336 (FIG. 30).

d. Construction of pMON341

Ten micrograms of pMON336 was digested with EcoRI, treated with alkaline phosphatase, and combined in the presence of DNA ligase with five micrograms of pBH404 DNA digested with 10 units of EcoRI. Following ligation, transformation of *E. coli* MM294 cells yielded 50 spectinomycin resistant colonies. Twelve of these colonies were screened by restriction enzyme analysis and one of these with the 2.6 kb TGMV-A EcoRI insert of pBH404 in pMON336 (in the same orientation as the TGMV-A sequences present in pMON336) was saved and designated pMON341 (FIG. 30).

EXAMPLE 13

The following example demonstrates the creation and selection of plant cells transformed with various geminivirus vectors of the present invention. This example further demonstrates the replication and expression in plant cells of heterologous DNA sequences employing the geminivirus plant plasmids of the present invention.

a. Transformation of Petunia Cells

Leaf discs with diameters of 6 mm (¼ inch) were taken from surface-sterilized petunia (*Petunia hybrida*) leaves. They were cultivated on MS104 agar medium for 2 days to promote partial cell wall formation at the wound surface. They were then submerged in a culture of *A. tumefaciens* cells containing the disarmed pTiB6S3-SE and either pMON305, pMON337, pMON341, pMON352, pMON354, pMON382 or pMON383 which had been grown overnight in Luria broth at 28° C., and shaken gently. The discs were removed from the bacterial suspension, blotted dry, and incubated upside down on MS104 agar medium. After 2 or 3 days, the discs were transferred to selection media containing MS104 medium with 500 μg per ml carbenicillin and either 300 μg per ml kanamycin for the pMON305, pMON337, pMON341, pMON352, pMON382 and pMON383 treated discs or 450 μg/l methotrexate for the pMON354 treated discs. Cefatoxine, 500 μg/ml, was added to the medium used to select for discs transformed with pMON352 or pMON354 b. Transformation of Tobacco Cells

Leaf segments were excised from tobacco plants (*Nicotiana benthamiana*), and treated as described above for petunia cells with *A. tumefaciens* cells containing pMON200, pMON305, pMON308, pMON309 and helper plasmid pTiB6S3-SE. The cells transformed with these created substantial amounts of kanamycin resistant callus tissue.

c. DNA Analysis

Total DNA was isolated from leaf discs by the method of Dellaporta (1983) 4–10 days after transfer to selection medium. Six discs were used, for a total of 0.5 gm of tissue. This uncut DNA was prepared in accordance with the southern blot hybridization procedure previously described. The $^{32}$P-labeled probe used to identify DNA replicative form contained pUC8 DNA and an insert specific for the TGMV-A component, previously described.

d. Results

The Southern blot analysis of leaf discs treated with *A. tumefaciens* containing pMON352 revealed a band at a position predicted for a freely replicating, ds supercoiled DNA molecule of approximately 7.0 kilobases (kb) comprising a TGMV-A component, a pUC18 fragment containing an ampicillin resistance gene and the NOS-NPTII'-NOS gene. For DNA prepared from leaf discs treated with *A. tume faciens* containing pMON354, the Southern blot analysis revealed a band at a position predicted for a freely replicating, ds supercoiled plasmid DNA molecule of approximately 6.7 kb comprising a TGMV-A component, an ampicillin resistance gene from pUC18 and a DNA sequence comprising the CaMV 35S promoter and DHFR-NOS coding sequences.

Southern blot analysis of DNA obtained from leaf discs treated with *A. tumefaciens* containing pMON382 revealed a band at a position predicted for a freely replicating, ds supercoiled DNAs of approximately 4.6 kb and comprising TGMV-A DNA sequences, a NOS-NPTII'-NOS gene and a CaMV 35S-CAT gene. The 4.6 kb band was also detected by a probes specific for CAT or NOS-NPTII'-NOS DNA sequences. Furthermore, Southern blot analysis of BglII or BamHI digested DNA obtained from leaf discs treated with *A. tumefaciens* containing pMON382 revealed ds linear TGMV-A containing fragments of approximately 4.6 kb for BglII treated DNA and of approximately 2.8 kb and 1.8 kb for BamHI digested DNA as predicted for a freely replicating plant plasmid DNA derived from the pMON382 vector.

Southern blot analysis of DNA obtained from leaf discs treated with *A. tumefaciens* containing pMON337 or pMON341 revealed bands that comigrated with freely replicating, ds "supercoiled" and ss TGMV-A DNAs from TGMV infected plants.

The foregoing results clearly demonstrate the ability of geminivirus-containing vectors to replicate and express heterologous DNA sequences in plant cells. The results further demonstrate that these heterologous DNA sequences can be as large or larger (e.g. 4.3 kb) than the geminivirus genomic DNA sequences replaced thereby and that replication and/or expression of heterologous DNA sequences in plant cells can occur as part of a freely (e.g. autonomously) replicating geminivirus-containing plasmid DNA molecule. Additionally, these results demonstrate the ability of geminivirus DNA, in particular TGMV-A DNA, to release itself from chromosomal and/or T-DNA sequences to form autonomously replicating DNA molecules while still retaining heterologous DNA sequences inserted therein. Also, demonstrated is that interruption and/or deletion of geminivirus coat protein gene sequences does not interfere with the ability of geminivirus coat protein-encoding DNA molecules (e.g. TGMV-A DNA) to replicate autonomously in plant cells transformed therewith.

In all of the foregoing examples which demonstrate heterologous DNA sequence replication in plants in the form of an autonomously replicating plasmid DNA molecule, the heterologous DNA sequences were flanked by directly repeating DNA sequences. In these particular preferred embodiments, the directly repeating DNA sequences comprised geminivirus DNA sequences (e.g. TGMV-A DNA) or a portion therefore. As shown by the successful formation of autonomously replicating TGMV-A DNA molecules derived from pMON341, the presence of geminivirus (e.g. TGMV) common regions in the directly repeating DNA sequences is not essential for plasmid formation. It is therefore anticipated that DNA sequences flanking a geminivirus coat protein-encoding DNA (e.g. TGMV-A DNA) having inserted therein a heterologous DNA sequence can comprise any directly repeating DNA sequence of sufficient length and homology to promote release of autonomously replicating plasmid DNAs from chromosomal and/or vector DNA molecules detectable by the methods described herein. It is further anticipated that variants of these vector molecules and resultant plasmid DNA molecules produced therefrom can be constructed and are considered to be equivalents of the embodiments described herein.

EXAMPLE 14

The following example demonstrates the mobility of a geminivirus vector of the present invention in transformed plants and the ability of such mobile vectors to replicate and express a heterologous DNA sequence in plant cell tissue distinct from the site of inoculation. Specifically, pMON417 comprising TGMV-A DNA having inserted therein a CAT gene was employed to inoculate decapitated plants previously transformed with TGMV-B DNA.

Both wildtype *Nicotiana benthamiana* plants and ones containing tandem integrated copies of the TGMV-B components (B plants) prepared as described in Example 1, above, were grown in soil until several leaves were present (2–4 weeks). At this stage the upper half of each plant was removed by cutting the stem with a razor blade leaving 2–3 leaves remaining. Immediately after cutting, Agrobacterium containing pMON417 (grown on nutrient plates) was spread on the top of the freshly wounded stem of each plant using a sterile toothpick. Leaf tissue was taken from both the wildtype and B plants for DNA analysis and assay of CAT activity when chlorotic spots became present on the newly emerged leaves of the innoculated B plants (2–4 weeks). Leaves of stem inoculated wildtype plants remained normal in appearance for several weeks until they were discarded.

Total DNA was isolated from leaf tissue using the technique described by Dellaporta et al. (1983). This uncut DNA was then electrophoresed on 0.8% (w/v) agarose gel, blotted onto nitrocellulose, and hybridized to a probe specific for the TGMV-A component in accordance with the Southern blot procedure previously described. Hybridization to bands associated with autonomously replicating TGMV-A components of both ds and ss forms was observed in DNA from leaves of the stem inoculated B plants. No hybridization was observed in DNA from leaves of stem inoculated wildtype plants. This results demonstrates the ability of the TGMV-A component containing a foreign gene (e.g. CAT) to replicate autonomously and move from cell to cell in plants containing integrated copies of the B component.

Furthermore, in addition to providing for autonomous replication and movement of heterologous DNA sequences in plants, the vectors of the present invention were demonstrated to provide for expression of heterologous DNA sequences in plants. Specifically, leaf tissue of the same age as used above from both wildtype and B plants stem inoculated with Agrobacterium containing pMON417 were assayed for CAT activity according to the method described previously. A low level of CAT activity was detected in the leaves of stem inoculated wildtype plants while significantly higher levels (e.g. about 10–30 fold) were detected in the leaves of stem inoculated B plants. The low levels of CAT activity detected in leaves from stem inoculated wildtype plants may arise from endogenous CAT activity in wildtype plant cells or arise from secondary contamination by Agrobacterium containing pMON417 and, therefore, reflect either endogenous CAT activity in the Agrobacterium or production of CAT by chromosomally integrated copies of the CAT gene. The presence of plasmid DNA forms comprising TGMV-A DNA having inserted therein a CAT gene in the leaves from the inoculated B plants coupled with the significantly higher CAT activity found in these leaves, however, demonstrates that only the inoculated B plants are expressing the CAT gene carried in plasmid DNA molecules. These results are significant as they indicate that the geminivirus vectors of the present invention are capable of both replicating and expressing heterologous DNA sequences contained therein from autonomously replicating (e.g. plasmid) DNA molecules, that the generation of these plasmid DNA molecules provides for the amplification of gene-specific product production in plants transformed with these novel vectors, that the TGMV coat protein promoter is able to cause expression of heterologous DNA sequences in plants and that the presence of both the TGMV-A and TGMV-B components is required for systemic movement of the plasmid DNA molecules resulting from transformation of plants with the vectors of the present invention.

Expanded Disclosure

Figure 32:
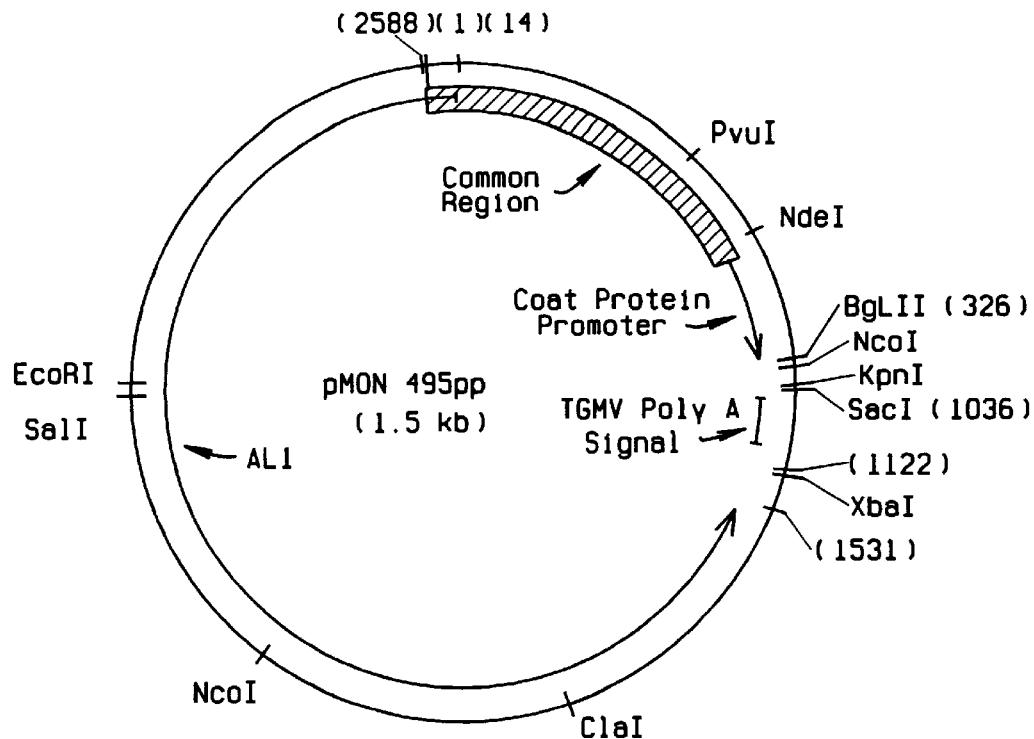
FIG. 32 depicts plasmid pMON495pp.

FIG. 32 depicts plasmid pMON495pp which contains those sequences of TGMV-A DNA sufficient to provide for autonomous replication of a DNA molecule in a plant cell. The parenthetical numbers in this and the following Figures denote the TGMV-A nucleotides (Hamilton et al., 1984), "kb" denotes kilobases, "pp" denotes plant plasmid and the hatched box denotes the TGMV common region.

Figure 33:
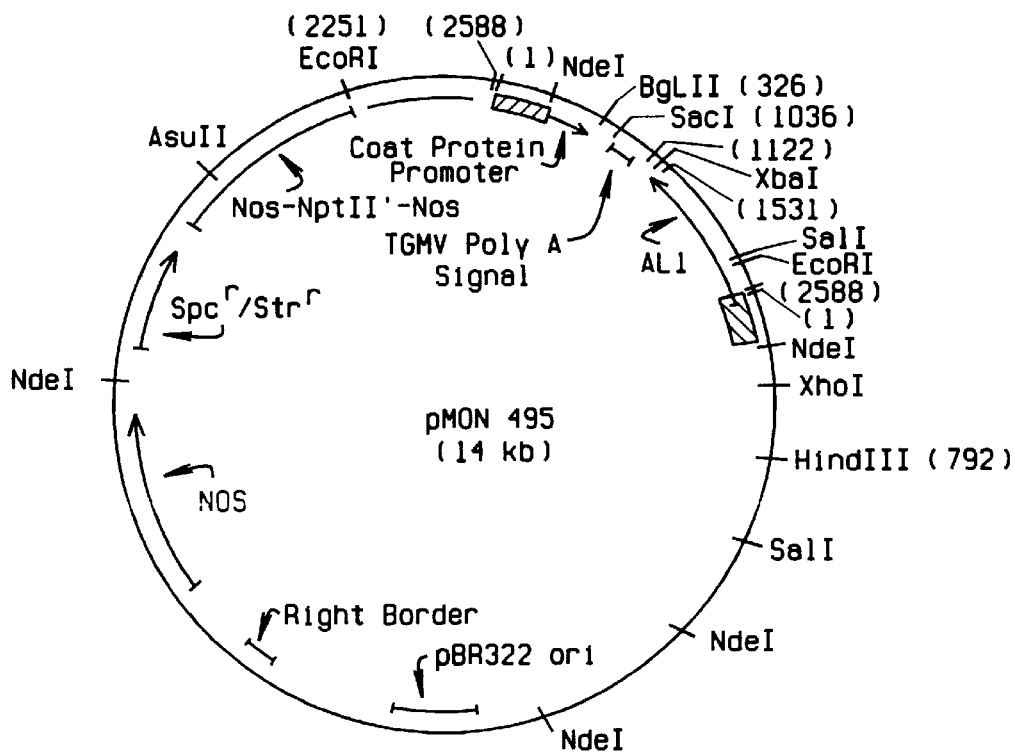
FIG. 33 depicts plasmid pMON495.

FIG. 33 depicts pMON495, a DNA molecule which can be employed in a free DNA or an *A. tumefaciens* transformation system to give rise to plasmid pMON495pp in a plant cell. In this and the following Figures, "Str$^r$ " denotes a streptomycin resistance gene, "NOS-NptII'-NOS" denotes a kanamycin resistance gene and "NOS" denotes a nopaline synthase gene.

Figure 34:
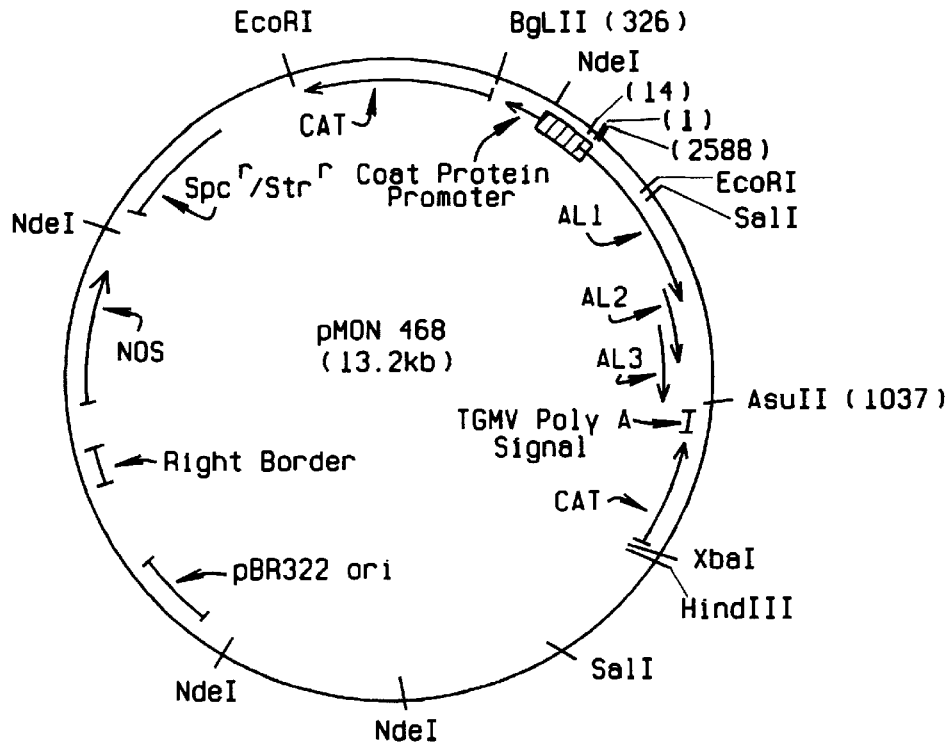
FIG. 34 depicts plasmid pMON468.

FIG. 34 depicts pMON468, a DNA molecule which can be employed in a free DNA or an *A. tumefaciens* transformation system to give rise to plasmid pMON468pp. "CAT" denotes a chloramphenicol acetyl transferase coding sequence.

Figure 35:
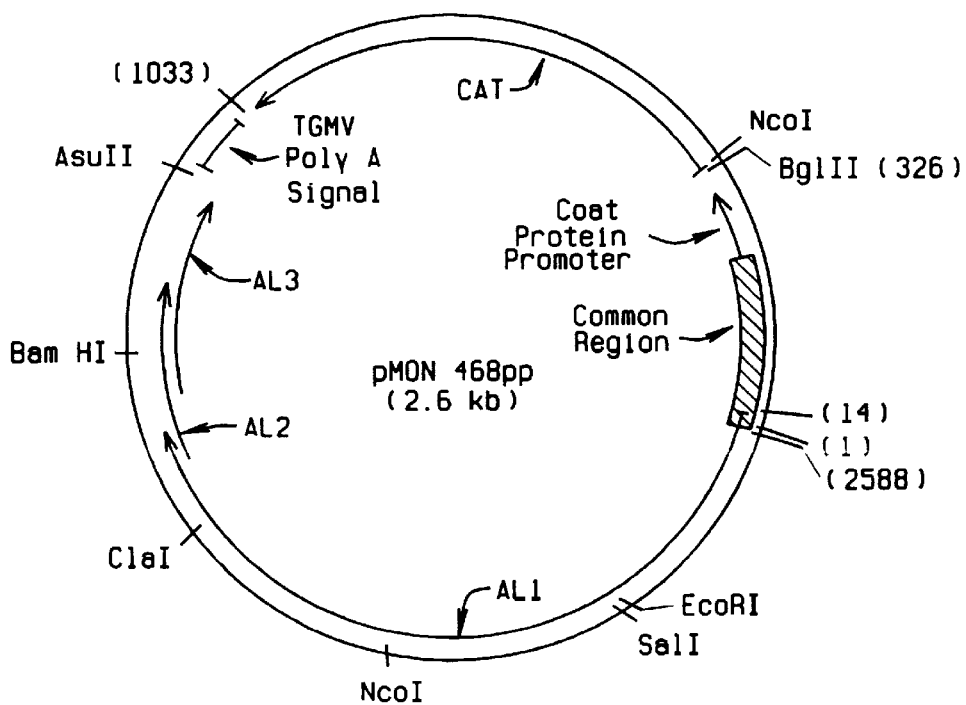
FIG. 35 depicts plasmid pMON468pp.

FIG. 35 depicts plasmid pMON468pp, a plant plasmid (pp) DNA molecule comprising a DNA sequence coding for a geminivirus trans-acting factor, a portion of a geminivirus DNA sequence responsive to the geminivirus trans-acting factor and a DNA sequence coding for a desired heterologous gene product. "CAT" denotes a chloramphenicol acetyl transferase coding sequence.

Figure 36:
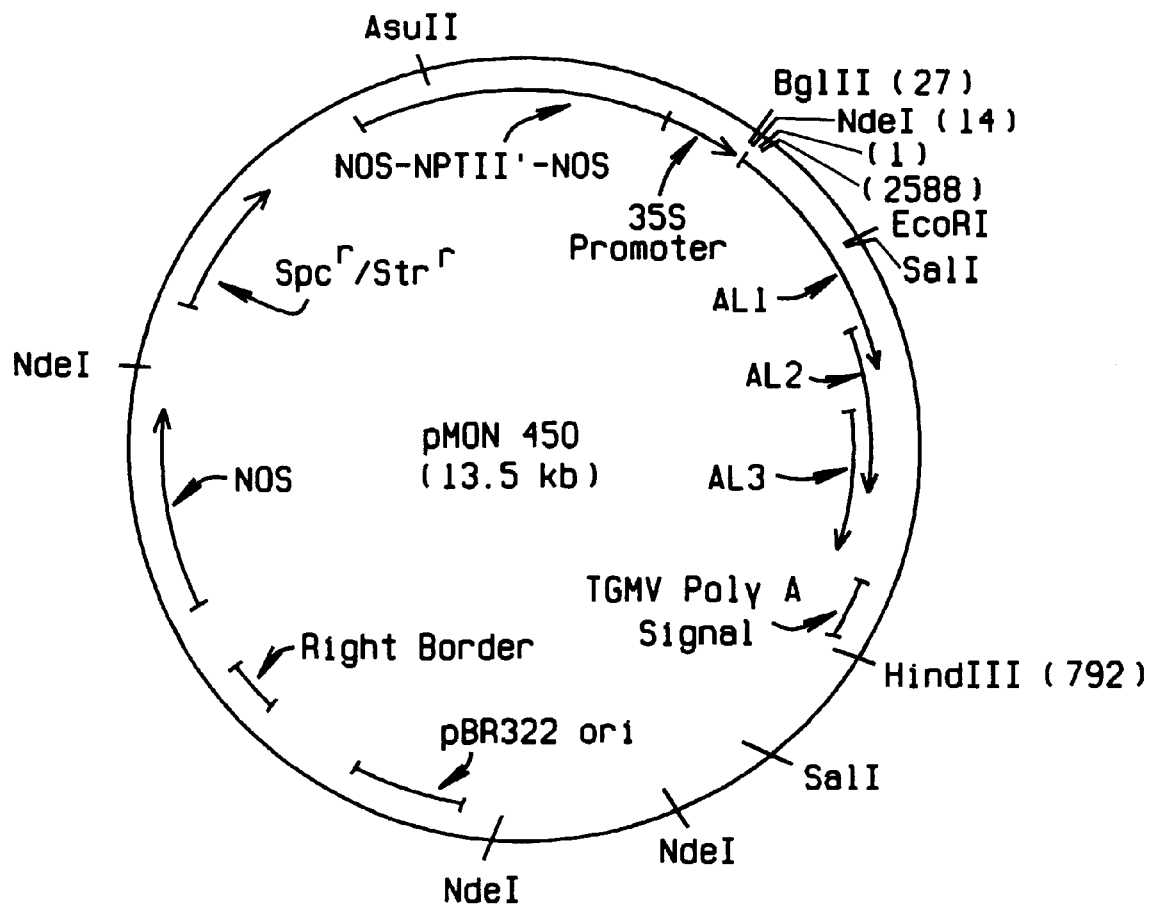
FIG. 36 depicts plasmid pMON450.

FIG. 36 depicts plasmid pMON450, a plasmid DNA molecule comprising TGMV AL1, AL2 and AL3 coding sequences under the control of a CaMV 35S promoter, denoted "35S promoter", a TGMV-A poly A signal sequence, denoted "TGMV Poly A Signal", and *A. tumefaciens* sequences which permit integration into a plant cell genome using a binary *A. tumefaciens* transformation system.

As previously described, the present invention relates to the discovery that all the elements (e.g. genes and/or DNA sequences) necessary for the replication of geminivirus DNA in a plant cell are contained on one of the two components of binary (i.e. two component genome or split genome) geminiviruses.

Specifically, it was discovered that the DNA component carrying the sequence encoding the geminivirus coat protein contains all the elements necessary for replication. Said DNA component has been alternatively referred to as the "A" or "1" component in the scientific literature. For purposes of uniformity, said DNA component is referred to herein as "coat protein-encoding geminivirus DNA" owing to the fact that, in nature, said component comprises sequences encoding a geminivirus coat protein (see e.g. FIG. 1A).

Based on the discovery that coat protein-encoding geminivirus DNA contains all the elements necessary for virus replication, the foregoing disclosure also describes novel plasmids, vectors, DNA molecules and methods employing said geminivirus DNA component which provide for the creation of plasmid DNA in plant cells and methods providing for the replication and/or expression of desired DNA sequences in plant cells, tissue and transgenic plants. A "plasmid" is herein understood to mean a molecule able to autonomously (e.g. extrachromosomally) replicate in a cell.

As previously described, tomato golden mosaic virus (TGMV) exemplifies a split genome (e.g. binary) geminivirus which can be employed in the methods of the present invention. Other binary geminiviruses useful in the present invention have been previously described in the foregoing disclosure. As previously discussed herein, the single genome geminiviruses such as maize streak virus (MSV) wheat dwarf virus (WDV) and beet curly top virus (BCTV) can also be employed in the methods of the present invention.

FIGS. 1A and 1B show the two TGMV DNA components, referred to as components A and B, respectively, each approximately 2.5 kilobases (kb) in size. As shown in FIG. 1A, the A component carries a DNA sequence encoding the virus coat protein. Hence, the A component exemplifies a coat protein-encoding geminivirus DNA molecule.

As previously described herein, transgenic petunia plants containing tandem repeats of either the TGMV A and B DNA's integrated into their chromosomes can be obtained using a disarmed *Agrobacterium* (*A.*) *tumefaciens* T-DNA transformation system. Only those plants containing the TGMV-A component contained freely replicating (e.g. plasmid) A component DNA molecules. This result demonstrates that all the virus functions necessary for replication are encoded by the A component (e.g., coat protein-encoding geminivirus DNA).

While neither the transgenic A- or B-containing plants exhibited virus disease symptoms, it was demonstrated, in Example 14, supra, that inoculation of B-containing plants with vectors comprising the TGMV A-component subsequently displayed virus symptoms. Subsequent experiments by Sunter et al (1987) have shown that one-quarter of the progeny produced by crossing a transgenic A plant with a transgenic B plant show geminivirus symptoms and contain infectious virus particles. These results show that the integrated tandem copies of the TGMV DNA's are functional, are able to be released from their integrated state and maintain their ability to produce infectious virus when genetically combined in the same cell. These results further demonstrate that the A component contains the necessary sequences and/or genes to enable release of B component DNA from its integrated state. Specifically, the ability of TGMV-A component DNA (e.g. coat protein-encoding geminivirus DNA molecules) to cause the release and subsequent replication of TGMV-B component DNA molecules, demonstrates that a geminivirus trans-acting factor(s) is (are) encoded in the TGMV-A component DNA. Additionally, these results demonstrate that both the TGMV-A and -B component DNA's contain a sequence or sequences responsive to the geminivirus trans-acting factor (s). A geminivirus DNA sequence responsive to a geminivirus trans-acting factor is understood herein to mean a geminivirus DNA sequence, the presence of which coupled to the presence of a geminivirus trans-acting factor, results in the autonomous replication of a DNA molecule containing the responsive sequence. it was further demonstrated, in Examples 13 and 14 supra, that heterologous DNA sequences can be inserted into and/or in place of the coat protein gene without disrupting the ability of the TGMV A-component to form plasmid DNA molecules in plant cells or cause disease symptoms in transgenic plants containing tandem copies of the TGMV B-component. These results demonstrate that the DNA sequences coding for the geminivirus coat protein per se are not required for replication of geminivirus DNA or geminivirus-containing plasmid DNA molecules in plants and/or plant cells. Specifically, Examples 13 and 14, supra, teach that neither the geminivirus trans-acting factor nor sequences responsive to said factor are contained within the DNA sequences encoding the TGMV coat protein. These foregoing examples further set forth a method by which one of skill in the art can determine the minimal sequence or sequences required for binary geminivirus replication in a plant cell. Specifically, the foregoing examples demonstrate that by performing conventional deletion and/or mutation analysis, a minimal binary geminivirus replicon can be determined.

The foregoing disclosure thus describes methods which enable one of skill in the art to define the minimal portions or segments of the any geminivirus DNA required for replication of any geminivirus DNA in plant cells, tissue and transgenic plants. This expanded disclosure now describes the results of the application of such methods and thus provides additional examples of those portions of geminivirus DNA and, specifically, the coat protein-encoding geminivirus DNA component, sufficient to enable geminivirus replication in a plant cell. Furthermore, in keeping with the general teachings of the present invention, said portions or segments derived from the coat protein-encoding geminivirus DNA can now be employed to create plasmids and/or DNA molecules useful in the methods of the present invention.

The examples provided hereinafter further delineate those geminivirus DNA sequences which are sufficient for geminivirus replication in plants and/or plant cells. By employing such conventional methods as site-directed mutagenesis and site-specific deletion analysis, it has been determined that the TGMV A sequences shown in FIG. 32 are sufficient to enable replication of DNA molecules containing these sequences in a plant cell. The arbitrary numbering of the TGMV-A component nucleotides used herein is based upon the numbering published by Hamilton et al., 1984, wherein nucleotide number 1 is within the common region and numbering proceeds around the A-component DNA in a clockwise fashion to nucleotide 2588. The examples provided hereinafter further delineate those geminivirus DNA sequences coding for a geminivirus trans-acting factor(s) and geminivirus sequences responsive to said trans-acting factor(s).

In order for a DNA molecule to function and exist as a plasmid DNA (e.g. autonomously replicating molecule) in a cell, such molecules must necessarily contain an origin of replication. An "origin of replication" is herein understood to mean a cis-acting DNA sequence or sequences which provide a site or sites for initiation of replication of a DNA molecule in a cell. Such cis-acting sequence(s) typically comprise a sequence(s) responsive to a trans-acting factor (s). While applicants have previously stated their belief that an origin of replication is contained within the common region of binary geminivirus DNA components, the present invention has at least localized such an origin (e.g. trans-acting responsive sequence or sequences) within those DNA sequences shown in FIG. 32 (e.g. nucleotides 1–326, 1036–1122 and/or 1531–2588). Further characterization and localization of a specific sequence or sequences able to function as an origin of replication (e.g. a sequence responsive to a trans-acting factor) are thus now made available to those of skill in the art using conventional mutational and deletion technologies by virtue of the teachings herein. Such further characterizations are therefore understood to be embraced by the general teachings and inventions described herein.

Furthermore, although the sequences shown in FIG. 32 are particular to the TGMV A-component DNA, it is understood that DNA sequences present in analogous and/or substantially homologous regions of other geminivirus DNA molecules constitute equivalent sequences to those shown in FIG. 36 and can now be identified by those of skill in the art. Such other geminivirus DNA molecules include, but are not limited to the TGMV B-component, MSV, WDV, BCTV, cassava latent virus (CLV) and bean golden mosaic virus (BGMV).

For example, the sequences set forth in FIG. 32 include a common region, the first leftward open reading frame (e.g. AL1) and about 80 nucleotides including and surrounding the bidirectional poly A signal sequence. The DNA sequences of such other geminivirus DNA components as CLV and BGMV have been published by Stanley and Gay (1983) and Howarth et al (1985), respectively. Such published sequences coupled to the specific teachings herein provides for an identification of equivalent sequences in said DNA components by virtue of their respective localization and/or sequence homology and, ultimately, functional analysis in accordance with the teachings of the present invention.

It is furthermore understood that the B-component DNA must necessarily contain an origin of replication (e.g. a sequence responsive to the binary geminivirus trans-acting factor). It is applicants' belief that this origin of replication would be comprised of sequences substantially homologous to those identified herein on the A-component. Specifically, the origin is believed to be localized within the B-component common region and/or other regions of homology between the A and B component DNA's.

As previously discussed, the present invention has further identified and teaches that the coat protein-encoding geminivirus DNA component (e.g. TGMV- A DNA) provides a trans-acting factor(s) which factor(s) is (are) required for replication of geminivirus-containing DNA molecules in plants and/or plant cells. Building from this discovery, described hereinbefore, this expanded disclosure now describes the further localization of the geminivirus DNA sequences which encode said factor or factors. Specifically, it is believed that the trans-acting factor(s) is (are) encoded in nucleotides from about 1531 to about 2588 and 1 to about 14 of TGMV-A component DNA, a portion or fragment thereof and/or equivalent nucleotides in analogous geminivirus DNA components.

As shown in the examples below, a DNA molecule containing a gene comprising an AL1 coding sequence (see FIG. 1A) is sufficient to enable tandem copies of the TGMV B-component, integrated into a plant cell genome, to become free of the host cell DNA and autonomously replicate in a plant cell. Hence, the geminivirus trans-acting factor(s) is (are) believed to be contained within the AL1 coding sequence or a portion thereof. As used herein, the term "gene" is understood to mean a DNA molecule or sequence containing all the elements or controls necessary for the expression (e.g. transcription and translation) of a given DNA coding sequence in a plant cell. As used herein, the terms "DNA sequences encoding an AL1 protein" or "AL1 coding sequence(s)" are understood to include the TGMV-A nucleotides from about nucleotide 1531 to about nucleotide 2588 and from 1 to about 14 and analogous and/or substantially homologous sequences contained within other geminivirus genomes. The AL1 coding sequence of TGMV and other binary and single gemone geminiviruses, as a group, represent a highly conserved sequence identifiable by such conventional techniques as hybridization and DNA sequence analysis. Such identifiable and identified sequences exemplify analogous and/or substantially homologous sequences to the specific AL1 sequences (e.g. nucleotide 1531 to about 2588 and nucleotide 1 to about 14) exemplified and herein.

The ability of an activated gene comprising an AL1 coding sequence to enable replication of DNA molecules containing a geminivirus origin of replication in a plant cell clearly demonstrates that a trans-acting factor or factors are encoded in the AL1 coding sequence or a portion thereof.

In a preferred working embodiment of the present invention, the AL1 coding sequence and geminivirus origin of replication, which origin of replication is recognized by or capable of interacting with the trans-acting factor(s) encoded in the AL1 sequence, are derived from the same geminivirus. The term "derived from" is herein understood to mean a DNA sequence or sequences which are directly obtained from geminivirus DNA and synthetic (e.g. chemically or enzymatically synthesized) sequences which are identical to or substantially the same as a sequence or sequences contained within naturally occurring geminivirus DNA.

Having now identified those DNA sequences which are sufficient to cause replication of geminivirus-containing DNA molecules in a plant and/or plant cell, it is now possible to construct plasmid DNAs which provide for the replication and/or expression of a desired (e.g. heterologous) DNA sequence in a plant and/or plant cell. Such a plasmid would minimally contain a geminivirus origin of replication (e.g. geminivirus sequence responsive to a geminivirus trans-acting factor) and a gene encoding the desired heterologous peptide. The term "heterologous" is herein understood to mean those proteins or nucleic acid sequences not naturally produced by or contained within a geminivirus, respectively. The trans-acting factor(s) encoded in the AL1 sequences can be provided by placing a gene encoding an AL1 protein within the plasmid DNA molecule or in an alternate site within the plant cell genome (e.g. within the plant cell chromosome or on a separate plant plasmid).

As previously described herein, such plasmids can be directly inserted into a plant cell by conventional methodologies. Expression and replication of the gene encoding the desired peptide is then achieved by culturing the transformed plant cells under standard conditions which allow for the expression of the gene encoding the trans-acting factor and gene encoding the desired peptide.

The present invention is further directed to methods for inducing or causing formation of plasmid DNA in plant cells. In accordance with these methods, the genomes of the plant cells typically contain DNA molecules able to give rise to plasmid DNA's. As previously discussed, the construction of DNA molecules able to give rise to plasmid DNA in a plant cell depends upon the method chosen for the introduction of such DNA molecules into a plant or plant cell. Conventional methods for introduction of DNA into plants include inoculation of plants, plant tissue and/or cells with purified DNA molecules and/or inoculation using a *A. tumefaciens* transformation system.

Also, as previously described, such DNA molecules which are able to give rise to plasmid DNA minimally contain those geminivirus sequences necessary for replication which sequences are flanked by or also contain directly repeating ends. Hence, such a DNA molecule would comprise a DNA sequence containing a binary geminivirus sequence responsive to a geminivirus trans-acting factor (e.g. an origin of replication), a gene encoding a binary geminivirus trans-acting factor (e.g. an AL1 protein) and having directly repeating ends. When employing an *A. tumefaciens* delivery system, the DNA molecules would also contain *A. tumefaciens* T-DNA.

As previously described, the directly repeating ends of a DNA sequence which can give rise to a plasmid DNA in a plant cell should be of a sufficient length to permit release of the DNA sequence from the plant vector and/or plant chromosome. Prior examples herein demonstrated the use of directly repeating ends comprising binary geminivirus common region sequences. This expanded disclosure provides further examples of sequences not derived from geminivirus DNA which can be employed to generate the directly repeating ends and thus provides additional examples of the types of DNA molecules useful in inducing formation of plasmid DNA in plants and/or plant cells.

Microorganisms and Plasmids

The afore-specified microorganisms have been deposited with the ATCC under the terms of the Budapest Treaty. Upon issuance of a U.S. patent citing the above-specified microorganisms, the ATCC is obligated to make such microorganisms available, without restriction or condition for a period of at least thirty (30) years and for a period of at least five (5) years after the most recent request for a sample.

Expanded Example 1

This example demonstrates that the sequences shown in FIG. 36 are sufficient to induce formation of a plasmid DNA in a plant cell.

In accordance with the methods previously described, a 14 kilobase (kb) DNA molecule designated pMON495 (FIG. 33) was constructed for use in a disarmed binary *A. tumefaciens* transformation system. As shown in FIG. 33, pMON495 contains a T-DNA right border sequence, a kanamycin resistance gene (NOS-NPTII'-NOS), spectinomycin and streptomycin resistance genes ($Spc^r/Str^r$), a pBR322 origin of replication, a DNA sequence comprising a TGMV AL1 coding sequence, about 80 nucleotides including and surrounding the TGMV bidirectional poly A signal sequence, the TGMV coat protein promoter sequence and wherein said DNA sequence has directly repeating ends comprising TGMV common region sequences. The promoter which provides for expression of the AL1 coding sequence is contained within the common region. In accordance with the nucleotide numbering system published by Hamilton et al. (1984; nucleotides 1–326, 1036–1122 and 1131–2588 of TGMV-A component DNA are contained within pMON495.

Leaf discs from Mitchell diploid petunia plants were transformed with pMON495 in accordance with the binary *A. tumefaciens* transformation system described in Example 13, supra. Total DNA was isolated from the transformed cells and subjected to Southern blot analysis in accordance with the procedures described, supra. The double-stranded DNA plasmid, pMON495pp, shown in FIG. 32 was thereby detected and its size of about 1502 bp verified by digestion with BglII and subsequent sizing by agarose gel electrophoresis.

The ability to detect freely replicating forms of pMON495pp (FIG. 32) in transformed plant cells clearly demonstrates that pMON495pp molecule contains all the geminivirus-specific DNA sequences sufficient for replication in a plant cell. Specifically, pMON495pp contains both the geminivirus encoded trans-acting factor(s) and geminivirus DNA sequences responsive to said factor(s). The ability to detect freely replicating forms of pMON495pp in transformed plant cells further demonstrates that a DNA molecule exemplified by pMON495 (FIG. 33) which comprises a DNA sequence comprising a gene encoding a geminivirus trans-acting factor and a DNA sequence responsive to said factor and wherein the DNA sequence has directly repeating ends, is able to give rise to geminivirus-containing plasmid DNA in a transformed plant cell.

Expanded Example 2

This example demonstrates that DNA molecules comprising a DNA sequence containing a geminivirus origin of replication (e.g. DNA sequences responsive to the geminivirus trans-acting factor), a gene encoding an AL1 protein (e.g. geminivirus trans-acting factor) and having directly repeating ends comprising a desired gene encoding the desired peptide are able to give rise to plasmid DNA molecules able to replicate and express the desired gene in a plant cell.

Specifically, a 13 kb DNA molecule, designated pMON468, was constructed in accordance with the conventional recombinant DNA procedures described, supra. As shown in FIG. 34, pMON468 contains all the TGMV-A component DNA sequences except for those sequences encoding the TGMV coat protein. Thus, pMON468 contains the TGMV-A DNA nucleotides from about 1 to about 326 and about 1037 to about 2588. Also, as shown in FIG. 34, the TGMV-A sequences are flanked by directly repeating DNA sequences comprising DNA sequences encoding the CAT gene product. The DNA sequences encoding the CAT gene may be obtained as a BglII/AsuII fragment from pMON375 (FIG. 12) for purposes of constructing pMON468. As shown in FIG. 34, expression of the CAT sequences is under the control of the TGMV coat protein promoter. The pMON468 molecule can be used in either a free DNA or *A. tumefaciens* transformation system.

In this Expanded Example 2, leaf discs from petunia plants were transformed with pMON468 in accordance with the binary *A. tumefaciens* transformation system previously described herein. A portion of the transformed petunia cells were assayed for CAT activity in accordance with the methods previously described herein. The results of these assays showed production of an active CAT protein in the transformed cells. Additionally, total DNA from another portion of the transformed petunia cells was isolated and subjected to Southern blot analysis as previously described. These analyses demonstrated the presence of a freely replicating DNA molecule, designated pMON468pp, shown in FIG. 35.

These results clearly demonstrate that a DNA molecule comprising a DNA sequence comprising a gene encoding a geminivirus trans-acting factor and geminivirus DNA sequences responsive to said transacting factor, which DNA sequence contains directly repeating ends comprising a DNA sequence coding for a desired polypeptide can give rise to geminivirus-containing plasmid DNA in a plant cell. These results further demonstrate that the resultant plasmid, shown in FIG. 35, is able to both replicate and express a desired gene in transformed plant cells.

Expanded Example 3

The following example demonstrates that a desired heterologous polypeptide can be produced systemically in transformed plants and, hence, that a geminivirus-containing DNA molecule can retain mobility in transformed plants.

In accordance with the methods described in Example 14, supra, transformed plants containing tandem integrated copies of TGMV-B DNA were stem inoculated with Agrobacterium containing pMON468 (FIG. 34). Leaf tissue was then taken from the inoculated plants for DNA analysis and CAT activity analysis when chlorotic spots became present on the newly emerged leaves of the inoculated B-containing plants (at 2–4 weeks). DNA analysis confirmed the presence of freely replicating DNA molecules of the type shown in FIG. 35. These results demonstrate the ability of geminivirus-containing DNA molecules to autonomously replicate heterologous DNA and move from cell to cell in plants containing integrated copies of the TGMV-B component. Furthermore, the positive detection of CAT activity in newly emerged leaves demonstrated the ability of mobile geminivirus-containing DNA molecules to provide for the production of heterologous proteins in such plants.

Expanded Example 4

This example demonstrates that an AL1 coding sequence encodes a trans-acting factor(s) which factor(s) is (are) able to interact with a geminivirus origin of replication (e.g. trans-acting responsive sequence) to enable autonomous replication of DNA molecules comprising geminivirus sequences. Specifically, this example demonstrates the ability of a chromosomally integrated DNA sequence comprising a gene encoding an AL1 protein to provide for the autonomous replication of TGMV B-component DNA and a TGMV-A component DNA carrying a mutation in the AL1 coding sequence.

As in the case for all DNA molecules described in this expanded disclosure, the DNA molecules of this Expanded Example 4 were constructed using the conventional recombinant DNA methodologies set forth hereinbefore.

Transgenic *N. benthamiana* plants were made using pMON450 (FIG. 36) by the method previously described, supra. The geminivirus DNA sequences contained within the integrated pMON450 molecule are not released from their integrated state as they do not contain (e.g. are not flanked by) directly repeating DNA sequences. Progeny from one self-crossed primary transgenic plant containing a chromosomally integrated pMON450 molecule were germinated on media containing 300 ug/ml kanamycin to select for plants which inherited the integrated pMON450 DNA. These plants were stem-inoculated, as previously described, supra, with Agrobacterium containing either pMON441 or Agrobacterium containing pMON308 (FIG. 2B). The pMON441 molecule was created from pMON337 (FIG. 29) by filling in the unique SalI site. The filling in of the SalI site results in a four nucleotide insertion in the AL1 gene and creation of a new PvuI site.

Subsequent, total DNA analysis of newly emerged leaves from the stem-inoculated pMON450 transgenic plants showed that the pMON441 is capable of releasing a TGMV-A component containing a four nucleotide insertion mutation in the AL1 gene at the previous SalI site when introduced into the transgenic plant cell via Agrobacterium mediated T-DNA transfer. The pMON308 molecule is similarly capable of releasing a normal TGMV-B component when introduced into the transgenic plant via Agrobacterium mediated T-DNA transfer. Neither the mutant TGMV-A component contained within pMON441 nor the TGMV-B component contained within pMON308 are capable of autonomous replication in normal plants due to the lack of a functional trans-acting factor(s) in said plants or plant cells.

Viral symptoms typical of TGMV infection appeared on 12 out of 18 plants 12–17 days after inoculation. Southern blot analysis revealed the presence of freely replicating forms of the mutant TGMV-A and normal TGMV-B component DNA in the symptomatic tissue of the pMON450 transgenic plants. These results indicate that the TGMV AL1 gene product made by the pMON450 containing transgenic plants acts in trans to support the replication of the mutant TGMV-A component from pMON441 and normal TGMV-B component from pMON308.

REFERENCES

Bale, A., d'Alarcao, M. and Marinus, M. G. (1979) Characterization of DNA adenine methylation mutants of Escherichia coli K12. Mutation Res. 59, 157–165.

Barker et al. (1983) Plant Mol. Biol. 2, 335.

Bevan, M. W. (1984) Binary Agrobacterium vectors for plant transformation. Nucl. Acids Res. 12, 8711–8721.

Bisaro, D. M. Hamilton, W. D. O., Coutts, R. H. A. and Buck, K. W. (1982) Molecular cloning and characterization of the two DNA components of tomato golden mosaic virus. Nucl. Acids Res. 10, 4913–4922.

Bock, K. R. (1982) Geminivirus diseases in tropical crops. Plant Disease 66, 266–270.

Brisson, N., Paszkowski, J., Penswick, J. R., Gronenborn, B., Potrykus, I. and Hohn, T. (1984) Expression of a bacterial gene in plants by using a viral vector. Nature 310, 511–514.

Buck, K. W. and Coutts, R. H. A. (1983) The potential of geminiviruses in the construction of plant host vector ssytems. Plant Molecular Biology 2, 351–354.

Canon, F. C., Postgate, J. R., and Primrose, S. B. (1974) "Chromosomal Integration of Klebsiella Nitrogen Fixation Genes in *E. coli*." Journal of General Microbiology 80 , 227–239.

Davis, R. W., Botstein, D. and Roth, J. R. (1980) Advanced bacterial genetics. Cold Spring Harbor Laboratory, New York.

DeBlock, M., Herrera-Estrella, L., Van Montagu, M. Schell, J. Zambryski, P. (1984) Expression of foreign genes in regenerated plants and their progeny. EMBO J. 3, 1681–1689.

Dellaporta, S. L., Wood, J. and Hicks, J. B. (1983) A plant DNA minipreparation: Version II. Plant Mol. Biol. Reporter 1, No. 4, 19–21.

Fraley, R., Rogers, S., Horsch, R., Sanders, P., Flick, J. Adams, S., Bittner, M., Brand, L., Fink, C., Fry, J., Galluppi, J. Goldberg, S., Hoffmann, N. and Woo, S. (1983) Expression of bacterial genes in plant cells. Proc. Natl. Acad. Sci. USA 80, 4803–4807.

Fraley, R. T., Rogers, S. G., Horsch, R. B., Eichholtz, D., Flick, J. S., Fink, C. L., Hoffmann, N. L. and Sanders, P. R. (1985) The SEV system: A new disarmed Ti plasmid vector for plant transformation. Bio/Technology 3, 629–635.

Francki, R. J. B., Milne, R. G. and Hattan, T. (1985) *Atlas of Plant Viruses*, Vol. I pp. 33–46, CRC Press, Inc. Boca Raton, Fla.

Freeman, J. P., Draper, J., Davey, M. R., Cocking, E. C., Gartland, K. M. A., Harding, K. and Pental, D. (1984) A comparison of methods for plasmid delivery into plant protoplasts. Plant and Cell Physiol. 25, 1353–1365.

Fromm, M., Taylor, L. P. and Walbot, V. (1985) Expression of genes transferred into monocot and dicot plant cells by electroporation. Proc. Natl. Acad. Sci., USA, 82, 5824–5828.

Goodman, R. M. (1981) Geminivirus. J. Gen. Virol. 54, 9–21.

Griesbach, R. J. (1983) Protoplast microinjection. Plant Molecular Biology Reporter, 1, No. 4, 32–37.

Gronenborn, B., Gardner, R. C., Schaefer, S. and Shepherd, R. J. (1981) Propagation of foreign DNA in plants using cauliflower mosaic virus as vector. Nature 294, 773–776.

Hamilton, W. D. O., Sanders, R. C., Coutts, R. H. A. and Buck, K. W. (1981) Characterization of tomato golden mosaic virus as a geminivirus. FEMS Microbiology Letters 11, 263–267.

Hamilton, W. D. O., Bisaro, D. M. and Buck, K. W. (1982) Identification of novel DNA forms in tomato golden mosaic virus infected tissue: Evidence for a two component viral genome. Nucl. Acids Res. 10, 4910–4912.

Hamilton, W. D. O., Bisaro, D. M., Coutts, R. H. A. and Buck, K. W. (1983) Demonstration of the bipartite nature of the genome of a single-stranded plant virus by infection with the cloned DNA components. Nucl. Acids Res. 11, 7387–7396.

Hamilton, W. D. O., Stein, V. E., Coutts, R. H. A. and Buck, K. W. (1984) Complete nucleotide sequence of the infectious cloned DNA components of tomato golden mosaic virus: Potential coding regions and regulatory sequences. The EMBO J. No. 3, 2197–2205.

Hauptmann, R. and Widholm, J. (1982) Plant Physiol. 70, 30–34.

Hoekema, A., Hirsch, P. R., Hooykaas, P. J. J. and Schilperoort, R. A. (1983) A binary plant vector strategy based on separation of vir- and T-region of the *Agrobacterium tumefaciens* Ti-plasmid. Nature 303, 179–180.

Horsch, R. B., Fraley, R. T., Rogers, S. G., Sanders, P. R., Lloyd, A. and Hoffmann, N. L. (1984) Inheritance of functional foreign genes in plants. Science 223, 496–498.

Horsch, R. B., Fry, J. E., Hoffmann, N. L., Wallroth, M., Eichholtz, D., Rogers, S. G. and Fraley, R. T. (1985) A simple and general method for transferring genes into plants. Science 227, 1229–1231.

Howarth, A. J., Caton, C., Bossert, M. and Goodman, R. M. (1985) Nucleotide sequence of bean golden mosaic virus and model for gene regulation in geminiviruses. Proc. Natl. Acad. Sci., USA 82, 3572–3576.

Howell, S. H. (1984) Physical structure and genetic organization of the genome of maize streak virus (Kenyan isolate). Nucl. Acids Res. 12, 7359–7375.

Howell, S. H. (1985) The molecular biology of plant DNA viruses. CRC Critical reviews in plant sciences. 2, 287–316.

Ish-Horowicz, D. and Burke, J. F. (1981) Rapid and efficient cosmid cloning. Nucl. Acids Res. 9, 2989–2998.

Kessler, C., Neumaier, P. S. and Wolf, W. (1985) Recognition sequences of restriction endonucleases and methylases—a review. Gene 33, 1–102.

Krens, F. A., Molendijk, L., Wullems, G. J. and Schilperoort, R. A. (1982) In vitro transformation of plant protoplasts with Ti-plasmid DNA. Nature 296, 72–74.

MacDowell, S. W., Macdonald, H., Hamilton, W. D. O., Coutts, R. H. A. and Buck, K. W. (1985) The nucleotide sequence of cloned wheat dwarf virus DNA. The EMBO J. 4, 2173–2180.

Maniatis, T., Fritsch, E. F. and Sambrook, J. (1982) Molecular Cloning, Cold Spring Harbor Laboratory, Cold Spring Harbor, N.Y.

Matyis, J. G., Silva, D. M., Oliveira, A. R. and Costa, A. S. (1975) Purificaco e morfologia do virus do mosaico dourado do tomateiro. Summa Phytopathol. 1, 267–274.

Mullineaux, P. M., Donson, J., Morris-Krsinich, B. A. M., Boulton, M. I. and Davies, J. W. (1984) The nucleotide sequence of maize streak virus DNA. The EMBO J., 3, 3063–3068.

Murray, N. E., Bruce, S. A. and Murray, K. (1979) Molecular cloning of the DNA ligase gene from bacteriophage T4. J. Mol. Biol. 132, 493–505.

Potrykus, I., Shillito, R. D., Saul, M. W. and Pazkowski, J. (1985) Direct gene transfer state of the art and future potential. Plant Molecular Biology Reporter, 3, 117–128.

Rogers, S. G., Fraley, R. T., Horsch, R. B., Levine, A. D., Flick, J. S., Brand, L. A., Fink, C. F., Mozer, T., O'Connell, K. and Sanders, P. R. (1985) Evidence for ribosome scanning during translation initiation of mRNAs in transformed plant cells. Plant Molecular Biology Reporter 3, 111–116.

Rogers, S. G., O'Connell, K. Horsch, R. B. and Fraley, R. T. (1985). Investigation of Factors Involved in Foreign protein Expression in Transformed Plants in Biotechnology in Plant Science, P. Day, M. Zaitlin and A. Hollaender, eds. Academic Press, New York, N. Y., pages 219–226.

Rogers, S. G., Horsch, R. B. and Fraley, R. T. (1986) "Gene transfer in plants: Production of transformed plants using Ti plasmid vectors" in Methods in Enzymology, Vol. 118 Weissbach, H. and Weissbach, A., ed., Academic Press, New York, pages 627–640.

Schmldhauser, T. J. and Helinski, D. R. (1985) Regions of the broad host range plasmid RK2 involved in replication and stable maintenance in nine different species of gram-negative bacteria. J. Bacteriology. 164,446–455.

Shewmaker, C. K., Caton, J. R., Houck, C. M. and Gardner, R. C. (1985) Transcription of Cauliflower Mosaic Virus integrated into plant genomes. Virology 140, 281–288.

Stanley, J. and Gay, M. (1983) The nucleotide sequence of cassava latent virus DNA. Nature 305, 643–645.

Sunter, G., Gardiner, W. E., Rushing, A. E., Rogers, S. G. and Bisaro, D. M. (1987) Independent encapsidation of tomato golden mosiac virus A component DNA in transgenic plants. Plant Mol. Biol., 8, 477–484.

Sutcliff (1978) Proc. Nat'l. Acad. Sci., U.S.A., 75, 3737–3741.

Thomashow, M. F., Nutter, R., Montoya, A. L., Gordon, M. P. and Nester, E. W. (1980) Integration and organization of Ti plasmid sequences in crown gall tumors. Cell 19, 729–739.

Townsend, R., Stanley, J., Curson, S. J., Short, M. N. "Major Polyadenylated Transcripts of Cassava Latent Virus and Location of the Gene Encoding Coat Protein." (1985) EMBO J.4, 33–37.

Vieira, J. and Messing, J. (1982) The pUC plasmids, an M13mp7-derived system for insertion mutagenesis and sequencing with synthetic universal primers. Gene 19, 259–268.

Yanisch-Perron, C., Vieira, J. and Messing, J. (1985) Improved M13 phage cloning vectors and host strains: nucleotide sequences of the M13mpl8 and pUC19 vectors. Gene 33, 103–119.

Zoller, M. J. and Smith, M. (1982) Oligonucleotide directed mutagenesis using M13-derived vectors: An efficient and general procedure for the production of point mutations in any fragment of DNA. Nucl. Acids Res. 10, 6487–6500.

In the claims:

1. A method for producing a heterologous peptide in a plant cell, the method comprising the steps of:
   (a) transforming the plant cell with a DNA molecule comprising a DNA fragment comprising a TGMV-A DNA sequence responsive to a TGMV-A trans-acting factor and a gene encoding the heterologous peptide and wherein the genome of the plant cell comprises an AL1 coding sequence coding for a TGMV trans-acting factor; and
   (b) culturing the transformed plant cell under conditions which allow for expression of the gene encoding the TGMV trans-acting factor and gene encoding the heterologous peptide, thereby obtaining the peptide.

2. The method of claim 1 in which the DNA fragment further comprises TGMV directly repeating ends.

3. The method of claim 1 in which the DNA molecule further comprises an *Agrobacterium tumefaciens* T-DNA and the DNA fragment further comprises TGMV directly repeating ends.

4. The method of claim 1 in which the DNA molecule further comprises an *Agrobacterium tumefaciens* T-DNA and the DNA fragment further comprises TGMV directly repeating ends comprising a TGMV common region.

5. The method of claim 1 in which the DNA molecule further comprises an *Agrobacterium tumefaciens* T-DNA and the DNA fragment further comprises TGMV directly repeating ends comprising the gene encoding the heterologous peptide.

* * * * *